US011111375B2

(12) United States Patent
Rodrigues et al.

(10) Patent No.: US 11,111,375 B2
(45) Date of Patent: *Sep. 7, 2021

(54) COMPOSITIONS AND METHODS FOR GENERATING OLIGODENDROCYTE PRECURSORS

(71) Applicant: The Regents of the University of California, Oakland, CA (US)

(72) Inventors: Gonçalo Rodrigues, Berkeley, CA (US); David V. Schaffer, Danville, CA (US)

(73) Assignee: The Regents of the University of California, Oakland, CA (US)

(*) Notice: Subject to any disclaimer, the term of this patent is extended or adjusted under 35 U.S.C. 154(b) by 64 days.

This patent is subject to a terminal disclaimer.

(21) Appl. No.: 15/758,231

(22) PCT Filed: Oct. 4, 2016

(86) PCT No.: PCT/US2016/055361
§ 371 (c)(1),
(2) Date: Mar. 7, 2018

(87) PCT Pub. No.: WO2017/062374
PCT Pub. Date: Apr. 13, 2017

(65) Prior Publication Data
US 2018/0251730 A1 Sep. 6, 2018

Related U.S. Application Data

(60) Provisional application No. 62/237,441, filed on Oct. 5, 2015.

(51) Int. Cl.
| | | |
|---|---|---|
| *C08L 51/00* | (2006.01) | |
| *C12N 5/079* | (2010.01) | |
| *C07D 471/04* | (2006.01) | |
| *C12N 5/00* | (2006.01) | |
| *A61K 35/28* | (2015.01) | |

(52) U.S. Cl.
CPC .......... *C08L 51/006* (2013.01); *C07D 471/04* (2013.01); *C12N 5/0018* (2013.01); *C12N 5/0622* (2013.01); *A61K 35/28* (2013.01); *C08L 2203/02* (2013.01); *C12N 2501/385* (2013.01); *C12N 2501/41* (2013.01); *C12N 2501/415* (2013.01); *C12N 2506/02* (2013.01); *C12N 2506/45* (2013.01); *C12N 2539/10* (2013.01)

(58) Field of Classification Search
CPC ............... C12N 5/0622; C12N 5/0018; C12N 2501/385; C12N 2501/41; C12N 2501/415; C12N 2506/02; C12N 2506/45; C12N 2539/10; C07D 471/04; C08L 51/006; C08L 2203/02; A61K 35/28
See application file for complete search history.

(56) References Cited

U.S. PATENT DOCUMENTS

| | | | |
|---|---|---|---|
| 7,579,188 B2 | 8/2009 | Keirstead et al. | |
| 2003/0049839 A1* | 3/2003 | Romero-Ortega ... | C12N 5/0622 435/397 |
| 2007/0249044 A1* | 10/2007 | Desai ................... | C12M 25/14 435/325 |
| 2009/0232779 A1 | 9/2009 | Keirstead et al. | |
| 2012/0315265 A1* | 12/2012 | Lai ........................ | A61P 29/00 424/130.1 |
| 2014/0045695 A1 | 2/2014 | Liebmann et al. | |
| 2014/0248696 A1* | 9/2014 | Zhang .................. | C12N 5/0623 435/366 |
| 2015/0064141 A1 | 3/2015 | Byrne | |
| 2015/0268236 A1 | 9/2015 | Stayton et al. | |

FOREIGN PATENT DOCUMENTS

JP 2012-139541 A 7/2012

OTHER PUBLICATIONS

Li, Y et al. Neural differentiation from pluripotent stem cells: The role of natural and synthetic extracellular matrix. World Journal of Stem Cells. Jan. 26, 2014. 6(1): 11-23. (Year: 2014).*
Yoshioka, H et al. A synthetic hydrogel with thermoreversible gelation, III: an NMR study of the sol-gel transition. Polymers for Advanced Technologies. 1994. 5: 122-127. (Year: 1994).*
Garbern, JC et al. Injectable pH- and temperature-responsive poly(N-isopropylacrylamide-co-propylacrylic acid) copolymers for delivery of angiogenic growth factors. Biomacromolecules. 2010. 11: 1833-1839. (Year: 2010).*
Douvaras, P et al. Efficient generation of myelinating oligodendrocytes from primary progressive multiple schlerosis patients by induced pluripotent stem cells. Stem Cell Reports. Aug. 12, 2014. 3: 250-259. (Year: 2014).*
Stanton, BZ et al. Small-molecule modulators of the Sonic Hedgehog signaling pathway. Mol. BioSyst. 2010. 6: 44-54. (Year: 2010).*
Lei, et al.; "A fully defined and scalable 3D culture system for human pluripotent stem cell expansion and differentiation"; PNAS; 10 pages (Nov. 18, 2013).
Rodrigues, et al.; "Defined and Scalable Differentiation of Human Oligodendrocyte Precursors from Pluripotent Stem Cells in a 3D Culture System"; Stem Cell Reports; vol. 8, 14 pages (Jun. 6, 2017).
Rodrigues, et al.; "Supplemental Information: Defined and Scalable Differentiation of Human Oligodendrocyte Precursors from Pluripotent Stem Cells in a 3D Culture System"; Stem Cell Reports; vol. 8, pp. 1770-1783 (Jun. 6, 2017).

(Continued)

*Primary Examiner* — David W Berke-Schlessel
*Assistant Examiner* — Susan E. Fernandez
(74) *Attorney, Agent, or Firm* — Bozicevic, Field & Francis LLP; Paula A. Borden

(57) ABSTRACT

The present disclosure provides a three-dimensional culture system comprising a biocompatible polymer and a combination of factors in an amount effective to induce differentiation of oligodendrocyte precursors and/or oligodendrocytes from pluripotent stem cells. The present disclosure provides methods of generating oligodendrocyte precursors and/or oligodendrocytes using a three-dimensional culture system of the present disclosure. The present disclosure provides methods to treat neurological diseases and demyelinating diseases.

13 Claims, 30 Drawing Sheets

Specification includes a Sequence Listing.

(56) References Cited

OTHER PUBLICATIONS

Chambers, et al.; "Highly efficient neural conversion of human ES and iPS cells by dual inhibition of SMAD signaling"; Nat Biotechnol; vol. 27, No. 3, pp. 275-280 (Mar. 2009).
Goldman, et al.; "Glial Progenitor Cell—Based Treatment and Modeling of Neurological Disease"; Science; vol. 338, No. 6106, pp. 491-495 (Oct. 26, 2012).
Richardson, et al.; "Oligodendrocyte wars"; vol. 7, No. 1, pp. 11-18 (Jan. 2006).
Wang, et al.; "Human iPSC-derived oligodendrocyte progenitors can myelinate and rescue a mouse model of congenital hypomyelination"; Cell Stem Cell; vol. 12, No. 2, pp. 252-264 (Feb. 7, 2013).

\* cited by examiner

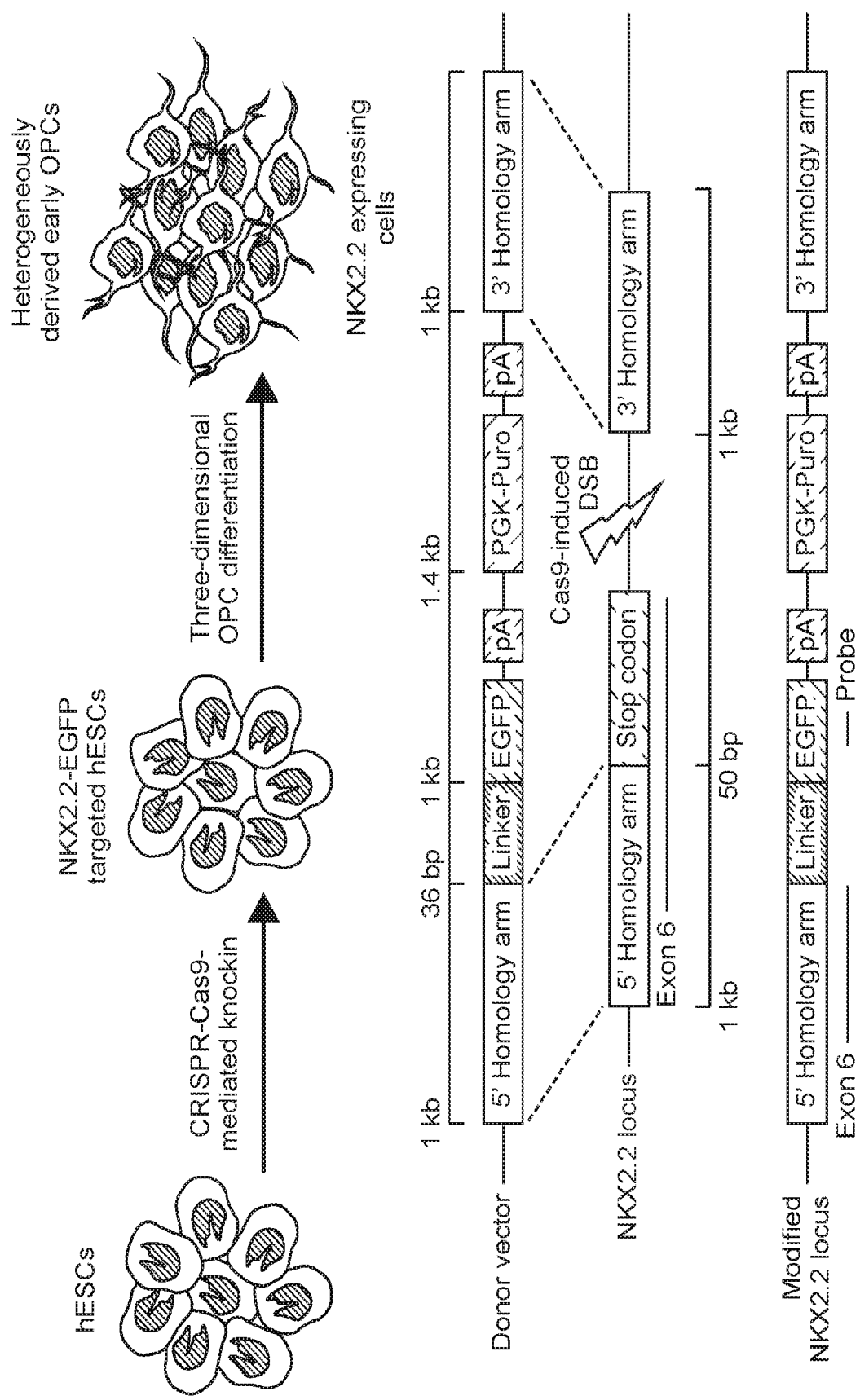

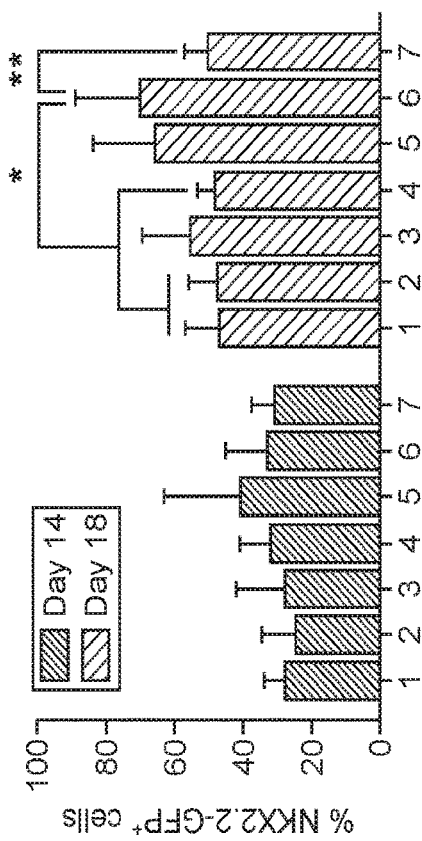
FIG. 4D
FIG. 4E
FIG. 4F
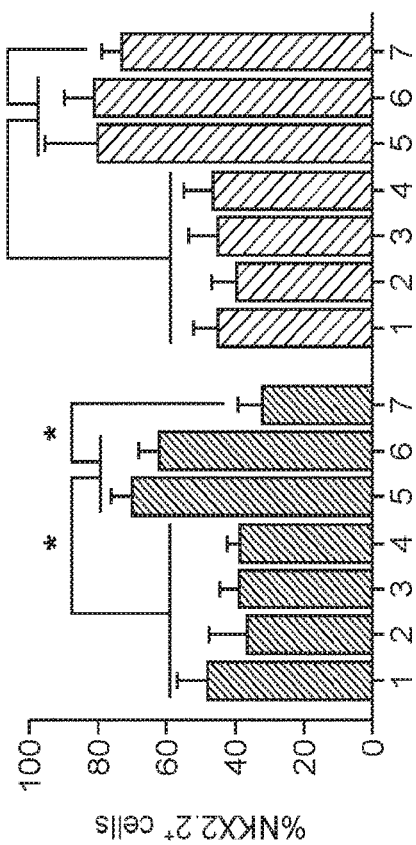
FIG. 4G
FIG. 4H

Day 95

DAPI/SOX10/O4/MBP

FIG. 19

| Primer reference | Sequence |
|---|---|
| ON-HA-1-Fwd | GGGTGGCCCGGGTATAAATAG (SEQ ID NO: 2) |
| ON-HA-1-Rev | GGTGGAATCTGCCACTCCAA (SEQ ID NO: 3) |
| IN-HA-1-Fwd | GATTACactagtGGCCCGAAAGCAGAAACGAAA (SEQ ID NO: 4) |
| IN-HA-1-Rev | ACCTGAcccggGCCAAGTCCACTGCTGGGCCTG (SEQ ID NO: 5) |
| ON-HA-2-Fwd | CAGCACATGCAGTACAACGC (SEQ ID NO: 6) |
| ON-HA-2-Rev | GTCACTTTTCCTCCCGTAGCC (SEQ ID NO: 7) |
| IN-HA-2-Fwd | ATTATcgccggcgCGGTGGCGGCGAGGAGGCCT (SEQ ID NO: 8) |
| IN-HA-2-Rev | ATATTcctgaggAGAGGAACCGCCTGTGGGAG (SEQ ID NO: 9) |
| IN-Diag-Fwd | GGGTGGCCCGGGTATAAATAG (SEQ ID NO: 10) |
| IN-Diag-Rev | CCTACTCAGACAATGCGATGC (SEQ ID NO: 11) |
| gRNA-NKX2.2-Fwd | caccGGCCCACCCCGGCGGCGG (SEQ ID NO: 12) |
| gRNA-NKX2.2-Rev | aaacCCGCCGCCGGGGTGGGGCC (SEQ ID NO: 13) |

FIG. 20

| Media | Days in use | Components | Company | Concentration |
|---|---|---|---|---|
| Full N2 | 0-3 | | | |
| | | DMEM/F12 medium | LF-11039-021 | 50% |
| | | Neurobasal medium | LF-21103-049 | 50% |
| | | Glutamax | LF-35050-061 | 1:100 |
| | | B27 | LF-17504-044 | 1:50 |
| | | N2 | LF-17502-048 | 1:100 |
| Half N2 | 5-10 | | | |
| | | DMEM/F12 medium | LF-11039-021 | 50% |
| | | Neurobasal medium | LF-21103-049 | 50% |
| | | Glutamax | LF-35050-061 | 1:100 |
| | | B27 | LF-17504-044 | 1:100 |
| | | N2 | LF-17502-048 | 1:200 |
| Neurobasal | 11-95 | | | |
| | | Neurobasal medium | LF-21103-049 | 50% |
| | | Glutamax | LF-35050-061 | 1:100 |
| | | B27 | LF-17504-044 | 1:500 |
| | | Pen Strep | LF-15140122 | 0.5% |
| Early OPC differentiation | 0-10 | | | |
| | 0-3 | Full N2 | | |
| | 4-10 | Half N2 | | |
| | 0-4 | SB431542 | SK-S1067 | 10µM |
| | 0-10 | LDN193189 | SK-S2618 | 100ηM |
| | 2-17[1] | SHH | Produced (Conway et al., 2013 | 100ηg/mL |
| | 2-17[2] | SAG | Xcessbio-M60081 | 1µM |
| | 0-3[3] | CHIR99021 | SK-1263 | 3µM |
| | 2-17[4] | RA | Sigma-R2625 | 100ηM |
| OPC proliferation medium | 11-17[5] | | | |
| | 11-17 | Neurobasal | | |
| | 14-17 | FGF-basic | Peprotech-100-18B | 10ηg/mL |
| OPC maturation medium | 18-95[6] | | | |
| | 18-95 | Neurobasal | | |
| | 18-95 | cAMP | Sigma-D0627 | 1µM |
| | 18-95 | IGF1 | Peprotech-100-11 | 10ηg/mL |
| | 18-95 | PDG-AA | Peprotech-100-13A | 10ηg/mL |
| | 18-95 | Insulin | Sigma-I2643 | 25µg/mL |
| | 18-95 | NT3 | Peprotech-450-03 | 10ηg/mL |
| | 18-95 | Biotin | Sigma-B4639 | 100ηg/mL |
| | 18-95 | T3 | Sigma-T2877 | 60ηg/mL |
| | 66-95 | Vitamin D | Cayman-71820 | 0.1µM |

FIG. 21

| Antibodies | Company | Cat. No. | Host | Dilution |
|---|---|---|---|---|
| OCT4 | Santa Cruz | sc-5279 | Mouse | 1:200 |
| NANOG | Santa Cruz | sc-33759 | Rabbit | 1:200 |
| PAX6 | Biolegend | PRB-278P | Rabbit | 1:300 |
| NKX2.2 Ab | DSHB | 74.5A5 | Mouse | 1:200 |
| OLIG2 | R&D | AF2418 | Goat | 1:100 |
| SOX2 | Santa Cruz | sc-17320 | Goat | 1:400 |
| KI-67 | ThermoFisher | PA5-16785 | Rabbit | 1:100 |
| PDGFαR | Santa Cruz | sc-338 | Rabbit | 1:400 |
| SOX10 | Santa Cruz | sc-17342 | Goat | 1:200 |
| O4 | R&D | mab1326 | MouseIgM | 1:100 |
| GFAP | Abcam | ab7260 | Rabbit | 1:200 |
| TUJ1 | Invitrogen | 480011 | Mouse | 1:1000 |
| MBP | Millipore | mab386 | Rat | 1:300 |
| RIP | DSHB | RIP | Mouse | 1:200 |
| NG2 | Millipore | Ab5320 | Rabbit | 1:200 |
| HNA | Millipore | mab1281 | Mouse | 1:100 |

FIG. 22

| Gene | Forward primer | Reverse primer |
|---|---|---|
| OCT4 | GTGTTCAGCCAAAAGACCATCT (SEQ ID NO: 14) | GGCCTGCATGAGGGTTTCT (SEQ ID NO: 23) |
| NKX2.2 | GTCAGGGACGGCAAACCAT (SEQ ID NO: 15) | GCGCTGTAGGCAGAAAAGG (SEQ ID NO: 24) |
| OLIG2 | CCAGAGCCCGATGACCTTTTT (SEQ ID NO: 16) | CACTGCCTCCTAGCTTGTCC (SEQ ID NO: 25) |
| SOX10 | CCTCACAGATCGCCTACACC (SEQ ID NO: 17) | CATATAGGAGAAGGCCGAGTAGA (SEQ ID NO: 26) |
| PDGFαR | TGGCAGTACCCCATGTCTGAA (SEQ ID NO: 18) | CCAAGACCGTCACAAAAAGGC (SEQ ID NO: 27) |
| MBP | GGCCGGACCCAAGATGAAAA (SEQ ID NO: 19) | CCCCAGCTAAATCTGCTCAGG (SEQ ID NO: 28) |
| GSX2 | ATGTCGCGCTCCTTCTATGTC (SEQ ID NO: 20) | CAAGCGGGATGAAGAAATCCG (SEQ ID NO: 29) |
| HOXB4 | CGTGAGCACGGTAAACCCC (SEQ ID NO: 21) | CGAGCGGATCTTGGTGTTG (SEQ ID NO: 30) |
| GAPDH | GGAGCGAGATCCCTCCAAAT (SEQ ID NO: 22) | GGCTGTTGTCATACTTCTCATGG (SEQ ID NO: 31) |

SEQUENCE LISTING

<160> NUMBER OF SEQ ID NOS: 31

<210> SEQ ID NO 1
<211> LENGTH: 462
<212> TYPE: PRT
<213> ORGANISM: Homo Sapiens

<400> SEQUENCE: 1

Met Leu Leu Leu Ala Arg Cys Leu Leu Val Leu Val Ser Ser Leu
1               5                   10                  15

Leu Val Cys Ser Gly Leu Ala Cys Gly Pro Gly Arg Gly Phe Gly Lys
                20                  25                  30

Arg Arg His Pro Lys Lys Leu Thr Pro Leu Ala Tyr Lys Gln Phe Ile
            35                  40                  45

Pro Asn Val Ala Glu Lys Thr Leu Gly Ala Ser Gly Arg Tyr Glu Gly
    50                  55                  60

Lys Ile Ser Arg Asn Ser Glu Arg Phe Lys Glu Leu Thr Pro Asn Tyr
65                  70                  75                  80

Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ala Leu Ala Ile Ser
            100                 105                 110

Val Met Asn Gln Trp Pro Gly Val Lys Leu Arg Val Thr Glu Gly Trp
        115                 120                 125

Asp Glu Asp Gly His His Ser Glu Glu Ser Leu His Tyr Glu Gly Arg
    130                 135                 140

Ala Val Asp Ile Thr Thr Ser Asp Arg Asp Arg Ser Lys Tyr Gly Met
145                 150                 155                 160

Leu Ala Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Thr Val His Leu Glu
        195                 200                 205

Gln Gly Gly Thr Lys Leu Val Lys Asp Leu Ser Pro Gly Asp Arg Val
    210                 215                 220

Leu Ala Ala Asp Asp Gln Gly Arg Leu Leu Tyr Ser Asp Phe Leu Thr
225                 230                 235                 240

Phe Leu Asp Arg Asp Asp Gly Ala Lys Lys Val Phe Tyr Val Ile Glu
                245                 250                 255

Thr Arg Glu Pro Arg Glu Arg Leu Leu Leu Thr Ala Ala His Leu Leu
            260                 265                 270

Phe Val Ala Pro His Asn Asp Ser Ala Thr Gly Glu Pro Glu Ala Ser
        275                 280                 285

Ser Gly Ser Gly Pro Pro Ser Gly Gly Ala Leu Gly Pro Arg Ala Leu
    290                 295                 300

Phe Ala Ser Arg Val Arg Pro Gly Gln Arg Val Tyr Val Val Ala Glu
305                 310                 315                 320

Arg Asp Gly Asp Arg Arg Leu Leu Pro Ala Ala Val His Ser Val Thr
                325                 330                 335

Leu Ser Glu Glu Ala Ala Gly Ala Tyr Ala Pro Leu Thr Ala Gln Gly
            340                 345                 350

Thr Ile Leu Ile Asn Arg Val Leu Ala Ser Cys Tyr Ala Val Ile Glu
        355                 360                 365

```
Glu His Ser Trp Ala His Arg Ala Phe Ala Pro Phe Arg Leu Ala His
    370                 375                 380
Ala Leu Leu Ala Ala Leu Ala Pro Ala Arg Thr Asp Arg Gly Gly Asp
385                 390                 395                 400
Ser Gly Gly Gly Asp Arg Gly Gly Gly Gly Arg Val Ala Leu Thr
                405                 410                 415
Ala Pro Gly Ala Ala Asp Ala Pro Gly Ala Gly Ala Thr Ala Gly Ile
            420                 425                 430
His Trp Tyr Ser Gln Leu Leu Tyr Gln Ile Gly Thr Trp Leu Leu Asp
        435                 440                 445
Ser Glu Ala Leu His Pro Leu Gly Met Ala Val Lys Ser Ser
    450                 455                 460
```

<210> SEQ ID NO 2
<211> LENGTH: 21
<212> TYPE: DNA
<213> ORGANISM: Artificial Sequence
<220> FEATURE:
<223> OTHER INFORMATION: Synthetic DNA

<400> SEQUENCE: 2
gggtggcccg ggtataaata g        21

<210> SEQ ID NO 3
<211> LENGTH: 20
<212> TYPE: DNA
<213> ORGANISM: Artificial Sequence
<220> FEATURE:
<223> OTHER INFORMATION: Synthetic DNA

<400> SEQUENCE: 3
ggtggaatct gccactccaa        20

<210> SEQ ID NO 4
<211> LENGTH: 33
<212> TYPE: DNA
<213> ORGANISM: Artificial Sequence
<220> FEATURE:
<223> OTHER INFORMATION: Synthetic DNA

<400> SEQUENCE: 4
gattacacta gtggcccgaa agcagaaacg aaa        33

<210> SEQ ID NO 5
<211> LENGTH: 33
<212> TYPE: DNA
<213> ORGANISM: Artificial Sequence
<220> FEATURE:
<223> OTHER INFORMATION: Synthetic DNA

<400> SEQUENCE: 5
acctgacccg ggccaagtcc actgctgggc ctg        33

<210> SEQ ID NO 6
<211> LENGTH: 20
<212> TYPE: DNA
<213> ORGANISM: Artificial Sequence
<220> FEATURE:
<223> OTHER INFORMATION: Synthetic DNA

<400> SEQUENCE: 6
cagcacatgc agtacaacgc        20

```
<210> SEQ ID NO 7
<211> LENGTH: 21
<212> TYPE: DNA
<213> ORGANISM: Artificial Sequence
<220> FEATURE:
<223> OTHER INFORMATION: Synthetic DNA

<400> SEQUENCE: 7 gtcactttc ctcccgtagc c                                              21

<210> SEQ ID NO 8
<211> LENGTH: 33
<212> TYPE: DNA
<213> ORGANISM: Artificial Sequence
<220> FEATURE:
<223> OTHER INFORMATION: Synthetic DNA

<400> SEQUENCE: 8
attatcgccg gcgcggtggc ggcgaggagg cct                                 33

<210> SEQ ID NO 9
<211> LENGTH: 32
<212> TYPE: DNA
<213> ORGANISM: Artificial Sequence
<220> FEATURE:
<223> OTHER INFORMATION: Synthetic DNA

<400> SEQUENCE: 9
atattcctga ggagaggaac cgcctgtggg ag                                  32

<210> SEQ ID NO 10
<211> LENGTH: 21
<212> TYPE: DNA
<213> ORGANISM: Artificial Sequence
<220> FEATURE:
<223> OTHER INFORMATION: Synthetic DNA

<400> SEQUENCE: 10
gggtggcccg ggtataaata g                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetic DNA

<400> SEQUENCE: 11
cctactcaga caatgcgatg c                                              21

<210> SEQ ID NO 12
<211> LENGTH: 23
<212> TYPE: DNA
<213> ORGANISM: Artificial Sequence
<220> FEATURE:
<223> OTHER INFORMATION: Synthetic DNA

<400> SEQUENCE: 12
caccggcccc accccggcgg cgg                                            23

<210> SEQ ID NO 13
<211> LENGTH: 23
<212> TYPE: DNA
<213> ORGANISM: Artificial Sequence
<220> FEATURE:
<223> OTHER INFORMATION: Synthetic DNA
```

```
<400> SEQUENCE: 13
aaacccgccg ccggggtggg gcc                                    23

<210> SEQ ID NO 14
<211> LENGTH: 22
<212> TYPE: DNA
<213> ORGANISM: Artificial Sequence
<220> FEATURE:
<223> OTHER INFORMATION: Synthetic DNA

<400> SEQUENCE: 14
gtgttcagcc aaaagaccat ct                                     22

<210> SEQ ID NO 15
<211> LENGTH: 19
<212> TYPE: DNA
<213> ORGANISM: Artificial Sequence
<220> FEATURE:
<223> OTHER INFORMATION: Synthetic DNA

<400> SEQUENCE: 15
gtcagggacg gcaaaccat                                         19

<210> SEQ ID NO 16
<211> LENGTH: 21
<212> TYPE: DNA
<213> ORGANISM: Artificial Sequence
<220> FEATURE:
<223> OTHER INFORMATION: Synthetic DNA

<400> SEQUENCE: 16
ccagagcccg atgaccttt t                                       21

<210> SEQ ID NO 17
<211> LENGTH: 20
<212> TYPE: DNA
<213> ORGANISM: Artificial Sequence
<220> FEATURE:
<223> OTHER INFORMATION: Synthetic DNA

<400> SEQUENCE: 17
cctcacagat cgcctacacc                                        20

<210> SEQ ID NO 18
<211> LENGTH: 21
<212> TYPE: DNA
<213> ORGANISM: Artificial Sequence
<220> FEATURE:
<223> OTHER INFORMATION: Synthetic DNA

<400> SEQUENCE: 18
tggcagtacc ccatgtctga a                                      21

<210> SEQ ID NO 19
<211> LENGTH: 20
<212> TYPE: DNA
<213> ORGANISM: Artificial Sequence
<220> FEATURE:
<223> OTHER INFORMATION: Synthetic DNA

<400> SEQUENCE: 19
ggccggaccc aagatgaaaa                                        20
```

<210> SEQ ID NO 20
<211> LENGTH: 21
<212> TYPE: DNA
<213> ORGANISM: Artificial Sequence
<220> FEATURE:
<223> OTHER INFORMATION: Synthetic DNA

<400> SEQUENCE: 20
atgtcgcgct ccttctatgt c                                    21

<210> SEQ ID NO 21
<211> LENGTH: 19
<212> TYPE: DNA
<213> ORGANISM: Artificial Sequence
<220> FEATURE:
<223> OTHER INFORMATION: Synthetic DNA

<400> SEQUENCE: 21
cgtgagcacg gtaaacccc                                       19

<210> SEQ ID NO 22
<211> LENGTH: 20
<212> TYPE: DNA
<213> ORGANISM: Artificial Sequence
<220> FEATURE:
<223> OTHER INFORMATION: Synthetic DNA

<400> SEQUENCE: 22
ggagcgagat ccctccaaat                                      20

<210> SEQ ID NO 23
<211> LENGTH: 19
<212> TYPE: DNA
<213> ORGANISM: Artificial Sequence
<220> FEATURE:
<223> OTHER INFORMATION: Synthetic DNA

<400> SEQUENCE: 23
ggcctgcatg agggtttct                                       19

<210> SEQ ID NO 24
<211> LENGTH: 19
<212> TYPE: DNA
<213> ORGANISM: Artificial Sequence
<220> FEATURE:
<223> OTHER INFORMATION: Synthetic DNA

<400> SEQUENCE: 24
gcgctgtagg cagaaaagg                                       19

<210> SEQ ID NO 25
<211> LENGTH: 20
<212> TYPE: DNA
<213> ORGANISM: Artificial Sequence
<220> FEATURE:
<223> OTHER INFORMATION: Synthetic DNA

<400> SEQUENCE: 25
cactgcctcc tagcttgtcc                                      20

<210> SEQ ID NO 26
<211> LENGTH: 23
<212> TYPE: DNA
<213> ORGANISM: Artificial Sequence
<220> FEATURE:
<223> OTHER INFORMATION: Synthetic DNA

```
<400> SEQUENCE: 26
catataggag aaggccgagt aga                                       23

<210> SEQ ID NO 27
<211> LENGTH: 21
<212> TYPE: DNA
<213> ORGANISM: Artificial Sequence
<220> FEATURE:
<223> OTHER INFORMATION: Synthetic DNA

<400> SEQUENCE: 27
ccaagaccgt cacaaaaagg c                                         21

<210> SEQ ID NO 28
<211> LENGTH: 21
<212> TYPE: DNA
<213> ORGANISM: Artificial Sequence
<220> FEATURE:
<223> OTHER INFORMATION: Synthetic DNA

<400> SEQUENCE: 28
ccccagctaa atctgctcag g                                         21

<210> SEQ ID NO 29
<211> LENGTH: 21
<212> TYPE: DNA
<213> ORGANISM: Artificial Sequence
<220> FEATURE:
<223> OTHER INFORMATION: Synthetic DNA

<400> SEQUENCE: 29
caagcgggat gaagaaatcc g                                         21

<210> SEQ ID NO 30
<211> LENGTH: 19
<212> TYPE: DNA
<213> ORGANISM: Artificial Sequence
<220> FEATURE:
<223> OTHER INFORMATION: Synthetic DNA

<400> SEQUENCE: 30
cgagcggatc ttggtgttg                                            19

<210> SEQ ID NO 31
<211> LENGTH: 23
<212> TYPE: DNA
<213> ORGANISM: Artificial Sequence
<220> FEATURE:
<223> OTHER INFORMATION: Synthetic DNA

<400> SEQUENCE: 31
ggctgttgtc atacttctca tgg                                       23
```

COMPOSITIONS AND METHODS FOR GENERATING OLIGODENDROCYTE PRECURSORS

CROSS-REFERENCE

This application is a national stage filing under 35 U.S.C. § 371 of PCT/US2016/055361, filed Oct. 4, 2016, which claims the benefit of U.S. Provisional Patent Application No. 62/237,441, filed Oct. 5, 2015, each of which applications is incorporated herein by reference in its entirety.

STATEMENT REGARDING FEDERALLY SPONSORED RESEARCH

This invention was made with government support under Grant No. ES020903 awarded by the National Institutes of Health. The government has certain rights in the invention.

INTRODUCTION

Human pluripotent stem cells (hPSCs) can self-renew and differentiate into every cell type of the body. hPSCs can be used as tools for disease modeling, drug screening, and cell replacement therapies. In cases where a cell replacement therapy may be a promising means to treat a degenerative disease or injury, but it is difficult to otherwise obtain a scalable and safe supply of such cells (e.g. limited donors, inaccessible cells), hPSCs represent a means to obtain these rare somatic cells.

Oligodendrocyte precursor cells (OPCs) play a vital physiological role in support of the central nervous system. OPCs are a subtype of glial cells and migrate along the developing neural tube to populate the central nervous system and then differentiate into mature and non-dividing myelinating oligodendrocytes. Oligodendrocytes provide electrical insulation to axons in the form of a myelin sheath. The myelin sheath provides for faster and higher fidelity action potential propagation. Loss or lack of OPCs is associated with loss of myelination and results in severe implications affecting neurological function.

SUMMARY

The present disclosure provides a three-dimensional (3D) culture system comprising a biocompatible polymer and a combination of factors in an amount effective to induce differentiation of oligodendrocyte precursors and/or oligodendrocytes from pluripotent stem cells. The present disclosure provides methods of generating oligodendrocyte precursors and/or oligodendrocytes using a three-dimensional culture system of the present disclosure. The present disclosure provides methods to treat neurological diseases and demyelinating diseases.

The present disclosure provides a three-dimensional culture system comprising a biocompatible polymer and a combination of factors in an amount effective to induce differentiation of oligodendrocyte precursors from pluripotent stem cells (e.g., a human pluripotent stem cell, a human embryonic stem cell, an induced pluripotent stem cell, etc.). In some cases, the three-dimensional culture system comprises a biocompatible polymer and allows the system to recapitulate more closely what happens in vivo during embryonic development, and hence enables a faster differentiation process. In some cases, the biocompatible polymer is thermoresponsive. In other cases, the combination of factors comprises an Shh signaling pathway agonist, a Wnt pathway agonist and retinoic acid. In some cases, the combination of factors further comprises a dual-SMAD inhibitor.

The present disclosure provides methods of generating oligodendrocyte precursor cells using the three-dimensional culture system. In some cases, a method of generating oligodendrocyte precursor cells comprises culturing pluripotent stem cells or pre-oligodendrocyte precursor cells in the three-dimensional culture system for a period of time. In some cases, the time required to generate oligodendrocyte precursor cells using the three-dimensional culture system is significantly shorter compared to other culture systems known in the art. Oligodendrocyte precursor cells generated from methods as provided by the present disclosure find use in many applications.

The present disclosure provides methods of screening for candidate agents that can be used in the treatment of neurological and myelination-related diseases. Such agents are candidates for further development into therapeutic agents that can be used to treat neurological and myelination-related diseases. In some cases, agents identified from screening methods of the present disclosure may be further developed into therapeutic agents that can be used to treat multiple sclerosis, leukodystrophies, or central nervous system injuries (e.g., spinal cord or traumatic brain injuries).

The present disclosure also provides methods of treatment. In some cases, the methods comprise generating oligodendrocyte precursor cells or oligodendrocytes using a three-dimensional culture system of the present disclosure, and administering the generated oligodendrocyte precursor cells or oligodendrocytes to an individual in need thereof. In some cases, a method of treatment of the present disclosure comprises implanting a three-dimensional culture system of the present disclosure, where the culture system comprises pluripotent stem cells, into a location in need of oligodendrocyte precursor cells. In other cases, a method of treatment of the present disclosure may comprise implanting a three-dimensional culture system of the present disclosure into a location that is in the vicinity of pluripotent stem cells, thereby driving differentiation of said pluripotent stem cells into oligodendrocyte precursor cells.

In a first aspect, the present disclosure provides a three-dimensional culture system comprising: a) biocompatible thermoresponsive polymer that forms a hydrogel at 37° C.; and b) a combination of factors that promote differentiation of oligodendrocyte precursors from pluripotent stem cells. In some cases, the biocompatible polymer is a poly(N-isopropylacrylamide)-based polyethylene glycol (PNI-PAAm-PEG). In some cases, the thermoresponsive polymer comprises: a N-isopropylacrylamide co-monomer; an alkyl [meth]acryl[ate/amide] co-monomer; and a PEG acrylamide co-monomer. In some cases, the thermoresponsive polymer comprises a segment described by formula (I):

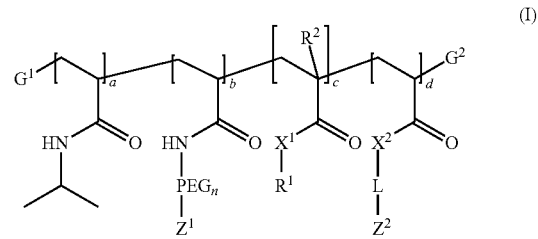

(I)

wherein:

a, b, c and d are molar fractions of the co-monomers, wherein a and c are each greater than 0;

$PEG_n$ is a polyethylglycol polymer;

$Z^1$ is an optional terminal functional group or a linked modifying agent;

$Z^2$ is a functional group or a linked modifying agent;

L is a linker;

$X^1$ and $X^2$ are each independently O or NH;

$R^1$ is a lower alkyl;

$R^2$ is H or methyl; and $G^1$ and $G^2$ are each independently selected from a polymer segment, a terminal group, a linker and a linked modifying agent.

In some cases, the thermoresponsive polymer is described by formula (II):

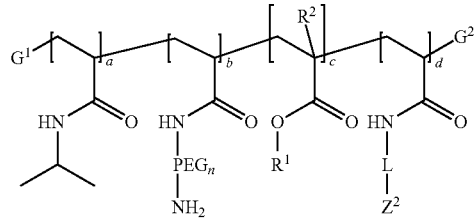
(II)

wherein $G^1$, $G^2$, $PEG_n$, $R^1$, L, $Z^2$ and a-d are as described above. In some cases, d is 0. In some cases, b>0. In some cases, a>0.8; 0.1>b>0; and 0.2>c>0. In some cases, $R^1$ is selected from the group consisting of methyl, ethyl, propyl, butyl, pentyl, isopropyl, isobutyl, isopentyl, tert-butyl, cyclopropyl, and cyclobutyl. In some cases, $Z^2$ is a chemoselective functional group. In some cases, $Z^2$ is a linked modifying agent, wherein the modifying agent is selected from a retinoic acid, an Shh signalling pathway agonist, a Wnt agonist, and a dual-Smad inhibitor.

In some cases, the thermoresponsive polymer is described by formula (III):

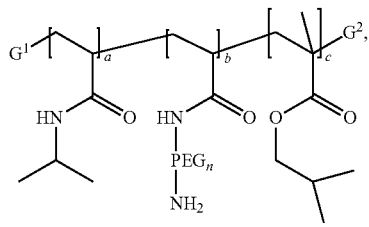
(III)

wherein $G^1$, $G^2$, $PEG_n$ and a-c are as described above. In some cases, a>0.8; 0.1>b>0; and 0.2>c>0.

In some cases, the thermoresponsive polymer is described by the formula (IV):

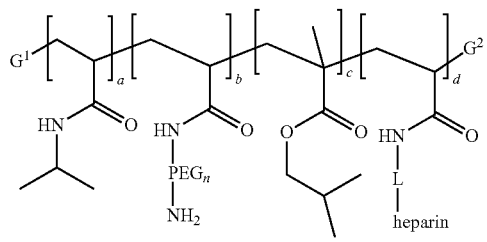
(IV)

wherein $G^1$, $G^2$, $PEG_n$, L and a-d are as described above. In some cases, $G^1$ and $G^2$ are each independently selected from a terminal group, a linker and a linked modifying agent. In some cases, $G^1$, $G^2$ or $Z^2$ comprise a linked hyaluronic acid that is linked via conjugation to the carboxylic acid group of a hyaluronic acid monomer. In some cases, $G^1$, $G^2$ or $Z^2$ comprise the following structure:

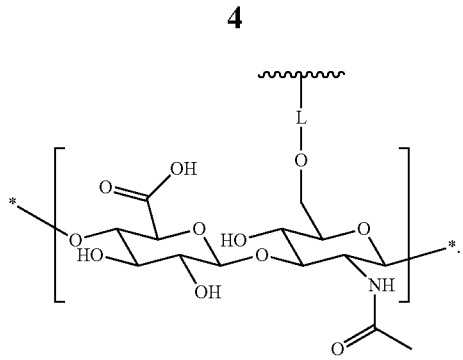

In some cases, $Z^2$ comprises the following structure:

[Structure image]

In some cases, $G^1$ and/or $G^2$ comprises the following structure:

[Structure image]

In some embodiments of the first aspect as described above, or of a culture system as described elsewhere herein, wherein the polymer has a MW of 5 to 500 kDa. In some cases, the PEG or $PEG_n$ has a MW of 2 to 100 kDa. In some cases, the culture system comprises an aqueous buffer. In some cases, the combination of factors that promote differentiation of oligodendrocyte precursors from pluripotent stem cells is selected from two or more of: i) a Sonic hedgehog (Shh) signaling pathway agonist; ii) a Wnt signaling pathway agonist; iii) retinoic acid (RA); and iv) a dual-Smad inhibitor, wherein the combination of factors is present in the system in an amount effective to induce differentiation of oligodendrocyte precursors from pluripotent stem cells in a period of time of 20 days or less. In some cases, the Shh signaling pathway agonist is 3,4-dichloro-N-

(cis-4-(methylamino)cyclohexyl)-N-(3-pyridin-4-ylbenzyl)benzo[b]thiophene-2-carboxamide, an Shh polypeptide, an Shh protein-polymer conjugate, or SAG, where SAG is a compound of the formula:

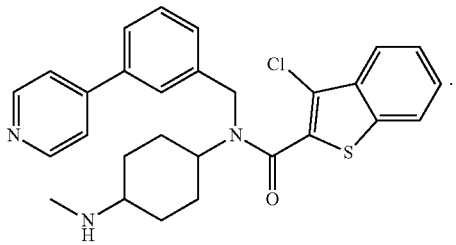 [SMILES: CNC1CCC(N(Cc2cccc(-c3ccncc3)c2)C(=O)c2sc3ccccc3c2Cl)CC1]

In some cases, the Shh signaling pathway agonist is present in a concentration of from about 0.5 µM to about 2 µM. In some cases, the Wnt agonist is CHIR99021, where CHIR99021 is a compound of the formula:

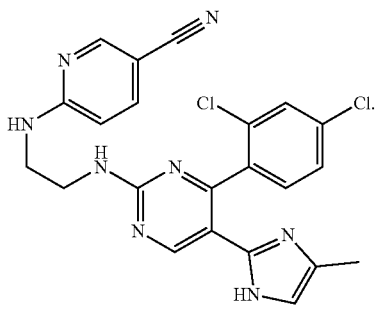 [SMILES: Cc1c[nH]c(-c2cnc(NCCNc3ccc(C#N)cn3)nc2-c2ccc(Cl)cc2Cl)n1]

In some cases, the Wnt agonist is present in a concentration of from about 1 µM to about 10 µM. In some cases, the retinoic acid is present in a concentration of from about 50 nM to about 150 nM. In some cases, the dual-SMAD inhibitor is SB431542 and/or LDN189193, wherein SB431542 is a compound of the formula:

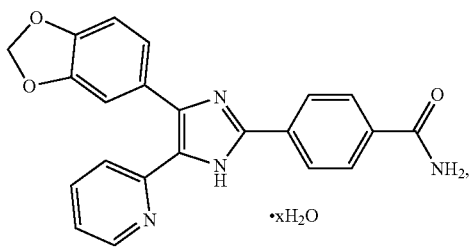 [SMILES: NC(=O)c1ccc(-c2nc(-c3ccc4c(c3)OCO4)c(-c3ccccn3)[nH]2)cc1]

and
wherein LDN189193 is a compound of the formula:

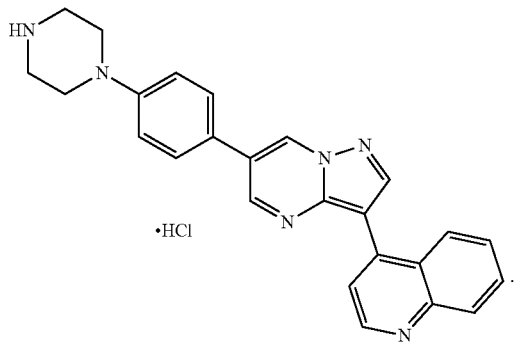 [SMILES: c1ccc2c(-c3cnn4cc(-c5ccc(N6CCNCC6)cc5)cnc34)ccnc2c1 ; Cl]

In some cases, the culture system comprises both SB431542 and LDN189193.

In some cases, the culture system comprises a pluripotent stem cell.

In a second aspect, the present disclosure provides a method of generating an oligodendrocyte precursor cell (OPC), the method comprising culturing a pluripotent stem cell or a pre-oligodendrocyte precursor cell (pre-OPC) in the culture system of the first aspect as described above, or a culture system as described elsewhere herein, for a period of from 1 day to 30 days, thereby generating an OPC. In some cases, the pluripotent stem cell is a human pluripotent stem cell. In some cases, the pre-OPC is a human pre-OPC. In some cases, the pluripotent stem cell is an induced pluripotent stem cell. In some cases, the pluripotent stem cell is a human embryonic stem cell. In some cases, the culturing is performed at a density of up to $2\times10^9$ pre-OPCs per mL hydrogel. In some cases, the OPCs express one or more differentiation markers. In some cases, the differentiation markers are Olig2 and NKX2.2. In some cases, the method further comprises inducing differentiation of the OPCs to generate oligodendrocytes. In some cases, the pluripotent stem cell or a pre-pre-OPC is culture in the culture system for a period of from 5 days to 20 days.

In a third aspect, the present disclosure provides a treatment method comprising: a) generating an oligodendrocyte precursor cell (OPC) or oligodendrocyte according to the method as described in the second aspect above, or a method as described elsewhere herein; and b) administering the generated OPC or oligodendrocyte to an individual in need thereof, thereby providing a treatment. In some cases, the treatment treats a demyelinating disease. In some cases, the demyelinating disease is multiple sclerosis. In some cases, the demyelinating disease is hypomyelinating leukodystrophy. In some cases, the treatment treats a central nervous system injury that involves inflammation and loss of myelin.

In a fourth aspect, the present disclosure provides a treatment method comprising: implanting the culture system as described in the first aspect, above, or a culture system as described elsewhere herein, in an individual in need thereof, wherein the pluripotent stem cell differentiates into an oligodendrocyte precursor cell, and wherein the OPC provides a treatment. In some cases, the treatment treats a demyelinating disease. In some cases, the demyelinating disease is multiple sclerosis. In some cases, the demyelinating disease is hypomyelinating leukodystrophy. In some cases, the treatment treats a central nervous system injury that involves inflammation and loss of myelin.

BRIEF DESCRIPTION OF THE DRAWINGS

FIG. 3A-3F depict the generation of an NKX2.2-EGFP hESC reporter line, assays that validated the design and functioning of the reporter line, and analysis of the 3D expanded hESC reporter cells.

FIG. 4A-4J depict optimization of early OPC differentiation in 3D.

FIG. 15A shows a schematic illustration of the 2 maturation strategies tested.

FIG. 19 provides a table of primers used.

FIG. 20 provides a table with the composition of the media used for OPCs and oligodendrocyte differentiations.

FIG. 21 provides a table of primary antibodies used for ICC and IHC.

FIG. 22 provides a table of primers used for qPCR.

DEFINITIONS

Figure 1:
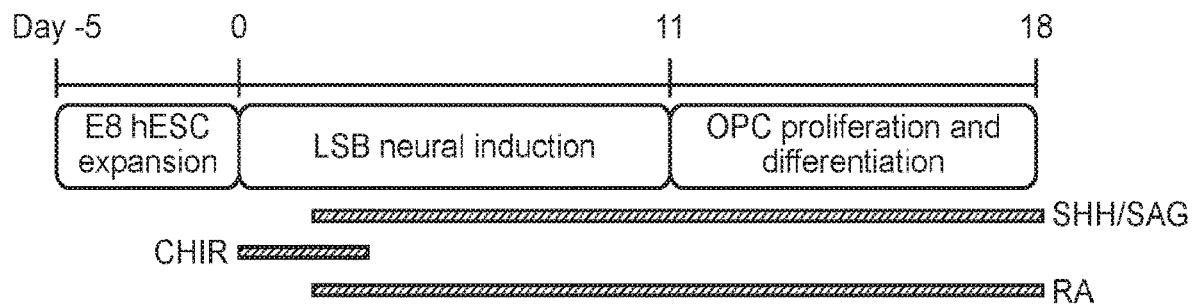
FIG. 1 depicts a schematic of the differentiation protocol for pre-oligodendrocyte precursor cell patterning from pluripotent stem cells in a PNIPAAm-PEG based culture system.

A "three-dimensional culture system," as used herein, refers to an environment that is created to allow biological cells to grow or interact with its surroundings in all three dimensions.

The term "biocompatible" as used herein, e.g., a biocompatible polymer, refers to a polymer that does not cause substantial toxic or injurious effects to an individual upon implantation. For example, an implanted biocompatible material does not induce an allergic reaction, inflammation, rejection, adverse immune response, or the like.

The term "hydrogel" as used herein refers to a network of polymer chains that are hydrophilic, sometimes found as a colloidal gel in which water is the dispersion medium.

The term "thermoresponsive" refers to a polymer that responds to temperature. For example, a thermoresponsive hydrogel is a certain state (e.g., solid) above a certain temperature, but is maintained as a liquid at a lower temperature. For example, in some cases, a thermoresponsive polymer is liquid at 4° C., and is a gel or semi-solid at 37° C.

The term "factor" as used herein refers to a biologically active factor. A factor as used in the present disclosure may be a small molecule or a peptide. As used herein, a "combination of factors" refers to a combination of biologically active factors that function together to achieve a result (e.g., differentiation of oligodendrocyte precursor cells).

An "effective amount" of a factor or combination of factors is an amount that, when in contact with target suitable cells, provides a functional effect that results in a desired outcome, e.g., differentiation of pluripotent stem cells into oligodendrocyte precursor cells. An effective amount should be readily scalable depending on the number of target suitable cells that are subject to a factor or combination of factors to obtain the desired outcome.

The terms "nucleic acid" and "polynucleotide" are used interchangeably herein and refer to a polymeric form of nucleotides of any length, either deoxyribonucleotides or ribonucleotides, or analogs thereof. Non-limiting examples of polynucleotides include linear and circular nucleic acids, messenger RNA (mRNA), cDNA, recombinant polynucleotides, vectors, probes, and primers.

The term "genetically modified" refers to a permanent or transient genetic change induced in a cell following introduction of new nucleic acid (i.e., nucleic acid exogenous to the cell). Genetic change ("modification") can be accomplished by incorporation of the new nucleic acid into the genome of the host cell, or by transient or stable maintenance of the new nucleic acid as an extrachromosomal element. Where the cell is a eukaryotic cell, a permanent genetic change can be achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, and the like.

The term "transformation" refers to a permanent or transient genetic change induced in a cell following introduction of a nucleic acid (i.e., DNA and/or RNA exogenous to the cell). Genetic change ("modification") can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel et al, *Short Protocols in Molecular Biology*, 3rd ed., Wiley & Sons, 1995.

The term "operably linked" refers to functional linkage between molecules to provide a desired function. For example, "operably linked" in the context of nucleic acids refers to a functional linkage between nucleic acids to provide a desired function such as transcription, translation, and the like, e.g., a functional linkage between a nucleic acid expression control sequence (such as a promoter, signal sequence, or array of transcription factor binding sites) and a second polynucleotide, wherein the expression control sequence affects transcription and/or translation of the second polynucleotide. "Operably linked" in the context of a polypeptide refers to a functional linkage between amino acid sequences (e.g., of different domains) to provide for a described activity of the polypeptide.

The term "recombinant" nucleic acid or "recombinant" protein refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

By "construct" or "vector" is meant a recombinant nucleic acid, generally recombinant DNA, which has been generated for the purpose of the expression and/or propagation of a nucleotide sequence(s) of interest, or is to be used in the construction of other recombinant nucleotide sequences.

The term "phenotypic marker" or "marker" as it refers to a cell refers to any observable characteristic that is indicative of a certain genotype or condition of the cell. A phenotypic marker may refer to a morphological characteristic of the cell that can be observed via a microscope, or even by the unaided (human) eye. A phenotypic marker may be a molecular marker (e.g., a cell surface polypeptide; an mRNA; etc.), where the presence or absence of the marker is indicative of the phenotype of the cell. For example, oligodendrocyte precursor cells express the phenotypic markers Olig2 and NKX2.2. Examples of other markers that are indicative of OPCs are found throughout this specification.

The terms "oligodendrocyte precursor cell" or "OPC" refers to a cell that upon differentiation, become a cell of the oligodendrocyte lineage. Such a cell expresses specific markers, e.g. Olig2, NKX2.2 and the like, and may develop characteristics of functional oligodendrocytes such as the ability to myelinate neuronal axons in vivo and in vitro. As used herein, the term "pre-oligodendrocyte precursor cell" or "pre-OPC" refers to a cell that becomes an oligodendrocyte precursor cell upon differentiation. A pre-OPC as used herein may refer to, e.g., a neural committed pluripotent stem cell, a neural committed human embryonic stem cell, and the like.

The term "pluripotent" or "pluripotency" refers to cells with the ability to give rise to progeny that can undergo differentiation, under appropriate conditions, into cell types that collectively exhibit characteristics associated with cell lineages from the three germ layers (endoderm, mesoderm, and ectoderm). A "stem cell" is a cell characterized by the ability of self-renewal through mitotic cell division and the potential to differentiate into a tissue or an organ. Among mammalian stem cells, embryonic and somatic stem cells may be distinguished. Pluripotent stem cells, which include embryonic stem cells, embryonic germ cells and induced pluripotent cells, can contribute to tissues of a prenatal, postnatal or adult organism.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," are used interchangeably herein and refer to any mammalian subject for whom diagnosis, treatment, or therapy is desired, e.g., humans, non-human primates, rodents (e.g., mice; rats), lagomorphs (e.g., rabbits), ungulates, canines, felines, etc.

As used herein, the term "linker" or "linkage" refers to a linking moiety that connects two groups and has a backbone of 100 atoms or less in length. A linker or linkage may be a covalent bond that connects two groups or a chain of between 1 and 100 atoms in length, for example of 1, 2, 3, 4, 5, 6, 8, 10, 12, 14, 16, 18 or 20 carbon atoms in length, where the linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, poly(ethylene glycol); ethers, thioethers, tertiary amines, alkyls, which may be straight or branched, e.g., methyl, ethyl, n-propyl, 1-methylethyl (isopropyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

"Alkyl" refers to monovalent saturated aliphatic hydrocarbyl groups having from 1 to 10 carbon atoms and such as 1 to 6 carbon atoms, or 1 to 5, or 1 to 4, or 1 to 3 carbon atoms. In some cases, a "lower alkyl" is an alkyl group having 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

As used herein, the terms "chemoselective functional group" and "chemoselective tag" are used interchangeably and refer to chemoselective reactive groups that selectively react with one another to form a covalent bond. Chemoselective functional groups of interest include, but are not limited to, two thiol groups, thiols and maleimide or iodoacetamide, as well as groups that can react with one another via Click chemistry, e.g., azide and alkyne groups (e.g., cyclooctyne groups). Chemoselective functional groups of interest, include, but are not limited to, thiols, alkyne, a cyclooctyne, an azide, a phosphine, a maleimide, an alkoxyamine, an aldehyde and protected versions thereof, and precursors thereof. In certain embodiments, the chemoselective functional group is a thiol.

As used, herein the lower critical solution temperature (LCST) or lower consolute temperature refers to the critical temperature below which the components of a mixture are miscible for all compositions. The word lower in the term indicates that the LCST is a lower bound to a temperature interval of partial miscibility, or miscibility for certain compositions only.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an oligodendrocyte precursor" includes a plurality of such precursors and reference to "the Wnt agonist" includes reference to one or more Wnt agonists and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a three-dimensional culture system comprising a biocompatible polymer and a combination of factors in an amount effective to induce differentiation of oligodendrocyte precursors and/or oligodendrocytes from pluripotent stem cells. The present disclosure provides methods of generating oligodendrocyte precursors and/or oligodendrocytes using a three-dimensional culture system of the present disclosure. The present disclosure provides methods to treat neurological diseases and demyelinating diseases.

Three-Dimensional Culture System

The present disclosure provides a three-dimensional culture system that provides for the differentiation of oligodendrocyte precursor cells from pluripotent stem cells. In some cases a three-dimensional culture system of the present disclosure comprises a biocompatible thermoresponsive polymer and a combination of factors that drive the differentiation of oligodendrocyte precursor cells (OPCs) from pluripotent stem cells (PSCs).

Biocompatible Polymers

The present disclosure provides a three-dimensional culture system that comprises a biocompatible polymer. In some cases the biocompatible polymer is thermoresponsive and forms a hydrogel at certain temperatures. Some thermoresponsive polymers can undergo reversible phase transition from a liquid state at lower temperatures to a solid state at higher temperatures. In some cases, a biocompatible thermoresponsive polymer of the present disclosure is a liquid at around 4° C. For example, a biocompatible thermoresponsive polymer of the present disclosure is a liquid at a temperature that is below about 25° C., below about 22° C., below about 20° C., below about 18° C., below about 16° C., below about 14° C., below about 12° C., below about 10° C., below about 8° C., below about 6° C., below about 4° C., below about 2° C., or around 0° C. In some cases, a biocompatible thermoresponsive polymer of the present disclosure is liquid at a temperature in the range of from about 2° C. to 4° C., from 4° C. to 6° C., from 2° C. to 6° C., from 6° C. to 10° C., or from 2° C. to 10° C. In some cases, a biocompatible thermoresponsive polymer of the present disclosure is a solid, semi-solid, or a gel at around 37° C. For example, in some cases, a biocompatible thermoresponsive polymer of the present disclosure is a solid, semi-solid, or a gel at a temperature of at least 30° C., at least 32° C., at least 34° C., at least 35° C., at least 36° C., at least 37° C., at least 38° C., at least 40° C., at least 42° C. In some cases, a biocompatible thermoresponsive polymer of the present disclosure is a gel at a temperature in the range of from about 34° C. to 35° C., from 35° C. to 38° C., or from 34° C. to 37° C. In some cases, a biocompatible thermoresponsive polymer of the present disclosure is at a temperature in the range of from about 2° C. to 4° C., from 4°

C. to 6° C., from 2° C. to 6° C., from 6° C. to 10° C., or from 2° C. to 10° C.; and is a gel at a temperature in the range of from about 34° C. to 35° C., from 35° C. to 38° C., or from 34° C. to 37° C. For example, in some cases, a biocompatible thermoresponsive polymer of the present disclosure is liquid at 4° C. and becomes a gel when warmed to 37° C.

In some cases, a thermoreversible polymer (e.g., a thermoreversible polymer of Formula I, Formula II, Formula III, or Formula IV) has a sol-gel transition temperature or LCST in the range of 5-35° C., such as 10-35° C., 10-30° C., 10-25° C. or 10-20° C. In some cases, a thermoreversible polymer (e.g., a thermoreversible polymer of Formula I, Formula II, Formula III, or Formula IV) has an LCST in the range of 10° C. to about 15° C.

A biocompatible thermoresponsive polymer of the present disclosure forms a three-dimensional hydrogel at certain temperatures (e.g., at 37° C., at above 30° C., etc.). Accordingly, the three-dimensionality of a biocompatible thermoresponsive polymer of the present disclosure provides a system that recapitulates closely what happens in vivo during embryonic development. For example, the three-dimensionality of a biocompatible thermoresponsive polymer of the present disclosure provides an environment similar to the natural environment cells reside in during embryonic development, and thus provides an environment for rapid cell growth, that prevents large cell aggregate formation, that protects cells from shear forces, and that has sufficient porosity for the diffusion of small molecules, nutrients and growth factors.

In some cases, a biocompatible thermoresponsive polymer of the present disclosure provides for a three-dimensional, scalable, culture system. In some cases, a biocompatible thermoresponsive polymer of the present disclosure forms a hydrogel at certain temperatures and provides for the culturing and differentiating of cells (e.g., differentiation of pluripotent stem cells to OPCs or to oligodendrocytes) with densities as high as about $1 \times 10^9$ cells/mL of hydrogel. For example, in some cases, a biocompatible thermoresponsive polymer of the present disclosure forms a hydrogel at certain temperatures and provides for the culturing and differentiating of cells (e.g., differentiation of pluripotent stem cells to OPCs or to oligodendrocytes) with densities as high as about $1 \times 10^9$ cells/mL of hydrogel, as high as about $1 \times 10^7$ cells/mL of hydrogel, as high as about $1 \times 10^6$ cells/mL of hydrogel, as high as about $1 \times 10^5$ cells/mL of hydrogel, as high as about $1 \times 10^4$ cells/mL of hydrogel, or as high as about $1 \times 10^3$ cells/mL of hydrogel. In some cases, a biocompatible thermoresponsive polymer of the present disclosure forms a hydrogel at certain temperatures and provides for the culturing and differentiating of subject cells with a cell density in the range of from about $1 \times 10^3$ cells/mL to about $5 \times 10^3$ cells/mL, from about $5 \times 10^3$ cells/mL to about $1 \times 10^4$ cells/mL, from about $1 \times 10^4$ cells/mL to about $5 \times 10^4$ cells/mL, from about $10^5$ cells/mL to about $5 \times 10^5$ cells/mL, from about $5 \times 10^5$ cells/mL to about $10^6$ cells/mL, from about $10^6$ cells/mL to about $5 \times 10^6$ cells/mL, from about $5 \times 10^6$ cells/mL to about $10^7$ cells/mL, from about $10^7$ cells/mL to about $5 \times 10^7$ cells/mL, from about $5 \times 10^7$ cells/mL to about $10^8$ cells/mL, from about $10^8$ cells/mL to about $5 \times 10^8$ cells/mL, or from about $5 \times 10^8$ cells/mL to about $10^9$ cells/mL. In some cases, a biocompatible thermoresponsive polymer of the present disclosure forms a hydrogel at certain temperatures and provides for the culturing and differentiating of subject cells with densities as high as about $1 \times 10^9$ cells/cc ($1 \times 10^9$ cells/cubic centimeter) of hydrogel. For example, in some cases, a biocompatible thermoresponsive polymer of the present disclosure forms a hydrogel at certain temperatures and provides for the culturing and differentiating of subject cells with densities as high as about $1 \times 10^9$ cells/cc of hydrogel, as high as about $1 \times 10^7$ cells/cc of hydrogel, as high as about $1 \times 10^6$ cells/cc of hydrogel, as high as about $1 \times 10^5$ cells/cc of hydrogel, as high as about $1 \times 10^4$ cells/cc of hydrogel, as high as about $1 \times 10^3$ cells/cc of hydrogel. The ability of culturing and differentiating subject cells at high density using a biocompatible thermoresponsive polymer of the present disclosure, allows for the large-scale production of subject differentiated cells.

In some cases, a biocompatible thermoresponsive polymer of the present disclosure can take any of a variety of 3-dimensional forms, or can be relatively amorphous. For example, the biocompatible thermoresponsive polymer can be in the form of a cylinder, a sphere, etc. In some cases, a biocompatible thermoresponsive polymer of the present disclosure can be shaped into a desired shape.

In some cases, a biocompatible thermoresponsive polymer of the present disclosure comprises a material that is suitable for implantation into an individual. Accordingly, in some cases, a biocompatible thermoresponsive polymer of the present disclosure will not cause substantial toxic or injurious effects once implanted into an individual.

Suitable components of the biocompatible thermoresponsive polymer include, but are not limited to, e.g., collagen; gelatin; fibrin; fibrinogen; laminin; a glycosaminoglycan; elastin; hyaluronic acid; a proteoglycan; a glycan; poly(lactic acid); poly(vinyl alcohol); poly(vinyl pyrrolidone); poly(ethylene oxide); cellulose; a cellulose derivative; starch; a starch derivative; poly(caprolactone); poly(hydroxy butyric acid); mucin; and the like.

In some cases, a biocompatible thermoresponsive polymer of the present disclosure forms a hydrogel. A suitable thermoresponsive biocompatible polymer of the present disclosure that forms a hydrogel can be a polymer of two or more monomers, e.g., a homopolymer or a heteropolymer comprising multiple monomers. A suitable thermoresponsive biocompatible polymer that forms a hydrogel can comprise hydrogel monomers that include, but are not limited to, e.g., lactic acid, glycolic acid, acrylic acid, 1-hydroxyethyl methacrylate (HEMA), ethyl methacrylate (EMA), propylene glycol methacrylate (PEMA), acrylamide (AAM), N-vinylpyrrolidone, methyl methacrylate (MMA), glycidyl methacrylate (GDMA), glycol methacrylate (GMA), ethylene glycol, fumaric acid, and the like. Common cross linking agents include tetraethylene glycol dimethacrylate (TEGDMA) and N,N'-methylenebisacrylamide. The biocompatible polymer can be homopolymeric, or can comprise co-polymers of two or more of the aforementioned polymers. In some cases, suitable a biocompatible thermoresponsive polymer includes, but are not limited to, a copolymer of poly(ethylene oxide) (PEO) and poly(propylene oxide) (PPO); Pluronic™ F-127 (a difunctional block copolymer of PEO and PPO of the nominal formula $EO_{100}$-$PO_{65}$-$EO_{100}$, where EO is ethylene oxide and PO is propylene oxide); poloxamer 407 (a tri-block copolymer consisting of a central block of poly(propylene glycol) flanked by two hydrophilic blocks of poly(ethylene glycol) (PEG)); a poly(ethylene oxide)-poly(propylene oxide)-poly(ethylene oxide) co-polymer with a nominal molecular weight of 12,500 Daltons and a PEO:PPO ratio of 2:1); a poly(N-isopropylacrylamide)-based biocompatible polymer (a PNIPAAm-based biocompatible polymer); a poly(N-isopropylacrylamide)-based polyethylene glycol biocompatible polymer (a PNIPAAm-PEG-based biocompatible polymer);

a PNIPAAm-acrylic acid co-polymer (PNIPAAm-co-AAc); poly(2-hydroxyethyl methacrylate); poly(vinyl pyrrolidone); and the like.

A biocompatible polymer of the present disclosure can further comprise one or more additional components, where suitable additional components include, e.g., growth factors; antioxidants; nutritional transporters (e.g., transferrins); a polyamine (e.g., glutathione, spermidine, etc.); small molecules; and the like.

In some cases, a biocompatible polymer suitable for use in a three-dimensional culture system or in a method of the present disclosure is a thermoreversible polymer (also referred to as a "thermosensitive polymer" or a "thermoresponsive polymer"), e.g., a thermoreversible polymer of any one of Formula I, Formula II, and Formula IV, as set out below. As used herein, the term "thermoreversible" is used to refer to a polymeric material that exhibits a drastic change in its physical property with a change in temperature. Thermoreversible polymers belong to the class of stimuli-responsive materials. In some cases, a thermoreversible polymer is distinguished from a temperature-sensitive (e.g., thermosensitive) material, which can change physical properties continuously with environmental conditions. A thermoresponsive polymer can display a miscibility gap in its temperature-composition diagram. Depending on whether the miscibility gap is found at high or low temperatures, an upper or lower critical solution temperature exists, respectively (abbreviated UCST or LCST, respectively). For example, at a temperature below the LCST, a thermoresponsive polymer can be miscible with an aqueous solution in which it dissolves. At a temperature above the LCST, the thermoresponsive polymer forms a solid, semi-solid, or gel having a three dimensional structure.

A suitable thermoreversible polymer can include a polymer including N-isopropylacrylamide co-monomer, an alkyl [meth]acryl[ate/amide] co-monomer; and a PEG acrylamide co-monomer. As used herein, the term "an alkyl [meth]acryl [ate/amide] co-monomer" refers to a co-monomer that is an alkyl acrylate, an alkyl methacrylate, an alkyl acrylamide or an alkyl methacrylamide. In some instances, the alkyl [meth]acryl[ate/amide] co-monomer is an isobutyl methacrylate co-monomer.

As used herein, the term PEG acrylamide co-monomer refers to an N-alkyl acrylamide further substituted on the alkyl sidechain with a polyethylene glycol (PEG) or modified polyethylene glycol. In some cases, a PEG polymeric group includes water-soluble repeat units comprising an ethylene oxide of the formula —(CH$_2$—CH$_2$—O)— or —(O—CH$_2$—CH$_2$)—. The number of such water-soluble repeat units can vary significantly, with the number of such units being from 2 to 500, 2 to 400, 2 to 300, 2 to 200, 2 to 100, for example from 2 to 50. A modified PEG can include any convenient terminal modifications, such as substitution or modification with a linked functional group such as an amine, a thiol or a carboxylic acid, e.g., capable of conjugation with a modifying agent of interest.

In some embodiments, the thermoreversible polymer further comprises a modifying acryl[ate/amide] co-monomer comprising a linked functional group or a linked modifying agent. As used herein, by modifying acryl[ate/amide] co-monomer is meant a substituted alkyl acrylate or a substituted N-alkyl acrylamide co-monomer, which can be substituted with an optional linker terminated with a functional group and/or a linked modifying agent. In certain embodiments, the thermoreversible polymer lacks a PEG acrylamide co-monomer.

In some embodiments, the thermoreversible polymer comprises a polymeric segment described by formula (I):

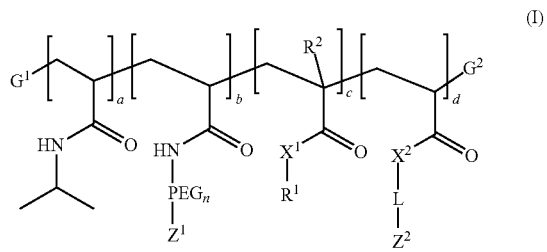

wherein:

a, b, c and d are molar fractions of the co-monomers (e.g., in some cases, a and c are each greater than 0);

PEG$_n$ is a polyethylglycol polymer;

Z$^1$ is an optional terminal functional group or a linked modifying agent;

Z$^2$ is a functional group or a linked modifying agent;

L is a linker;

X$^1$ and X$^2$ are each independently O or NH;

R$^1$ is an alkyl or a substituted alkyl (e.g., a lower alkyl or a substituted lower alkyl);

R$^2$ is H or methyl; and

G$^1$ and G$^2$ are each independently selected from a polymer segment, a terminal group, a linker and a linked modifying agent (e.g., a hyaluronic acid).

As used here, the term "modifying agent" refers to any convenient agent that provides for a desirable property of interest (e.g., a desirable physical and/or biological property) and which is capable of conjugation to the thermoreversible polymer, e.g., via a chemoselective functional group on a sidechain linker or terminal of the polymer. Such an agent may belong to the class of small molecule, protein, peptide, sugar, polynucleotide, etc. Modifying agents of interest include, but are not limited to, a ligand, a substrate, an enzyme, a pharmaceutical agent (e.g., a chemotherapeutic agent), a plasmid, a polynucleotide, a bioactive peptide, an antibody, a biomarker, a bio-sensor, a catalyst, an element, a cell targeting agent, small drug molecules, fluorescent/radioactive/optical imaging agents, peptides/proteins/enzymes, nucleic acids (siRNA/RNA/DNA/etc.), metal based compounds/catalysts, site-specific cellular targeting agents (compounds/ligands/antibodies/etc.) and smart adjuvants, gene therapy vectors. In certain embodiments, the modifying agent is selected from a heparin, a hyaluronic acid, a specific binding member, a peptide, a nucleic acid, gelatin, fibronectin, collagen, laminin, bFGF, EGF, insulin, progesterone, glucose, thymosin beta-4, SHH, Noggin, Activin, TGFb3, FGF8, BDNF, GDNF, NT3, PDGF-AA and IGF-1. In certain instances, the modifying agent is a cytokine, a BMP family member (e.g., TGFbeta or activin), a neutrophin (e.g., NT3 or BDNF) or a hedgehog protein (e.g., SHH). In certain cases, the modifying agent is one or more of a Wnt agonist, an Shh signaling pathway agonist, retinoic acid, and a dual-Smad inhibitor.

Any convenient methods may be utilized in conjugating a modifying agent to a thermoreversible polymer. Conjugation methods and chemistries of interest include, but are not limited to, those described by Greg Hermanson in Bioconjugate Techniques (Third edition) 2013, Academic Press. In certain embodiments, the modifying agent is a protein. In certain embodiments, the modifying agent is a peptide. In certain embodiments, the modifying agent is peptidic and can be conjugated to the thermoreversible polymer (e.g., via a terminal and/or a sidechain functional group) by covalent attachment to the N-terminal or C-terminal or the peptidic agent, or covalent attachment to an amino acid sidechain (e.g., an amino, thiol, hydroxyl, carboxylic acid or phenol-containing amino acid sidechain group, or a derivative thereof). In certain embodiments, the modifying agent is a heparin. In certain embodiments, the heparin modifying agent in linked via a vinvylsulfone/thiol linkage. In certain embodiments, the modifying agent is a heparin. In certain instances, the heparin can be linked to the subject polymers via conjugation to a carboxylic acid group of the heparin. For example, FIG. 21 depicts exemplary methods of preparing a heparin-thiol derivative and a hyaluronic acid-vinyl sulfone derivative that finds use in conjugation to the subject thermoreversible polymer. In certain embodiments, heparin can be attached via an amine group of the thermoreversible polymer. In certain embodiments, two or more modifying agents (e.g., a heparin and a hyaluronic acid) may be linked to each other in addition to a thermoreversible polymer.

In some embodiments of formula (I), b is 0. In some embodiments of formula (I), b>0. In some embodiments of formula (I), b<0.5. In some embodiments of formula (I), b<0.4. In some embodiments of formula (I), b<0.3. In some embodiments of formula (I), b<0.2. In some embodiments of formula (I), b<0.1. In some embodiments of formula (I), 0<b<0.1. In some embodiments of formula (I), 0<b<0.05. In some embodiments of formula (I), 0<b<0.02.

In some embodiments of formula (I), d is 0. In some embodiments of formula (I), d>0. In some embodiments of formula (I), d<0.5. In some embodiments of formula (I), d<0.4. In some embodiments of formula (I), d<0.3. In some embodiments of formula (I), d<0.2. In some embodiments of formula (I), d<0.1. In some embodiments of formula (I), 0<d<0.1. In some embodiments of formula (I), 0<d<0.05.

In some embodiments of formula (I), a>0.3. In some embodiments of formula (I), a>0.4. In some embodiments of formula (I), a>0.5. In some embodiments of formula (I), a>0.6. In some embodiments of formula (I), a>0.7. In some embodiments of formula (I), a>0.8. In some embodiments of formula (I), a>0.9.

In some embodiments of formula (I), c>0.1. In some embodiments of formula (I), c>0.2. In some embodiments of formula (I), c>0.3. In some embodiments of formula (I), c<0.3. In some embodiments of formula (I), c<0.2. In some embodiments of formula (I), 0<c<0.2. In some embodiments of formula (I), 0<c<0.15.

In some embodiments of formula (I), a>0.9, 0<b<0.02, 0<c<0.2 and 0<d<0.05.

In some embodiments of formula (I), a>0.95. In some embodiments of formula (I), 0<b<0.01. In some embodiments of formula (I), 0<c<0.1. In some embodiments of formula (I), 0<d<0.03. In some embodiments of formula (I), a>0.95, 0<b<0.01, 0<c<0.1 and 0<d<0.03.

In some embodiments of formula (I), a>0.95, 0<b<0.01, 0<c<0.07 and 0<d<0.02. In some embodiments of formula (I), a>0.95. In some embodiments of formula (I), 0<b<0.01. In some embodiments of formula (I), 0<c<0.07. In some embodiments of formula (I), 0<d<0.02.

Any convenient poly(ethylglycol) (PEG) polymeric groups may be utilized as a sidechain in the thermoreversible polymers of Formula (I). In some embodiments of formula (I), PEGn is a polyethylglycol polymer having a MW of 2 kDa or greater, such as 2 kDa to 100 kDa, or 2 kD to 10 kDa, or 3 kDa to 10 kDa, such as 3400 Da. The PEGn group can be modified with any convenient groups, including terminal modifications. In some instances, the PEGn group is modified with a terminal group $Z^1$. In some embodiments, PEGn includes a terminal carboxylic acid. In some embodiments, PEGn includes a terminal amine group. In some embodiments, $Z^1$ is a linked modifying agent (e.g., as described herein).

Any convenient chemoselective functional groups capable of conjugation with a compatible functional group on another moiety of interest may find use as terminal group $Z^2$ in the subject a modifying acryl[ate/amide] co-monomer. In some embodiments, $Z^2$ is a functional group selected from an amino, a thiol, a carboxylic acid, a maleimide, a vinyl sulfone, a haloacetyl, an azide, an alkyne (e.g., a cyclooctyne), and protected versions thereof. In some embodiments of formula (I), $Z^2$ is a thiol. In some embodiments of formula (I), $Z^2$ is an azide. In some embodiments of formula (I), $Z^2$ is a maleimide. A variety of methods and reagents may find use in conjugating a modifying agent of interest to the terminal of a PEGn sidechain group. In some embodiments, $Z^2$ is a linked modifying agent (e.g., as described herein). In some embodiments, heparin can be conjugated to an amine group of the PEG side chain in the thermoreversible polymer.

Any convenient linkers may be utilized in a thermoreversible polymer as described above (e.g., a thermoreversible polymer of Formula I). In certain embodiments, the linker (L) includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol. Linkers of interest include, but are not limited to, units of polymers such as polyethylene glycols, polyethylenes and polyacrylates, amino acid residue(s), carbohydrate-based polymers or carbohydrate residues and derivatives thereof, polynucleotides, alkyl groups, aryl groups, heterocycle groups, cleavable linker groups, combinations thereof, and substituted versions thereof.

In some embodiments, the linker includes a cleavable moiety (e.g., a chemically cleavable moiety, an enzymatically cleavable moiety (such as, but not limited to, a protease cleavable moiety, a glucuronidase cleavable moiety, a beta-lactamase cleavable moiety, etc.), a photocleavable moiety, and the like. In certain embodiments, the cleavable moiety is a para-amino-benzyloxycarbonyl group, a meta-amino-benzyloxycarbonyl group, a para-amino-benzyloxy group, a meta-amino-benzyloxy group, para-aminobenzyl, an acetal group, a disulfide, a hydrazine, a protease-cleavable moiety, a glucuronidase cleavable moiety, a beta-lactamase cleavable moiety, or an ester.

In some embodiments of formula (I), $R^1$ is a lower alkyl or a substituted lower alkyl. In some embodiments of formula (I), $R^1$ is a lower alkyl selected from the group consisting of methyl, ethyl, propyl, butyl, pentyl, isopropyl, isobutyl, isopentyl, tert-butyl, cyclopropyl, and cyclobutyl. In certain embodiments, $R^1$ is methyl. In certain embodiments, $R^1$ is ethyl. In certain embodiments, $R^1$ is propyl. In certain embodiments, $R^1$ is butyl. In certain embodiments, $R^1$ is pentyl. In certain embodiments, $R^1$ is isopropyl. In certain embodiments, $R^1$ is isobutyl. In certain embodiments, $R^1$ is isopentyl. In certain embodiments, $R^1$ is tert-butyl. In certain embodiments, $R^1$ is cyclopropyl. In certain embodiments, $R^1$ is cyclobutyl.

In some embodiments of formula (I), $R^2$ is H. In some embodiments of formula (I), $R^2$ is methyl.

In some embodiments of formula (I), $G^1$ and/or $G^2$ are each independently a further polymer segment, such as a polyacrylic acid or polyacrylamide polymer. In certain cases of formula (I), $G^1$ and/or $G^2$ are each independently a terminal group, e.g., H, an alkyl or a substituted alkyl. In certain cases, the terminal groups are groups which are produced as a result of any convenient method of polymerization of the subject co-monomers described herein. In some embodiments of formula (I), $G^1$ and/or $G^2$ comprise a linker that may include a chemoselective functional group. In some embodiments of formula (I), $G^1$ and/or $G^2$ comprise a linked modifying agent (e.g., as described herein). Any convenient methods of derivatizing or modifying polymers may be utilized to provide for installation of a $G^1$ and/or $G^2$ group of interest at the terminals of the subject polymers. In certain cases, $G^1$ and/or $G^2$ group comprises a linked modifying agent (e.g., a hyaluronic acid).

In some embodiments, the thermoreversible polymer comprises a polymeric segment described by formula (II):

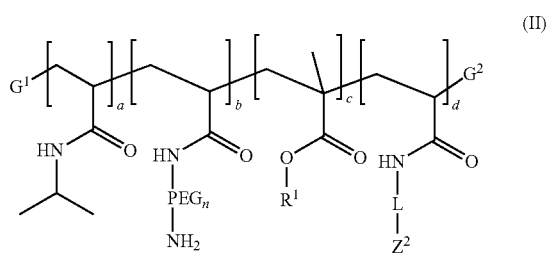

wherein $G^1$, $G^2$, $PEG_n$, $R^1$, L, $Z^2$ and a-d are as described for formula (I).

In some embodiments, the thermoreversible polymer is described by formula (I) or (II).

In some embodiments of formula (II), d is 0. In some embodiments of formula (II), a>0.8. In some embodiments of formula (II), 0.1>b>0. In some embodiments of formula (II), c<0.2. In some embodiments of formula (II), a>0.8; 0.1>b>0 and c<0.2.

In some embodiments of formula (II), b>0. In some embodiments of formula (II), b<0.5. In some embodiments of formula (II), b<0.4. In some embodiments of formula (II), b<0.3. In some embodiments of formula (II), b<0.2. In some embodiments of formula (II), b<0.1. In some embodiments of formula (II), 0<b<0.1. In some embodiments of formula (II), 0<b<0.05. In some embodiments of formula (II), 0<b<0.02.

In some embodiments of formula (II), d is 0. In some embodiments of formula (II), d>0. In some embodiments of formula (II), d<0.5. In some embodiments of formula (II), d<0.4. In some embodiments of formula (II), d<0.3. In some embodiments of formula (I), d<0.2. In some embodiments of formula (II), d<0.1. In some embodiments of formula (II), 0<d<0.1. In some embodiments of formula (II), 0<d<0.05.

In some embodiments of formula (II), a>0.3. In some embodiments of formula (II), a>0.4. In some embodiments of formula (II), a>0.5. In some embodiments of formula (II), a>0.6. In some embodiments of formula (II), a>0.7. In some embodiments of formula (I), a>0.8. In some embodiments of formula (II), a>0.9.

In some embodiments of formula (II), c>0.1. In some embodiments of formula (II), c>0.2. In some embodiments of formula (II), c>0.3. In some embodiments of formula (I), c<0.3. In some embodiments of formula (II), c<0.2. In some embodiments of formula (I), 0<c<0.2. In some embodiments of formula (II), 0<c<0.15.

In some embodiments of formula (II), a>0.9, 0<b<0.02, 0<c<0.2 and 0<d<0.05.

In some embodiments of formula (II), $R^1$ is a lower alkyl or a substituted lower alkyl. In some embodiments of formula (II), $R^1$ is a lower alkyl selected from the group consisting of methyl, ethyl, propyl, butyl, pentyl, isopropyl, isobutyl, isopentyl, tert-butyl, cyclopropyl, and cyclobutyl. In certain embodiments, $R^1$ is methyl. In certain embodiments, $R^1$ is ethyl. In certain embodiments, $R^1$ is propyl. In certain embodiments, $R^1$ is butyl. In certain embodiments, $R^1$ is pentyl. In certain embodiments, $R^1$ is isopropyl. In certain embodiments, $R^1$ is isobutyl. In certain embodiments, $R^1$ is isopentyl. In certain embodiments, $R^1$ is tert-butyl. In certain embodiments, $R^1$ is cyclopropyl. In certain embodiments, $R^1$ is cyclobutyl.

In some embodiments of formula (II), $Z^2$ is a functional group selected from an amino, a thiol, a carboxylic acid, a maleimide, a vinyl sulfone, a haloacetyl, an azide, an alkyne (e.g., a cyclooctyne), and protected versions thereof. In some embodiments of formula (II), $Z^2$ is a thiol. In some embodiments of formula (II), $Z^2$ is an azide. In some embodiments of formula (II), $Z^2$ is a maleimide. In some embodiments of formula (II), $Z^2$ is a linked modifying agent (e.g., as described herein). In certain instances of formula (I) or (II), $Z^2$ is a linked modifying agent selected from a heparin, a hyaluronic acid, a specific binding member, a peptide, a nucleic acid, gelatin, fibronectin, collagen, laminin, basic fibroblast growth factor (bFGF), epidermal growth factor (EGF), insulin, progesterone, glucose, a stromal cell-derived factor (SDF) (e.g., SDF-1), thymosin beta-4, a sonic hedgehog (SHH) polypeptide, Noggin, Activin, a transforming growth factor (TGF) (e.g., TGFb3), a fibroblast growth factor (FGF) (e.g., FGF8), brain-derived neurotrophic factor (BDNF), glial cell-derived neurotrophic factor (GDNF), a neutrophin (NT) (e.g., NT3), a platelet-derived growth factor (PDGF) (e.g., PDGF-AA), and insulin-like growth factor (IGF) (e.g., IGF-1). In certain instances of formula (I) or (II), $Z^2$ is a linked modifying agent that is a cytokine, a bone morphogenetic protein (BMP) family member (e.g., TGF-beta or activin), a neutrophin (e.g., NT3 or BDNF), a Wnt polypeptide, a Dkk polypeptide, or a hedgehog protein (e.g., SHH).

In some embodiments, the thermoreversible polymer comprises a polymeric segment described by formula (III):

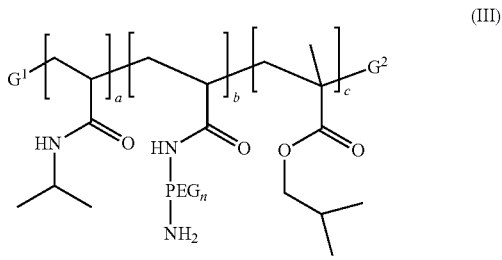

wherein $G^1$, $G^2$, $PEG_n$ and a-c are as described in formulae (I) and (II).

In some embodiments of formula (III), a>0.8. In some embodiments of formula (III), a>0.9. In some embodiments of formula (III), 0.1>b>0. In some embodiments of formula (III), 0.02>b>0. In some embodiments of formula (III), $0.2>c>0$. In some embodiments of formula (III), $0.15>c>0$. In some embodiments of formula (III), $a>0.9$; $0.02>b>0$ and $0.15>c>0$. In some embodiments of formula (III), $a>0.8$; $0.1>b>0$ and $0.2>c>0$.

In some embodiments of formula (III), $b>0$. In some embodiments of formula (III), $b<0.5$. In some embodiments of formula (III), $b<0.4$. In some embodiments of formula (III), $b<0.3$. In some embodiments of formula (III), $b<0.2$. In some embodiments of formula (III), $b<0.1$.

In some embodiments of formula (III), $a>0.3$. In some embodiments of formula (III), $a>0.4$. In some embodiments of formula (III), $a>0.5$. In some embodiments of formula (III), $a>0.6$. In some embodiments of formula (III), $a>0.7$.

In some embodiments of formula (III), $c<0.1$. In some embodiments of formula (III), $c<0.2$. In some embodiments of formula (III), $c<0.3$. In some embodiments of formula (III), $c<0.4$. In some embodiments of formula (III), $c<0.5$.

In some embodiments of formula (III), $PEG_n$ is a polyethylglycol polymer having a MW of 3 kDa or greater, such as 3 kDa to 100 kDa or 3 kD to 10 kDa, such as 3400 Da.

In some embodiments, the thermoreversible polymer comprises a polymeric segment described by formula (IV):

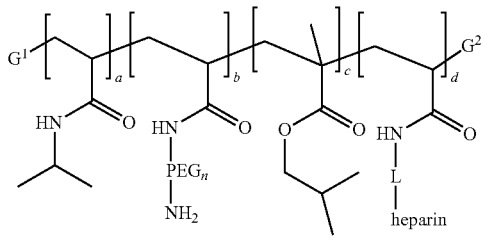

(IV)

wherein $G^1$, $G^2$, $PEG_n$, L and a-d are as described in formula (I)-(III). In some embodiments, the thermoreversible polymer is described by formula (IV).

In certain embodiments of any one of formulae (I)-(IV), $G^1$ and $G^2$ are each independently selected from a terminal group, a linker and a linked modifying agent.

The Subject

In certain embodiments of any one of formulae (I)-(IV), $G^1$, $G^2$ and/or $Z^2$ comprise the following structure:

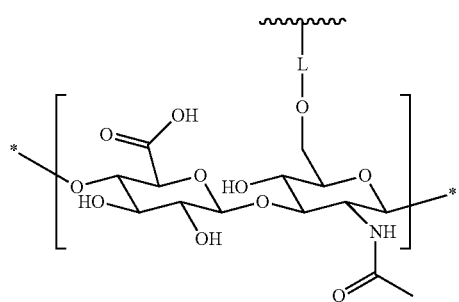

where the brackets and "*" represent that the monomer structure depicted can be a polymeric hyaluronic acid of any convenient number of monomeric units; and L is a linker. In certain instances, the subject thermoreversible polymers include a linked hyaluronic acid (e.g., linked via a terminal or a sidechain linker). In certain instances, conjugation to a linked hyaluronic acid is achieved using thiol/vinyl sulfone, thiol/maleimide, thiol/iodacetamide thiol/haloacetyl or azide/alkyne conjugation chemistry. In certain instances, conjugation to a linked hyaluronic acid is achieved using α-halocarbonyls, Michael acceptors, β-haloethylamines, or any α,β-unsaturated systems. The hyaluronic acid itself may include a variety of conjugation sites to a variety of polymers of interest. In certain cases, the hyaluronic acid itself includes a plurality of linkages to one or more moieties of interest, including one or more of the subject thermoreversible polymers. In certain instances, the thermoreversible polymer includes multiple linkages to a hyaluronic acid of interest.

The linked hyaluronic acid can be of any convenient molecular weight. In some embodiments, the linked hyaluronic acid itself has a MW of 100 kDa or more, such as 200 kDa or more, 300 kDa or more, 400 kDa or more, 500 kDa or more, 600 kDa or more, 700 kDa or more, 800 kDa or more, 900 kDa or more, 1 MDa or more, or even more. In some embodiments, the linked hyaluronic acid itself has a MW of 100 kDa to 1 MDa, such as 200 kDa to 1 MDa, 300 kDa to 1 MDa, 400 kDa to 1 MDa, or 500 kDa to 1 MDa.

In certain instances, the ratio of hyaluronic acid to thermoreversible polymer in the resulting conjugate structure may be in the range of 1:10 to 1:1.25 by weight, such as about 1:10, about 1:5, about 1:2.5 or about 1:1.25.

In certain embodiments of formulae (I)-(II), $Z^2$ comprises the following structure:

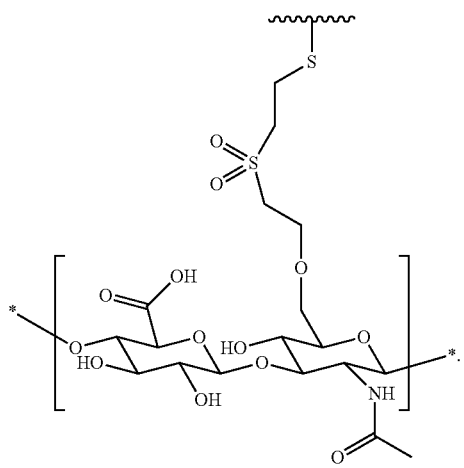

In certain embodiments of formulae (I)-(IV), $G^1$ and/or $G^2$ comprise the following structure:

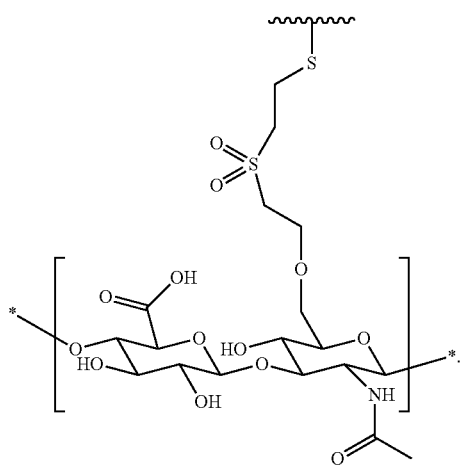

The thermoreversible polymers may have any convenient MW. In certain embodiments, the thermoreversible polymer has a MW of 500 kDa or less, such as 400 kDa or less, 300 kDa or less, 250 kDa or less, 200 kDa or less, 150 kDa or less, 100 kDa or less, 90 kDa or less, 80 kDa or less, 70 kDa or less, 60 kDa or less, or even 50 kDa or less. In certain embodiments, the thermoreversible polymer has a MW in the range or 50 kDa to 300 kDa, such as 50 kDa to 250 kDa, 50 kDa to 200 kDa, 50 kDa to 150 kDa, or 50 kDa to 100 kDa. In certain embodiments, the thermoreversible polymer has a MW of 5 kDa or more. In certain embodiments, the thermoreversible polymer has a MW of 5 kDa to 500 kDa.

In some embodiments, the thermoreversible polymer has a loss modulus when in solid or gel form of 100 Pa or more, such as 200 Pa or more, 300 Pa or more, 400 Pa or more, 500 Pa or more, 600 Pa or more, 700 Pa or more, 800 Pa or more, 900 Pa or more, 1000 Pa or more, 2000 Pa or more, 3000 Pa or more, 4000 Pa or more, 5000 Pa or more, or even more. In certain instances, the loss modulus is measured at 37° C.

In some embodiments, the thermoreversible polymer has a storage modulus when in solid or gel form of 50 Pa or more, 100 Pa or more, such as 200 Pa or more, 300 Pa or more, 400 Pa or more, 500 Pa or more, 600 Pa or more, 700 Pa or more, 800 Pa or more, 900 Pa or more, 1000 Pa or more, 2000 Pa or more, 3000 Pa or more, 4000 Pa or more, 5000 Pa or more, or even more. In certain instances, the storage modulus is measured at 37° C. In certain instances, increasing the molecular weight of hyaluronic acid increases the storage modulus of the thermoreversible polymer. In certain instances, increasing the molecular weight of PEG for copolymers containing isobutyl methacrylate and butyl methacrylate increases the storage modulus of the thermoreversible polymer. In certain instances, increasing the polymer concentration increases the storage modulus of the thermoreversible polymer. In certain instances, increasing the alkyl chain of between methyl, ethyl, and isobutyl methacrylate increases the storage modulus of the thermoreversible polymer.

In some cases, a three-dimensional culture system of the present disclosure can two or more different thermoreversible polymers. In some embodiments, the composition includes a mixture of a low MW thermoreversible polymer (e.g., having a MW of 100 kDa or less, such as 75 kDa or less, or 50 kDa or less) and a high MW thermoreversible polymer (e.g., having a MW of 100 kDa or more, such as 200 kDa or more, 300 kDa or more, 500 kDa or more, or even more).

In some cases, three-dimensional culture system comprises a thermoreversible polymer (e.g., a thermoreversible polymer of Formula I, Formula II, Formula III, and Formula IV) and an aqueous solution. A thermoreversible polymer (e.g., a thermoreversible polymer of Formula I, Formula II, Formula III, and Formula IV) and an aqueous solution is also referred to herein as a "hydrogel composition." When the hydrogel composition is below its sol-gel transition temperature, the composition can be a homogeneous solution, such that any cells that are present in the solution may be easily removed (e.g., by centrifugation). When the hydrogel composition is above its sol-gel transition temperature, the thermoreversible polymer provides a three-dimensional matrix that finds use in the incubation, growth and/or differentiation of cells of interest.

Any convenient buffered aqueous solutions that find use in the incubation and/or differentiation of cells of interest may be utilized in the hydrogel composition. The buffered aqueous solution may include any convenient components of interest.

In some instances, the hydrogel composition further includes cells of interest (e.g., as described herein). In some cases, the hydrogel composition comprises pluripotent stem cells. In certain embodiments, the hydrogel composition includes stem cells selected from the group consisting of (a) adult stem cells derived from bone marrow, adipose tissues, umbilical tissues, or placenta; (b) neural stem cells; (c) embryonic stem cells; and d) induced pluripotent stem cells. The stem cells can be human in origin, or can originate from a non-human source (e.g., rodents such as mice and rats; porcines; non-human primates; etc.). In some cases, the stem cells can be generated by implanting a donor nucleus from a somatic cell into an enucleated oocyte.

In certain instances, the thermoreversible polymer is a solid, semi-solid, or gel at 20° C. or more, such as 21° C. or more, 22° C. or more, 23° C. or more, 24° C. or more, 25° C. or more, 26° C. or more, 27° C. or more, 28° C. or more, 29° C. or more, 30° C. or more, 31° C. or more, 32° C. or more, 33° C. or more, 34° C. or more, 35° C. or more, 36° C. or more, or even more. In certain embodiments, the thermoreversible polymer is a solid at 37° C.

In certain instances, the thermoreversible polymer (e.g., a thermoreversible polymer of Formula I, Formula II, Formula III, or Formula IV) is a solid, semi-solid, or gel at 10° C. or more, or 15° or more. In certain instances, the thermoreversible polymer (e.g., a thermoreversible polymer of Formula I, Formula II, Formula III, or Formula IV) is a solid, semi-solid, or gel at a temperature of from 10° C. to 15° C., from 15° C. to 20° C., or 20° C. to 25° C. In some cases, the thermoreversible polymer (e.g., a thermoreversible polymer of Formula I, Formula II, Formula III, or Formula IV) is a solid, semi-solid, or gel at a temperature of from 10° C. to 15° C.

In some embodiments, the thermoreversible polymer is a liquid at 30° C. or less, such as 25° C. or less, 20° C. or less, 18° C. or less, 16° C. or less, 14° C. or less, 12° C. or less, 10° C. or less, 8° C. or less, 6° C. or less, or 4° C. or less. In certain embodiments, the thermoreversible polymer is a liquid at less than 20° C. In certain embodiments, the thermoreversible polymer is a liquid at 4° C.

In some cases, a thermoreversible polymer (e.g., a thermoreversible polymer of Formula I, Formula II, Formula III, or Formula IV) has a sol-gel transition temperature or LCST in the range of 5-35° C., such as 10-35° C., 10-30° C., 10-25° C. or 10-20° C. In some cases, a thermoreversible polymer (e.g., a thermoreversible polymer of Formula I, Formula II, Formula III, or Formula IV) has an LCST in the range of 10° C. to about 15° C.

A thermoreversible polymer (e.g., a thermoreversible polymer of Formula I, Formula II, Formula III, or Formula IV) can be prepared using any convenient methods. A variety of polymerization methods may be utilized in preparing a base polymeric material, e.g., including polyacrylate, polyacrylamide and mixtures thereof. A variety of derivatization methods may be utilized to introduce any convenient functionality into the subject base polymeric materials. A variety of chemoselective conjugation chemistries, linkers, functional groups and modifying agents may be utilized in the preparation of further derivatives and conjugates of the subject base polymeric materials and derivatives thereof.

Differentiation Factors

A three-dimensional culture system of the present disclosure comprises a biocompatible thermoresponsive polymer; and one or more factors that support growth and/or differentiation of a cell (e.g., a pluripotent stem cell; an OPC) contained within the three-dimensional culture system. In some cases, a three-dimensional culture system of the present disclosure comprises a biocompatible polymer; and a combination of two or more factors that support growth and/or differentiation of a cell contained within the three-dimensional culture system. In some cases, the two or more factors drive the differentiation of oligodendrocyte precursor cells (OPCs) from pluripotent stem cells (PSCs). Because the three-dimensionality of a biocompatible thermoresponsive polymer of the present disclosure provides a system that recapitulates closely what happens in vivo during embryonic development, the biocompatible polymer together with the combination of factors provides an environment similar to the natural environment cells reside in during embryonic development, and thus provides an environment for rapid cell growth, that prevents large cell aggregate formation, that protects cells from shear forces, and that has sufficient porosity for the diffusion of small molecules, nutrients and growth factors.

Suitable factors for inclusion in a three-dimensional culture system of the present disclosure include, but are not limited to, a Sonic hedgehog (Shh) signaling pathway agonist, a Wnt signaling pathway agonist, retinoic acid, and a dual-SMAD inhibitor. In some cases, a three-dimensional culture system of the present disclosure comprises a thermoresponsive biocompatible polymer, and a combination of factors comprising an Shh signaling pathway agonist (e.g., SAG), a Wnt signaling pathway agonist (e.g., CHIR99021), and retinoic acid. In some cases, a three-dimensional culture system of the present disclosure comprises a thermoresponsive biocompatible polymer, and a combination of factors comprising an Shh signaling pathway agonist, a Wnt signaling pathway agonist, retinoic acid, and a dual-SMAD inhibitor. For example, a three-dimensional culture system of the present disclosure can comprise a biocompatible thermoresponsive polymer, and a combination of factors comprising SAG, CHIR99021, retinoic acid, and a dual-SMAD inhibitor such as SB431542 and/or LDN189193. In some cases, the combination of factors is present in the three-dimensional culture system in an amount effective to induce differentiation of OPCs from PSCs.

Shh Signaling Pathway Agonist

An Shh signaling pathway agonist used in combination with one or more other factors in a three-dimensional biocompatible thermoresponsive polymer of the present disclosure can be SAG, where SAG is a compound of the formula:

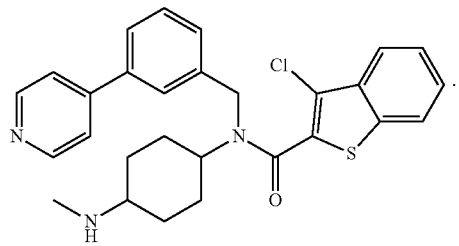 [SMILES: CNC1CCC(N(Cc2cccc(-c3ccncc3)c2)C(=O)c2sc3ccccc3c2Cl)CC1]

In some cases, other Shh signaling pathway agonists that have the same effect on the Shh signaling pathway can be used. For example, other Shh signaling pathway agonists can be used, including, but not limited to, the SAG analog 3,4-dichloro-N-(cis-4-(methylamino)cyclohexyl)-N-(3-pyridin-4-ylbenzyl)benzo[b]thiophene-2-carboxamide, SAG derivatives, an Shh polypeptide and/or variant thereof, an Shh protein-polymer conjugate, purmorphamine, purmorphamine derivatives, the synthetic non-peptidyl small molecule Hh-Ag (Frank-Kamenetsky et al., J. Biol. 2002, 1(2): 10), Hh-Ag derivatives (e.g., Hh-Ag 1.1, 1.2, 1.3, 1.4, 1.5), and the like. Shh signaling pathway agonists that may find use in the present disclosure include agonists that are derived from several sources of hedgehog protein. For example, a suitable Shh signaling pathway agonist can be a Shh polypeptide that has a hydrophobic palmitoyl group appended to the alpha-amine of the N-terminal cysteine. In some cases, the Shh signaling pathway agonist is SAG.

A suitable Shh signaling pathway agonist includes an Shh polypeptide. For example, a suitable Shh polypeptide can comprise an amino acid sequence having at least 75%, at least 80%, at least 85%, at least 90%, at least 95%, at least 98%, or 100%, amino acid sequence identity to amino acids 24-462 of the Shh amino acid set forth in SEQ ID NO:1.

In some cases, the Shh polypeptide is conjugated (e.g., linked, covalently or non-covalently) to a polymer. In some cases, the Shh polypeptide is conjugated (e.g., linked, covalently or non-covalently) to the thermoresponsive polymer present in the three-dimensional culture system. In some cases, the Shh polypeptide is conjugated (e.g., linked, covalently or non-covalently) to the polymer at a molar ratio of from about 5:1 to about 50:1.

In some cases, the Shh signaling pathway agonist is present in the three-dimensional culture system of the present disclosure in a concentration of from about 0.5 M to about 2 µM. For example, the Shh signaling pathway agonist can be present in the three-dimensional culture system of the present disclosure in a concentration of from about 0.2 µM, 0.3 µM, 0.4 µM, 0.5 µM, 0.6 µM, 0.7 µM, or 0.8 µM, to about 1.5 µM, 1.6 µM, 1.7 µM, 1.8 µM, 1.9 µM, 2 µM, 2.1 µM, 2.2 µM, 2.3 µM, 2.4 µM, or 2.5 µM.

Wnt Agonist

A Wnt signaling pathway agonist included in a three-dimensional biocompatible polymer of the present disclosure can be CHIR99021, where CHIR99021 is a compound of the formula:

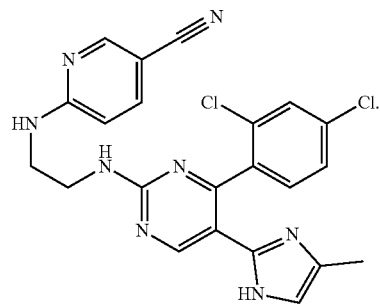 [SMILES: Cc1c[nH]c(-c2cnc(NCCNc3ccc(C#N)cn3)nc2-c2ccc(Cl)cc2Cl)n1]

In some cases, other Wnt signaling pathway agonists that have the same effect on the Wnt signaling pathway can be used. For example, other Wnt signaling pathway agonists can be used, including, but not limited to, CHIR-99021 analogs and derivatives, WAY-316606 (Bodine et al., Bone. 2009, 44(6):1063-1068), (hetero)arylpyrimidines (Gilbert et al., Bioorg. Med. Chem. Lett. 2010, 20(1):366-370), IQ-1 (Miyabashi et al., Proc. Natl. Acad. Sci. U.S.A. 2007, 104(13):5668-5673), QS11 (Zhang et al., Proc. Natl. Acad. Sci. U.S.A. 2007, 104(18):7444-7448), SB-216763 (Coghlan et al., Chem. Biol. 2000 7(10):793-803), BIO(6-bromoindirubin-3'-oxime) (Sato et al., Nat. Med. 2004, 10(1); 55-63), DCA (Pai et al., Mol. Biol. Cell. 2004 15(5):2156-2163), 2-amino-4-[3,4-(methylenedioxy)benzyl-amino]-6-

(3-methoxyphenyl)pyrimidine (Liu et al., *Angew Chem. Int. Ed. Engl.* 2005, 44(13):1987-1990), and the like.

In some cases, the Wnt signaling pathway agonist (e.g., CHIR-99021) is present in the three-dimensional culture system of the present disclosure in a concentration of from about 1 μM to about 10 μM. For example, the Wnt signaling pathway agonist can be present in the three-dimensional culture system of the present disclosure in a concentration of from about 0.5 μM, 0.6 μM, 0.7 μM, 0.8 μM, 0.9 μM, 1 μM, 1.1 μM, 1.2 μM, 1.3 μM, 1.4 μM, or 1.5 μM, to about 8 μM, 8.5 μM, 9 μM, 9.5 μM, 9.6 μM, 9.7 M, 9.8 μM, 9.9 μM, 10 μM, 10.1 μM, 10.2 μM, 10.3 μM, 10.4 μM, 10.5 μM, 11 μM, 11.5 μM, or 12 μM.

In some cases, a combination of factors that function together with a three-dimensional biocompatible polymer of the present disclosure to drive differentiation of OPCs comprises a Sonic hedgehog (Shh) signaling pathway agonist, a Wnt signaling pathway agonist, and retinoic acid.

Retinoic Acid

Retinoic acid, or a retinoic acid analog, can be included in a three-dimensional culture system of the present disclosure. Suitable retinoic acid analogs include, e.g., retinoic acid isomers [all-trans-retinoic acid (ATRA), 9-cis-retinoic acid (9CRA) and 13-cis-retinoic acid (13CRA)] and their oxidized derivatives [19-hydroxy and 19-oxo derivatives of ATRA (19-hydroxy-ATRA and 19-oxo-ATRA), 19-oxo derivative of 9CRA (19-oxo-9CRA), and 19-hydroxy derivative of 13CRA (19-hydroxy-13CRA)].

In some cases, retinoic acid (or a retinoic acid analog) is present in the three-dimensional culture system of the present disclosure in a concentration of from about 50 nM to about 150 nM. For example, retinoic acid can be present in the three-dimensional culture system of the present disclosure in a concentration of from about 20 nM, 30 nM, 40 nM, 50 nM, 60 nM, 70 nM, or 80 nM, to about 120 nM, 130 nM, 140 nM, 150 nM, 160 nM, 170 nM, 180 nM, 190 nM, or 200 nM.

Dual-SMAD Inhibitors

In some cases, a three-dimensional culture system of the present disclosure can include a factor or factors that lead to dual-SMAD inhibition. Dual-SMAD inhibition can be achieved by inhibition of type I activin receptor-like kinase receptors and type I bone morphogenetic protein (BMP) receptors, i.e., inhibition of activin and BMP signaling.

Smad2 and Smad3 are effectors in the TGFbeta/activin pathway; Smad1/5/9 are effectors for the BMP pathway. Both the TGFbeta/activin and the BMP signaling pathways can regulate the differentiation of hPSCs into non-neuroectodermal lineages. Thus, in some cases, two inhibitors—one for TGFbeta/activin and one for BMP signaling—are used. Use of two inhibitors can induce differentiation of a stem cell into a neuroectodermal lineage, which is an early step towards getting an OPC (or a neuron). Use of two inhibitors—one for TGFbeta/activin and one for BMP signaling—is termed "dual SMAD inhibition." In some cases, the inhibitors do not inhibit the Smad proteins themselves but instead inhibit other members in the pathways. For example, SB431542 inhibits TGFbeta/activin receptors (which lie upstream of Smad2/3), and LDN189193 inhibits BMP receptors (which lie upstream of Smad1/5/9). As used herein, a "dual-Smad inhibitor" refers to an agent that inhibits the TGFbeta/activin pathway or that inhibits BMP signaling.

In some cases, dual-SMAD inhibition is achieved by administering SB431542 and LDN189193 at effective concentrations. In some cases, suitable dual-SMAD inhibitors of the present disclosure can be a combination of factors such as SB431542 and LDN189193, where SB431542 is a compound of the formula:

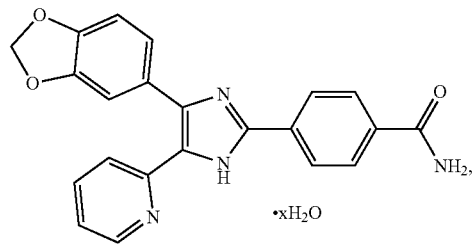 [SMILES: NC(=O)c1ccc(-c2nc(-c3ccc4c(c3)OCO4)c(-c3ccccn3)[nH]2)cc1]

and LDN189193 is a compound of the formula:

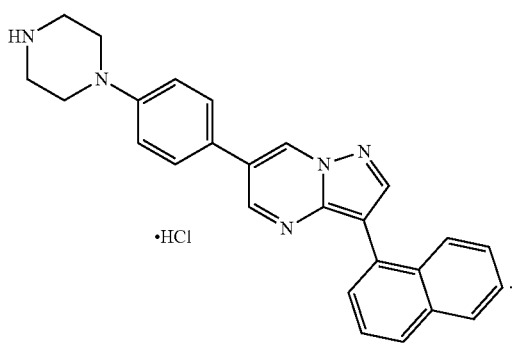 [SMILES: c1ccc2c(-c3cnn4cc(-c5ccc(N6CCNCC6)cc5)cnc34)cccc2c1 ; Cl]

In some cases, a suitable dual-SMAD inhibitor of the present disclosure is a single factor such as compound C (Zhou et al., *Stem Cells.* 2012, 28(10):1741-1750). Dual-SMAD inhibitors of the present disclosure that are a combination of factors inhibit both activin signaling (factors that may include, but are not limited to, SB431542 and derivatives, SB505124, activin-M108, inhibin, betaglycan, follistatin, follistatin-related gene (FLRG), Cripto, BAMBI (for review, see, Harrison et al., *Trends Endocrin. Metabol.* 2005, 16(2):73-78), and the like) and BMP signaling (factors that may include, but are not limited to, LDN189193 and derivatives, Noggin (Chambers et al., *Nat. Biotechnol.* 2009, 27(3):275-280), and the like). Other dual-SMAD inhibitors may include, but are not limited to, Dorsomorphin and Dorsomorphin analogs DMH1, DMH2 and LDN (Langenfeld et al., *PLoS One.* 2013, 8(4):e61256).

A combination of factors that function together with a three-dimensional biocompatible polymer of the present disclosure to drive differentiation of OPCs comprises a Sonic hedgehog (Shh) signaling pathway agonist, a Wnt signaling pathway agonist, and retinoic acid. In some cases, the combination of factors further comprises a dual-SMAD inhibitor (e.g., SB431542 and Noggin; or SB431542 and LDN189193) that is present in a three-dimensional culture system of the present disclosure, where SB431542 is present at a concentration of about from about 1 μM to about 20 μM (e.g., about 1 μM, about 5 μM, about 6 μM, about 7 μM, about 8 μM, about 9 μM, about 11 μM, about 12 μM, about 13 μM, about 14 μM, about 15 μM, 20 μM, etc.), and wherein Noggin is present at a concentration of about 500 ng/mL (e.g., about 400 ng/mL, about 450 ng/mL, about 470 ng/mL, about 480 ng/mL, about 490 ng/mL, about 510 ng/mL, about 520 ng/mL, about 530 ng/mL, about 550 ng/mL, about 600 ng/mL, etc.). In some cases, the combination of factors comprises SB431542 and LDN189193, where SB431542 is present at a concentration of about from about 1 µM to about 20 µM (e.g., about 1 µM, about 5 µM, about 6 µM, about 7 µM, about 8 µM, about 9 µM, about 11 µM, about 12 µM, about 13 µM, about 14 µM, about 15 µM, 20 µM, etc.); and where LDN189193 is present at a concentration of from about 10 nM to about 250 nM (e.g., about 10 nM, about 20 nM, about 50 nM, about 75 nM, about 100 nM, about 125 nM, about 200 nM, or about 250 nM).

Methods of Generating Oligodendrocyte Precursor Cells

The present disclosure provides methods of generating oligodendrocyte precursor cells (OPCs) and/or oligodendrocytes using a three-dimensional culture system of the present disclosure. In some cases, the method of generating OPCs comprises culturing suitable cells using a three-dimensional culture system of the present disclosure. In some cases, the method of generating OPCs comprises differentiating suitable cells by culturing the cells using a three-dimensional culture system of the present disclosure. In some cases, the method of generating OPCs comprises differentiating suitable cells (e.g., pluripotent stem cells) by culturing the cells using a three-dimensional culture system that comprises a biocompatible polymer and one factor, or a combination of factors, which are present in the system in an effective concentration to drive the differentiation of the cells into OPCs. In some cases, methods of the present disclosure include methods for the generation and/or differentiation of OPCs in a large-scale manner. In some cases, methods of the present disclosure include methods for the maturation of oligodendrocytes in a large-scale manner.

In some cases, a method of the present disclosure for generating OPCs comprises culturing stem cells in a three-dimensional culture system of the present disclosure at a temperature at which the biocompatible thermoresponsive polymer of the three-dimensional culture system is a semi-solid (e.g., a gel); and, after a period of time such that a desired number of OPCs are generated, cooling the three-dimensional culture system to a temperature at which the thermoresponsive polymer is a liquid. The OPCs thus generated can be isolated by centrifugation or other means of separating cells from a liquid.

The present disclosure provides a three-dimensional culture system that recapitulates closely what happens in vivo during embryonic development. For example, the three-dimensionality of a biocompatible thermoresponsive polymer of the present disclosure provides an environment similar to the natural environment cells reside in during embryonic development, and thus provides an environment for rapid cell growth, that prevents large cell aggregate formation, that protects cells from shear forces, and that has sufficient porosity for the diffusion of small molecules, nutrients and growth factors.

Accordingly, methods using a three-dimensional culture system of the present disclosure allows for rapid generation of OPCs. In some cases, a subject method of generating OPCs using a three-dimensional culture system of the present disclosure require substantially less than 110-150 days, e.g., substantially less than 110 days, substantially less than 100 days, to generate at least $10^3$ OPCs. In some cases, a subject method of generating OPCs using a three-dimensional culture system of the present disclosure requires less than 50 days, e.g., less than 40 days, less than 30 days, less than 20 days, less than 10 days, etc., to generate at least $10^3$ OPCs. In some cases, a subject method of generating OPCs using a three-dimensional culture system of the present disclosure requires from about 18 days to about 20 days, e.g., about 18-20 days, about 15-20 days, about 15 days, about 20 days, etc., to generate at least $10^3$ OPCs. In some cases, a method of the present disclosure for generating OPCs, using a three-dimensional culture system of the present disclosure, generates from about $10^3$ OPCs to about $10^9$ OPCs (e.g., from about $10^3$ to about $10^4$, from about $10^4$ to about $10^5$, from about $10^5$ to about $10^6$, from about $10^6$ to about $10^7$, from about $10^7$ to about $10^8$, or from about $10^8$ to $10^9$, or more than $10^9$, OPCs) in a period of time of from about 5 days to about 30 days, e.g., from about 5 days to about 7 days, from about 7 days to about 10 days, from about 10 days to about 15 days, from about 15 days to about 20 days, from about 20 days to about 25 days, or from about 25 days to about 30 days. In some cases, a method of the present disclosure for generating OPCs, using a three-dimensional culture system of the present disclosure, generates from about $10^3$ OPCs to about $10^9$ OPCs (e.g., from about $10^3$ to about $10^4$, from about $10^4$ to about $10^5$, from about $10^5$ to about $10^6$, from about $10^6$ to about $10^7$, from about $10^7$ to about $10^8$, or from about $10^8$ to $10^9$, or more than $10^9$, OPCs) in a period of time of from about 5 days to about 30 days, e.g., from about 5 days to about 7 days, from about 7 days to about 10 days, from about 10 days to about 15 days, from about 15 days to about 20 days, from about 20 days to about 25 days, or from about 25 days to about 30 days, starting with from 10 to 100 pluripotent cell cells.

The present disclosure provides methods of generating oligodendrocyte precursor cells (OPCs) using a three-dimensional culture system of the present disclosure. Methods of the present disclosure comprise culturing suitable cells (e.g., PSCs, ESCs, etc.) using a three-dimensional culture system for a period of time until a desired number of viable pre-OPCs is generated. Such pre-OPCs can be further differentiated into OPCs.

The present disclosure provides methods of generating viable pre-OPCs. For example, using a method of the present disclosure, at least 40%, at least 45%, at least 50%, at least 55%, at least 60%, at least 65%, at least 70%, at least 75%, at least 80%, at least 85%, at least 90%, at least 95%, at least 99% of the pre-OPCs that are generated are viable.

Pre-OPCs can be distinguished from starting cells by a variety of methods known in the art, according to a number of phenotypic criteria. For example, phenotypic criteria that can be used to distinguish pre-OPCs from starting cells include, but are not limited to, microscopic observation of morphological features, detection or quantitation of expressed phenotypic markers, functional criteria measurable in vitro, and behavior upon infusion into a host animal. A person of skill in the art would readily recognize morphological features that are characteristic of OPCs. For example, OPCs sometimes take a bipolar shape, having two processes extending off opposite poles of the central body. OPCs may also take the form of relative flat cells, bearing many of the same characteristics of oligodendrocytes.

Methods of distinguishing pre-OPCs from starting cells include characterizing whether the pre-OPCs express one or more phenotypic markers characteristic of OPCs. Phenotypic markers that may be used in methods of the present disclosure include, but are not limited to the following, used singly, or in combination, e.g., NG2, a chondroitin sulfate proteoglycan expressed by macrophages and OPCs; PDGFRα, a membrane receptor for PDGF, expressed by OPCs, oligodendrocytes and other cell types; TRα1, a nuclear receptor for thyroid hormone, expressed by OPCs, oligodendrocytes, neurons, and other cell types; myelin proteolipid protein, a component of myelin that is expressed on OPCs and glial precursors; the epitope defined by O4 antibody, a marker for OPCs, oligodendrocytes, astrocytes and astrocyte precursors; vimentin, a fibroblast-type filament protein that marks astrocyte precursors (often negative on oligodendrocytes); glial fibrillary acidic protein (GFAP), a marker for astrocytes (negative on oligodendrocytes); galactocerebroside (GalC), a marker for committed oligodendrocytes; myelin basic protein (MBP), a marker of mature myelin and myelin-producing cells, A2B5, an epitope expressed on type II astrocytes, glial progenitors, OPCs, and pancreatic p cells; the epitope recognized by receptor interacting protein (RIP) antibody, which stains oligodendrocytes and their processes, and coincides with myelinated axons in both the spinal cord and the cerebellum; and the like.

Other phenotypic markers include transcription factors expressed at various times during the pathway of oligodendrocyte differentiation. For example, Olig1, a helix-loop-helix (HLH) family transcription factor, expressed by OPCs, motor neuron progenitors, and kidney cells; Olig2, an HLH family transcription factor, expressed by OPCs, motor neuron progenitors and cells of the pineal gland; Sox10, a Sox family transcription factor, expressed by OPCs, oligodendrocytes, Schwann cells, and cells of the neural crest, cochlea, and prostate, and melanocytes; NKX2.2, a Hox family transcription factor, expressed by OPCs, oligodendrocytes, neuronal progenitors, pancreatic a and 3 cells; Pax6, an HLH family transcription factor, expressed by OPCs, neuronal progenitors, pancreatic a and 3 cells, lens retina, pituitary, liver and spleen; and the like.

Other useful markers include the following: neuronal nuclear antigen (NeuN), a marker of neuronal maturation (normally negative in oligodendrocyte lineage cells); class III beta-tubulin (TuJ1), a marker of neuronal cells; microtubule associated protein 2 (MAP-2), a marker for cells of the central nervous system (may be positive in oligodendrocyte lineage); SSEA-4, Oct-4 or telomerase reverse transcriptase (TERT), markers for undifferentiated PSCs (negative on OPCs and oligodendrocytes); and the like.

Accordingly, the present disclosure provides methods of generating a high percentage of viable pre-OPCs that can be characterized by the detection of a single, or combination, of any phenotypic marker(s) that may include any of the above mentioned phenotypic markers. For example, the present disclosure provides methods of generating at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% viable pre-OPCs that can be characterized by the detection of a single, or combination, of any phenotypic marker(s) that may include any of the above mentioned phenotypic markers (e.g., Olig2 and NKX2.2) relative to the total amount of cells that result from using the present methods.

Phenotypic markers that find use in the present methods may be directly or indirectly labelled using a variety of available methods known in the art. Labelled phenotypic markers offer the convenience of automatic and high-throughput detection.

Phenotypic markers that find use in the present methods may find use as transcriptional reporters wherein the transcriptional reporter comprises a regulatory element (e.g., promoter) of the phenotypic marker in operable linkage to a sequence that encodes a protein that can generate a detectable signal. For example, a protein that can generate a detectable signal includes, but is not limited to, a protein enzyme capable of catalyzing conversion of a substrate to a detectable reaction product, either directly or indirectly, which have been used, for example, in cell based screening assays. For example, enzymes such as β-galactosidase, β-glucuronidase (GUS), β-lactamase, alkaline phosphatase, peroxidase (e.g., horse radish peroxidase), chloramphenicol acetyltransferase (CAT) and luciferase. Any of a range of enzymes capable of producing a detectable product either directly or indirectly may be so modified or may occur naturally.

In addition to protein enzymes which catalyze a reaction to produce a detectable product, proteins, protein domains or protein fragments which are themselves detectable (e.g., a fluorescent protein) can be used. For example, detectable proteins include green fluorescent proteins, which have characteristic detectable emission spectra, and have been modified to alter their emission spectra, as described in PCT WO 96/23810, the disclosure of which is incorporated herein, and fluorescent protein from an Anthozoa species (see, e.g., Matz et al., *Nat. Biotechnol.* 1999, 17:969-973); and the like. Fusions of fluorescent proteins with other proteins, and DNA sequences encoding the fusion proteins which are expressed in cells are described in PCT WO 95/07463, the disclosure of which is incorporated herein.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, *Renilla* GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) *Nature Biotechnol.* 17:969-973, is suitable for use.

In some cases, methods of generating OPCs and/or pre-OPCs of the present disclosure comprise culturing suitable cells using a three-dimensional culture system for a period of time until there is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% viable OPCs or pre-OPCs that are characterized by the detection of a single, or combination, of any of the phenotypic marker(s) described above that have been modified to become detectably labelled (e.g., Olig2 promoter operably linked to GFP and NKX2.2 promoter operably linked to GFP), relative to the total amount of cells that result from using the present methods.

Generating Oligodendrocytes

In some cases, a method of the present disclosure comprises culturing pluripotent stem cells in a three-dimensional culture system of the present disclosure, thereby producing OPCs. In some cases, the OPCs are further differentiated to oligodendrocytes. Thus, the present disclosure provides a method of generating oligodendrocytes, the method comprising culturing a pluripotent stem cell in a three-dimensional culture system of the present disclosure for a period of time such that OPCs are generated; and differentiating the OPCs to oligodendrocytes (e.g., inducing the OPCs to differentiate into oligodendrocytes). Oligodendrocytes can produce factors such as myelin basic protein, proteolipid protein, and myelin-associated glycoprotein Methods of inducing an OPC to differentiate into an oligodendrocyte are known in the art; and any known method can be used, or adapted for use, in a method of the present disclosure.

Starting Cells

Methods of the present disclosure can be practiced using a suitable starting cell (also referred to herein as a "starting cell population") that will undergo differentiation into an OPC and/or pre-OPC. In some cases, a suitable starting cell for use in methods of the present disclosure can be a stem cell (e.g., a pluripotent stem cell) of various types. In some cases, a suitable starting cell is a primate pluripotent stem cell (PSC) derived from tissue formed after gestation, such as a blastocyst, or fetal or embryonic tissue taken any time during gestation. In some cases, a suitable starting cell is an embryonic stem cell. In some cases, a suitable starting cell is an induced pluripotent stem cell. In some cases, a suitable starting cell is an adult stem cell. In some cases, a suitable starting cell is an epiblast stem cell. In some cases, a suitable starting cell is a germ stem cell. Non-limiting examples of suitable starting cells are primary cultures or established lines of embryonic stem cells or embryonic germ cells, as described above and hereinbelow.

Embryonic stem cells (ESCs) can be isolated from primate tissue (U.S. Pat. No. 5,843,780; Thomson et al., Proc. Natl. Acad. Sci. U.S.A. 1995, 92:7844). Human embryonic stem cells (hESCs) can be prepared from human blastomeres using techniques described by Thomson et al. (U.S. Pat. No. 6,200,806; *Science.* 1998, 282:1145; *Curr. Top. Dev. Biol.* 1998, 38:133 ff.) and Reubinoff et al, *Nature Biotech.* 2000, 18:399. Equivalent cell types to hESCs include their pluripotent derivatives, such as primitive ectoderm-like (EPL) cells, as outlined in WO 01/51610 (Bresagen).

In one method, the zona pellucida is removed from developed blastocysts by brief exposure to pronase (Sigma). The inner cell masses are isolated by immunosurgery, in which blastocysts are exposed to a 1:50 dilution of rabbit anti-human spleen cell antiserum for 30 min, then washed for 5 min three times in DMEM, and exposed to a 1:5 dilution of Guinea pig complement (Gibco) for 3 min (Solter et al., *Proc. Natl. Acad. Sci. U.S.A.* 1975, 72:5099). After two further washes in DMEM, lysed trophectoderm cells are removed from the intact inner cell mass (ICM) by gentle pipetting, and the ICM plated on mEF feeder layers. After 9 to 15 days, inner cell mass-derived outgrowths are dissociated into clumps, either by exposure to calcium and magnesium-free phosphate-buffered saline (PBS) with 1 mM EDTA, by exposure to dispase or trypsin, or by mechanical dissociation with a micropipette; and then replated on mEF in fresh medium. Growing colonies having undifferentiated morphology are individually selected by micropipette, mechanically dissociated into clumps, and replated. ESC-like morphology is characterized as compact colonies with apparently high nucleus to cytoplasm ratio and prominent nucleoli. Resulting ESCs are then routinely split every 1-2 weeks by brief trypsinization, exposure to Dulbecco's PBS (containing 2 mM EDTA), exposure to type IV collagenase (about 200 U/mL; Gibco) or by selection of individual colonies by micropipette.

Human Embryonic Germ cells (hEGCs) can be prepared from primordial germ cells as described in Shamblott et al., *Proc. Natl. Acad. Sci. U.S.A.* 1998, 95:13726 and U.S. Pat. No. 6,090,622. Briefly, genital ridges taken after about 8-11 weeks are rinsed with isotonic buffer, then placed into 0.1 mL 0.05% trypsin/0.53 mM sodium EDTA solution (BRL) and cut into <1 mm$^3$ chunks. After disaggregation, the cells are incubated 1 h or overnight at 37° C. in about 3.5 mL EG growth medium (DMEM containing D-glucose, NaHCO$_3$; 15% ES qualified fetal calf serum; 2 mM glutamine; 1 mM sodium pyruvate; 1000-2000 U/mL human recombinant leukemia inhibitory factor; 1-2 ng/mL human recombinant bFGF; and 10 μM forskolin (in 10% DMSO). The cells are then resuspended in 1-3 mL of EG growth medium, and plated onto a feeder layer (e.g., STO cells, ATCC No. CRL 1503, inactivated with 5000 rad .gamma.irradiation). The first passage is done after 7-10 days, and then cultured with daily replacement of medium until cell morphology consistent with EG cells is observed, typically after 7-30 days or 14 passages.

hESCs can be obtained from established lines obtainable from public depositories (for example, the WiCell Research Institute, Madison Wis. U.S.A., or the American Type Culture Collection, Manassas Va., U.S.A.). U.S. Patent Publication 2003-0113910 A1 reports pluripotent stem cells derived without the use of embryos or fetal tissue. It may also be possible to reprogram cord blood or other progenitor cells into PSCs by using a factor that induces the pluripotent phenotype (Chambers et al., *Cell.* 2003, 113:643; Mitsui et al., *Cell.* 2003, 113:631). Under appropriate conditions, any cell that otherwise meets the definitions for PSCs or ESCs can be used.

Methods of the present disclosure can be used to generate OPCs and pre-OPCs from induced pluripotent stem cells (iPSCs). iPSCs can be derived from mammalian cells (e.g., mammalian somatic cells). Suitable mammalian cells that can be used to generate iPSCs include, but are not limited to, fibroblasts, skin fibroblasts, dermal fibroblasts, bone marrow-derived mononuclear cells, skeletal muscle cells, adipose cells, peripheral blood mononuclear cells, macrophages, hepatocytes, keratinocytes, oral keratinocytes, hair follicle dermal cells, epithelial cells, gastric epithelial cells, lung epithelial cells, synovial cells, kidney cells, skin epithelial cells, pancreatic beta cells, and osteoblasts. Mammalian cells used to generate iPSCs that can be used by methods of the present disclosure can originate from a variety of tissue types including, but not limited to, bone marrow, skin (e.g., dermis, epidermis), muscle, adipose tissue, peripheral blood, foreskin, skeletal muscle, and smooth muscle. The cells used to generate iPS cells can also be derived from neonatal tissue, including, but not limited to: umbilical cord tissues (e.g., the umbilical cord, cord blood, cord blood vessels), the amnion, the placenta, and various other neonatal tissues (e.g., bone marrow fluid, muscle, adipose tissue, peripheral blood, skin, skeletal muscle etc.).

The generation of iPSCs can be achieved by a variety of methods known in the art. Briefly, cells are subject to a set of reprogramming factors (e.g., a combination of an Oct family protein, a Sox family protein and a Klf family protein). U.S. Pat. No. 9,132,152 discloses various methods of generating iPSCs, including various sets of reprogramming factors that are known in the art.

The starting cell population can include from 10 starting cells to $10^5$ starting cells, e.g., from 10 cells to $10^2$ cells, from $10^2$ cells to $10^3$ cells, from $10^3$ cells to $10^4$ cells, or from $10^4$ cells to $10^5$ cells. In some cases, the starting cell population is from 10 starting cells to $10^2$ starting cells. In some cases, the starting cell population is from 10 pluripotent stem cells to $10^2$ pluripotent stem cells. In some cases, the starting cell population is from 10 embryonic stem cells to $10^2$ embryonic stem cells. In some cases, the starting cell population is from 10 induced pluripotent stem cells to $10^2$ induced pluripotent stem cells. In some cases, the starting cell population is from 10 epiblast stem cells to $10^2$ epiblast stem cells. In some cases, the starting cell population is from 10 germ stem cells to $10^2$ germ stem cells. In some cases, the starting cell population is from 10 pluripotent stem cells to $10^3$ pluripotent stem cells. In some cases, the starting cell population is from 10 embryonic stem cells to $10^3$ embryonic stem cells. In some cases, the starting cell population is from 10 induced pluripotent stem cells to $10^3$ induced pluripotent stem cells. In some cases, the starting cell population is from 10 epiblast stem cells to $10^3$ epiblast stem cells. In some cases, the starting cell population is from 10 germ stem cells to $10^3$ germ stem cells.

Methods of Treatment

The present disclosure provides a method of treating a disorder in an individual in need thereof, the method generally involving: a) generating an OPC, or an olidodendrocyte, using a method of the present disclosure; and b) administering the OPC or oligodendrocyte into an individual in need thereof, thereby providing a treatment. In some cases, an OPC or oligodendrocyte can be differentiated from a human PSC using a three dimensional culture system of the present disclosure.

In some cases, treatment methods of the present disclosure comprise implanting into the individual an implantable system that comprises a three-dimensional culture system of the present disclosure and PSCs (e.g., human ESCs, human PSCs, iPSCs, etc.). For example, in some cases, an implantable system of the present disclosure comprises a three-dimensional culture system comprising a three-dimensional thermoresponsive biocompatible polymer and one or more factors that drive the differentiation of PSCs into OPCs and pre-OPCs as described above. In some cases, upon implanting an implantable three-dimensional culture system of the present disclosure into an individual in need thereof, PSCs of the implantable system will undergo differentiation into OPCs and pre-OPCs and continue onto the OPC lineage to generate myelin-producing cells (e.g., oligodendrocytes). In some cases, OPCs generated by an implantable system of the present disclosure will migrate into and populate areas that lack OPCs (e.g., areas that lack myelination), or that lack sufficient numbers of OPCs, thereby providing such areas with myelin-producing cells. In some cases, a treatment method of the present disclosure comprises implanting a system of the present disclosure into the vicinity of PSCs such that the PSCs that migrate and/or proliferate into the three-dimensional culture system undergo rapid differentiation into OPCs or pre-OPCs.

In some cases, a treatment method of the present disclosure comprises introducing a three-dimensional culture system comprising PSCs into an individual at an appropriate site (e.g., brain, spinal cord, etc.). Sites and modes of administration can include, e.g., implantation (e.g., of an implantable device as described above) into the brain; intravenous infusion (e.g., of a three-dimensional culture system comprising PSCs); intramuscular injection (e.g., of a three-dimensional culture system comprising PSCs); intracranial implantation (e.g., of a three-dimensional culture system comprising PSCs); intraocular implantation (e.g., of a three-dimensional culture system comprising PSCs); intrathecal implantation (e.g., of a three-dimensional culture system comprising PSCs); intra-spinal cord implantation (e.g., of a three-dimensional culture system comprising PSCs); and the like.

Individuals Suitable for Treatment

Treatment methods of the present disclosure may be performed on an individual that has a disease or condition characterized by the lack of, or decreased levels of myelination. In some cases, a suitable individual has suffered a traumatic injury (e.g., spinal cord injury). In some cases, a suitable individual has undergone treatment (e.g., radiotherapy for a brain tumor) that impairs the ability to remyelinate. In some cases, a suitable individual has demyelinating myelinoclastic disease, or demyelinating leukodystrophic disease. For example, an individual that would be suitable as a target for a treatment method of the present disclosure includes those that have a demyelinating disorder of the central nervous system (CNS), e.g., multiple sclerosis, Devic's disease and other inflammatory demyelinating disease, CNS neuropathies like those produced by vitamin B12 deficiency, central pontine myelinolysis, myelopathies like tabes *dorsalis* (syphilitic myelopathy), leukoencephalopathies (e.g., progressive multifocal leukoencephalopathy), leukodystrophies (e.g., adrenomyeloneuropathy, Alexander disease, cerebrotendineous xanthomatosis, hereditary CNS demyelinating disease, Krabbe disease, metachromatic leukodystrophy, Pelizaeus-Merzbacher disease, Canavan disease, leukoencephalopathy with vanishing white matter, adrenoleukodystrophy, Refsum disease, xenobefantosis, and others. For example, an individual that would be suitable as a target for a treatment method of the present disclosure includes those that have a demyelinating disorder of the peripheral nervous system (PNS), e.g., Guillain-Barre syndrome, chronic inflammatory demyelinating polyneuropathy, anti-MAG peripheral neuropathy, Charcot-Marie-Tooth disease, copper deficiency associated conditions (e.g., peripheral neuropathy, myelopathy, optic neuropathy), progressive inflammatory neuropathy, and others.

Screening Methods

The present disclosure provides methods of screening. In some cases, a screening method uses a three-dimensional culture system of the present disclosure in vitro (e.g., for drug discovery). In some cases, a screening method uses a three-dimensional culture system of the present disclosure in vivo (e.g., for disease modelling). In some cases, a screening method of the present disclosure allows a person of skill in the art to identify a compound that drives the generation of OPCs from suitable cells as previously described (e.g., a PSC). In some cases, a compound identified by screening methods of the present disclosure increases the rate of generation of OPCs from suitable cells, e.g., by 10%, by 20%, by 30%, by 40%, by 50%, by 60%, by 70%, by 80%, by 90%, by 100% or more (e.g., by 120%, by 150%, by 200% or more). For example, a compound identified by screening methods of the present disclosure increases the rate of OPC generation from around 20 days to less than 20 days, to less than 15 days, to less than 10 days, to about 5 days, etc. Such methods at least comprise, for example, culturing a suitable cell in a three-dimensional culture system of the present disclosure which comprises a biocompatible polymer and a combination of factors as previously described, contacting the cell with a test compound, and assessing the rate at which OPCs are generated.

In some cases, a compound identified by screening methods of the present disclosure may replace one or more of the components of the combination of factors that make up a three-dimensional culture system required to drive the generation of OPCs. This may be done by systematically removing one or more of the factors and assessing whether the addition of a test compound can replace the function of the missing factor(s). For example, a compound identified by such methods may be able to replace the function of both retinoic acid and dual-SMAD inhibitor, or the function of both the Shh pathway antagonist and the retinoic acid, etc. Such methods at least comprise, for example, culturing a suitable cell in a three-dimensional culture system of the present disclosure which comprises a biocompatible polymer and a combination of factors as previously described with one or more factors removed, contacting the cell with a test compound and assessing whether the test compound allows for the generation of OPCs.

Screening methods of the present disclosure may be used to identify compounds that can be used in treatment for a myelin-related disease. For example, a screening method may comprise culturing suitable cells using a three-dimensional culture system to produce OPCs and oligodendrocytes, co-culturing the system with neurons, and assessing whether a test compound has any effect on the level of myelination of the neurons. For example, a screening method may comprise: co-culturing pre-OPCs with neurons in a three-dimensional culture system as previously described, to produce a mixed population of cells; contacting the mixed population of cells with a test compound; identifying a test compound that increases or decreases the level of myelination of the neurons, thereby identifying a compound that changes the level of myelination of the neurons. In such a method, all components are located in the same space (e.g., the same culture dish, the same well of a multi-well culture plate, etc). In some cases, a screening method of the present disclosure may identify a compound that increases the level of myelination of the co-cultured neurons. For example, the compound may increase the level of myelination of the co-cultured neurons by 10%, by 20%, by 30%, by 40%, by 50%, by 60%, by 70%, by 80%, by 90%, by 100% or more. Such a compound that increases the level of myelination of neurons can be further developed into a therapeutic to treat a demyelinating disease (e.g., multiple sclerosis, hypomyelinating leukodystrophy, and the like) or a central nervous system injury that involves inflammation and loss of myelin. In other cases, a screening method of the present disclosure may identify a compound that decreases the level of myelination of the co-cultured neurons. For example, the compound may decrease the level of myelination of the co-cultured neurons by 10%, by 20%, by 30%, by 40%, by 50%, by 60%, by 70%, by 80%, by 90%, by 100%. Such a compound that decreases the level of myelination of neurons can be further developed into a therapeutic to treat a disease characterized by hypermyelination, e.g., autosomal recessive hypermyelinating neuropathy (Sabatelli et al., *Acta Neuropathol.* 1994, 87(4):337-342).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

The PNIPAAm-PEG three-dimensional culture system described in the present disclosure is designed for production of cells for disease modelling, drug screening, and cell transplantation studies and therapies. FIG. 1 depicts a schematic of the differentiation protocol for pre-OPC patterning from PSCs. This differentiation protocol employs a three-dimensional culture system comprising a PNIPAAm-PEG-based biocompatible thermoresponsive polymer, an Shh signaling pathway agonist, a Wnt signaling pathway agonist and retinoic acid. As depicted, the timing of the addition and removal of different factors is important.

Figure 2A:
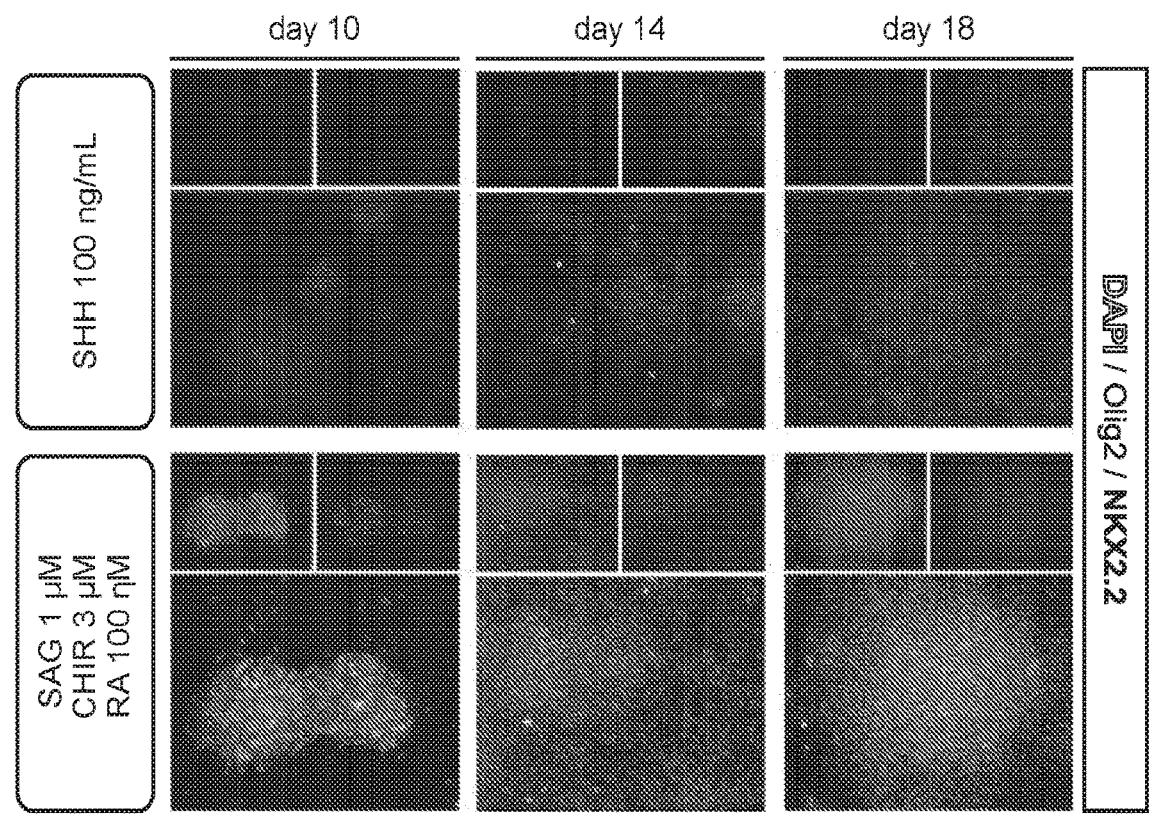
FIG. 2A-2B depict a time-course analysis of Olig2 and NKX2.2 expression using different conditions for pre-oligodendrocyte precursor cell differentiation.
Figure 2B:
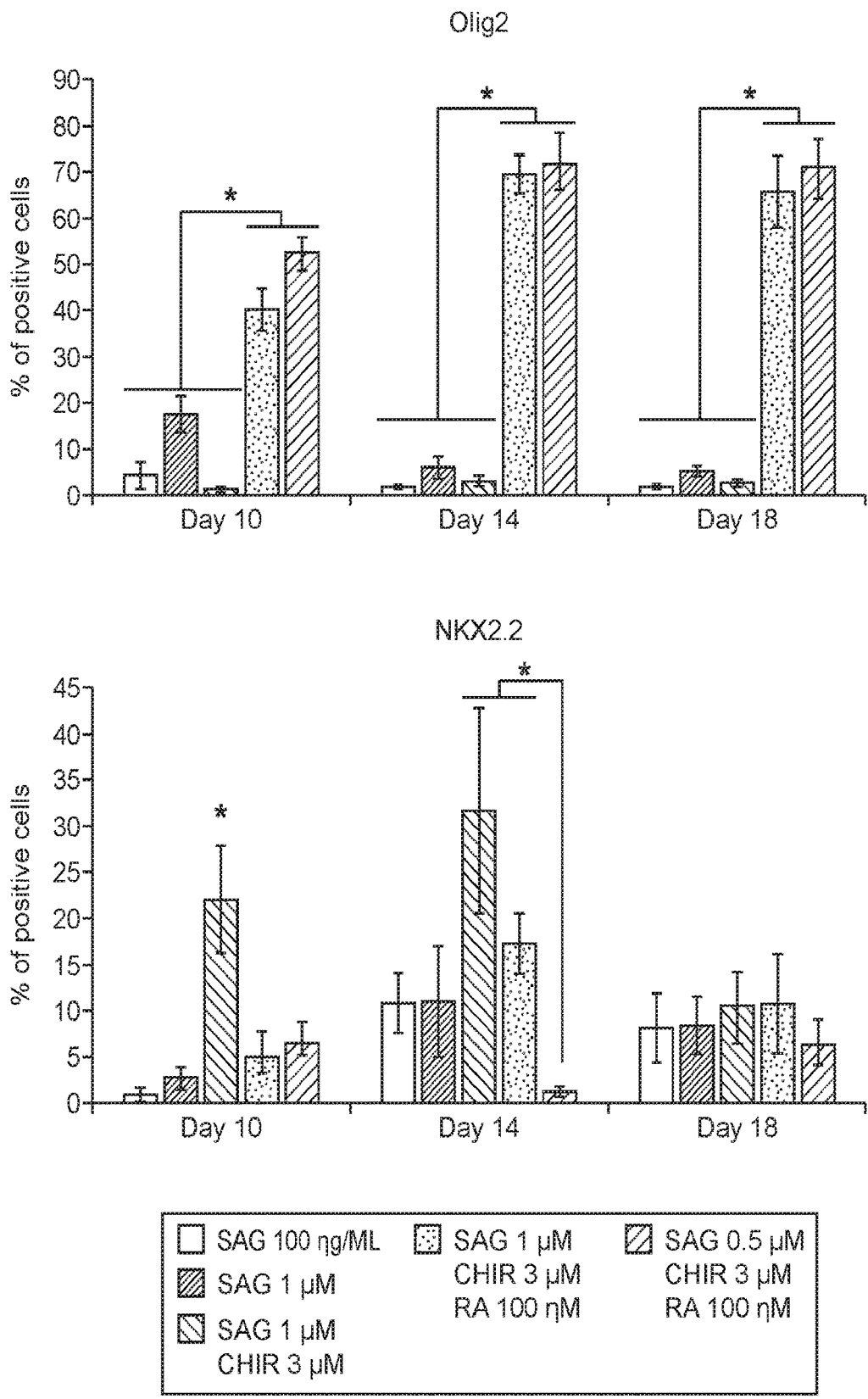

In FIG. 2A-2B, hPSC-derived cells express the definitive OPC markers Olig2 and NKX2.2 after differentiation. The system can also be used for the differentiation of pre-OPCs into OPCs and for the maturation of oligodendrocytes in a large-scale manner. FIG. 2 depicts a time-course analysis of Olig2 and NKX2.2 expression using different conditions for pre-OPC differentiation. FIG. 2A shows micrographs of Olig2 and NKX2.2 expression in cells that experienced different differentiation conditions. FIG. 2B shows the expression level of Olig2 and NKX2.2 in cells that experienced different differentiation conditions. Asterisks represent p-value of less than 0.05 as evaluated by a Students' t-test.

Example 2

Oligodendrocyte precursor cells (OPCs) can be used for the treatment of demyelinating diseases and conditions of the central nervous system. However, acquiring sufficient numbers of high-quality OPCs has been a challenge. Here, it has been shown that OPCs can be generated from human pluripotent stem cells (hPSCs) in a three-dimensional (3D), scalable, fully-defined thermoresponsive biomaterial system. CRISPR-Cas9 was used to create an NKX2.2-EGFP (NKX2.2 enhanced green fluorescent protein) human embryonic stem cell reporter line that enabled fine-tuning of early OPC specification and the identification of conditions that markedly increased the number of OLIG2+ and NKX2.2+ cells generated from hPSCs. Transplantation of these biomaterial-generated 50-day-old OPCs, without purification, into the brains of NOD/SCID mice led to cell engraftment, migration, and maturation into myelinating oligodendrocytes in vivo. These results demonstrate the use of 3D platforms for rapid and large-scale production of OPCs.

EXPERIMENTAL PROCEDURES

Plasmid Construction and Gene Targeting

Oligonucleotides encoding the sgRNA targeting NKX2.2 were custom ordered (gRNA-NKX2.2-Fwd and gRNA-KNX2.2-Rev, Elim Biopharm), phosphorylated by T4 polynucleotide kinase (New England Biolabs), hybridized and ligated into the BbsI restriction site of pX330-U6-Chimeric-BB-CBh-hSpCas9 vector (Add gene plasmid #42230; (Cong et al., Science 339, 819-823 (2013)). Homology arms from the NKX2.2 locus were amplified using a nested polymerase chain reaction (PCR) strategy from genomic DNA harvested from H9 cells, using the primers ON-HA-1 or 2-Fwd and ON-HA-1 or 2-Rev, for the external PCR round, and IN-HA-1 or 2-Fwd and IN-HA-1 or 2-Rev, for the internal PCR round. Primer sequences are provided in FIG. 19. The EGFP and the puromycin-resistance genes were PCR amplified from the templates AAV-CAGGS-eGFP (Add gene plasmid #22212) and SA-OCT-GFP-2APuro-PA (Add gene plasmid #22209; (Hockemeyer et al., Nat. Biotechnol., 2009. 27, 851-857)), respectively, and fused to one another and both homology arms by overlap PCR. The ensuing PCR product (HA1-linker-EGFP-pA-PGK-Puro-pA-HA2) was digested and ligated into the NotI restriction site of pAAV-CAG-EGFP (Kotterman et al., *Development* 142, 1885-1892 (2015)). Correct construction of each expression cassette was verified by sequence analysis. For hESC gene editing, cells were transfected with 40 µg of donor plasmid and 10 µg of SpCas9-sgRNAexpression vector. At 72 hours after electroporation (Gene Pulser Xcell, Bio-Rad), cells were dissociated and seeded in the presence of 10 µM Rho-kinase (ROCK) inhibitor (RI) and 0.4 µg/mL of puromycin (Tocris) (Blair et al., *J. Vis. Exp* 1-9 (2016)). After 2 weeks of puromycin selection, individual puromycin-resistant colonies were harvested for genotyping and banked.

hPSC Cell Culture

Human WIBR3 (Lengner et al., Cell 141, 872-883 (2010)) (NIH Stem Cell Registry #0079), H9 ESCs (NIH StemCell Registry #0062) and TCTF-8FLVY6C2 iPSCs were cultured as previously described (Lei and Schaffer, Proc. Natl. Acad. Sci. U.S.A 110, E5039-48 (2013)). Briefly, after Accutase (Stem Cell Technologies) dissociation, single cells were seeded in the presence of 10 µM ROCK inhibitor, Y-27632 (Selleckchem) and E8 medium (Life Technologies) in PNI-PAAm-PEG hydrogel (CosmoBio) and expanded for 4-5 days before differentiation.

OPC Differentiations

Figure 4A:
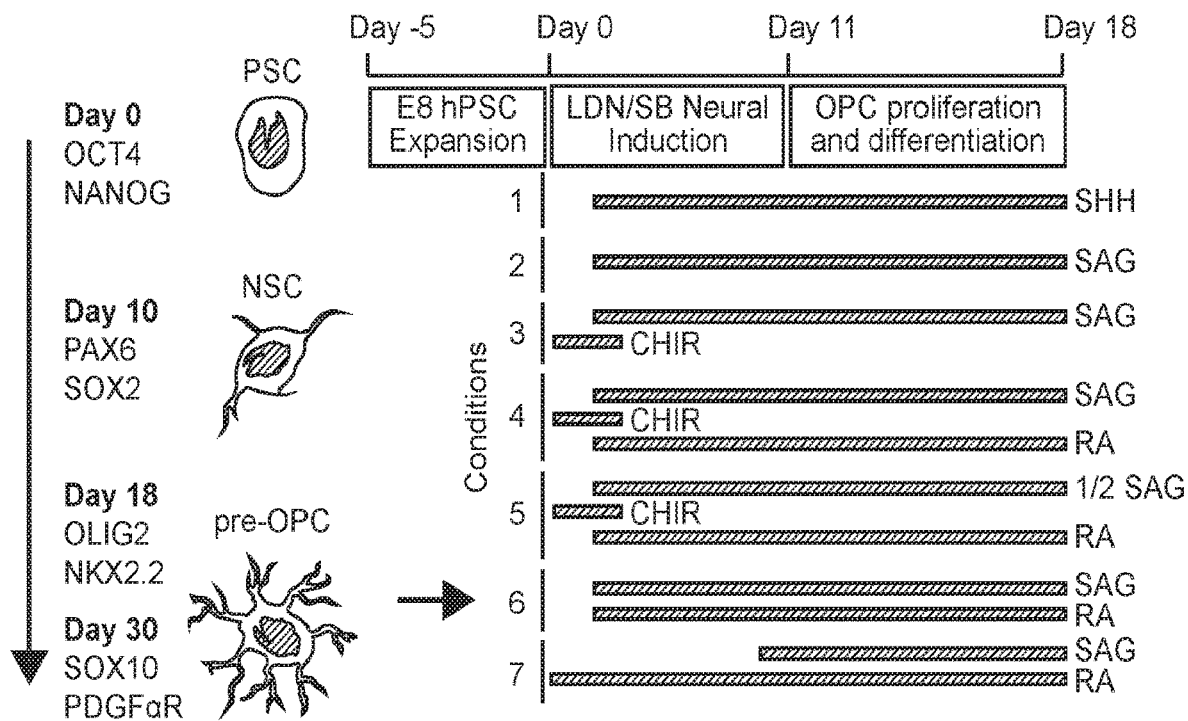

Following expansion, hPSCs were cultured in early OPC differentiation medium as described in FIG. 4A and fed daily with neural induction medium. All media compositions and factor concentrations are provided in FIG. 20. Briefly, cells were first patterned with the dual-SMAD inhibitors LDN193189 and SB431542, and then ventralized using SHH or SAG. In some conditions, cells were caudalized using RA. On day 11 of the differentiation, cell-aggregates were split at a 1 to 3 ratio, broken into smaller-size aggregates by gentle pipetting (up and down, 10-15 times), re-encapsulated in the thermoresponsive gel, and fed with OPC proliferation medium. O1 ng/mL of FGF-2 (Peprotech) was then added to the OPC proliferation media described in FIG. 7A (added daily from day 14 until day 18, or from day 20 until day 24 of the differentiation). After FGF treatment, cells were fed every 2-3 days with OPC maturation medium, which included 20 µg/mL of L-Ascorbic Acid (Sigma) from day 75 until day 95. See FIG. 20 for a detailed description of the differentiation conditions.

Electrophysiology

After 75 days of OPC differentiation, cell aggregates were seeded on 0.01% poly-L-ornithine (Sigma) plus 20 g/mL laminin (Life Technologies) coated 12 mm glass coverslips. Medium was replenished by 50% every 2-3 days. On day 89, O4 live staining was performed as previously described (Douvaras and Fossati, *Nat. Prtoc.* 10, 1143-1154 (2015)), and voltage sensitive dyes were used to monitor electrophysiological activity of the differentiated cells (Huang et al., J. Am. Chem. Soc. 137, 10767-10776 (2015)). Briefly, for experiments measuring OPC spiking activity, cells were incubated with RVF5 (1 µM) in Hank's Balanced Salt Solution (HBSS) at 37° C. for 15 min at room temperature. Cells were then excited using a 1 ms/60V pulse and images of the LED-excited dye were acquired with a W-Plan-Apo 63×/1.0 objective (Zeiss) and OrcaFlash 4.0 sCMOS camera (sCMOS). For image processing, regions of interest encompassing O4-positively stained cell bodies were drawn in ImageJ and the mean fluorescence intensity (MFI) across the video was extracted. A custom analysis routine was used to extract fluorescence intensity information and automatically perform bleach correction. The routine then detected spikes using a value of 3× the standard deviation of the baseline fluorescence in each trace.

Transplantation into NOD/SCID Mice

All stem cell procedures and procedures in animals were performed following NIH Guidelines for Animal Care and Use and were approved by the UC Berkeley Animal Care and Use Committee (ACUC), the Committee for Laboratory and Environmental Biosafety (CLEB), and the Stem Cell Research Oversight committee (SCRO). OPCs differentiated for 50 days were harvested as spheres from the three-dimensional (3D) gel and resuspended in OPC maturation medium at a density of 50,000 cells/µL. Then, 3 µL (~150,000 cells) were injected into the corpus callosum of 30 day-old NOD/SCID mice (The Jackson Laboratory) at the stereotaxic coordinates: AP: +1.2, ML: −1.2, DV: −2.0 using a 10 µL syringe with a 22 s Gauge Point Style 4 needle with a 30° angle (Hamilton). Animals were euthanized at 3 or 16 weeks after surgery by transcardiac perfusion with 4% paraformaldehyde (PFA). Brains were processed and sectioned.

Genotype PCR

After puromycin selection, puromycin-resistant clones were dissociated with Accutase for 7 min at 37° C. DNA was then extracted using the QuickExtract DNA Extraction Solution (Epicentre) according to manufacturer's instructions. After nested PCR, products amplified with the primers IN-Diag-Fwd and IN-Diag-Rev were resolved by agarose gel electrophoresis. To determine integration copy number, the wild-type locus was amplified with the primers ON-HA-1-Fwd and ON-HA-2-Rev.

Southern and Western Blotting

Southern blot analysis was performed as described (Chiba et al., 2015). Briefly, genomic DNA was digested with SacI overnight, then separated using a 0.7% agarose gel, transferred to a nylon membrane and hybridized with an 32P-labeled EGFP probe. Western blot analysis was performed as described (Bugaj et al., 2015). Briefly, N30 cells were expanded as pluripotent stem cells or differentiated using the conditions depicted on FIG. 4A for 20 days. Before analysis, cells were lysed in ice cold Radioimmunoprecipitation (RIPA) buffer in the presence of protease and phosphatase inhibitors, and run resolved on a 10% sodium dodecyl sulfate-polyacrylamide gel electrophoresis (SDS-PAGE) gel. Proteins were then blotted on a nitrocellulose membrane and probed for NKX2.2 (DSHB) and GFP (Invitrogen).

Luciferase Assay

To clone wild-type NKX2.2 or NKX2.2-EGFP into mammalian expression vectors, RNA was first extracted from differentiated OPCs using TRIzol (Invitrogen), according to the manufacturer's instructions. Then, cDNA was synthesized using the ThermoScript RT-PCR System and oligo(dT) 20 oligo reagent (ThermoFisher). The wild-type NKX2.2 coding region was PCR amplified using the primers 5'NKX2.2 mRNA and 3'NKX2.2 mRNA, and cloned into the BamH1 and XhoI restriction sites of pcDNA 3.1 (Life Technologies). EGFP was fused to wild-type NKX2.2 by overlap PCR and also cloned into the BamH1 and XhoI restriction sites of pcDNA 3.1. The NKX2.2-luciferase reporter plasmid was generated by PCR amplification of the luciferase gene with a 5' primer that encoded four repeats of the NKX2.2 binding site. HEK293T cells were transfected with NKX2.2-luciferase reporter plasmid, NKX2.2 expression vectors and *Renilla* expression vector for normalization using PEI. After 48 hr, cells were evaluated for luciferase expression using the Dual Luciferase Reporter Assay (Promega).

Flow Cytometry Analysis

After differentiation in 3D, N30 cells were harvested and dissociated using Accutase. After one wash with phosphate-buffered saline (PBS), cells were incubated in 2% PFA for 15 min. Enhanced green fluorescent protein (EGFP) expression was then measured using a BD LSR Fortessa X-20 Cell Analyzer. N30 hESCs were used as negative controls. For each sample, 10,000 or more live events were collected. Results were analyzed using Flowing.

Immunocytochemistry (ICC)

For ICC analysis of cells differentiated in 3D, cell-spheres were transferred onto poly-D-lysine (10 µg/mL) and laminin (10 µg/mL)-coated glass-bottom plates, and incubated with their respective medium to enable cell spreading. After 48 hr (for early OPC differentiation) or 5 days (for late stage OPC analysis), cells were fixed with 4% PFA for 15 min at RT. After one wash with PBS, cells were incubated overnight at 4° C. with primary antibody in freshly prepared staining primary solution (5% donkey serum, (DS), 2% bovine serum albumin (BSA) and 0.25% Triton X-100 in PBS). Then, cells were gently washed twice with PBS, and incubated for 2 hr at room temperature (RT) with secondary antibodies and 4',6-diamidino-2-phenylindole (DAPI) (1:1000) in freshly prepared secondary staining solution (2% DS, 2% BSA and 0.25% Triton X-100 in PBS). Cells were then washed three times with PBS and imaged using a Zeiss Axio Observer epi-fluorescent microscope. Image Xpress Micro (IXM) was used for ICC quantification analysis, and Zeiss LSM 710 Axio Observer was used for confocal imaging. Images were analyzed using ImageJ and quantified using CellProfiler.

Quantitative Polymerase Chain Reaction (qPCR) Analysis

Cells were harvested and RNA was extracted using TRIzol according to the manufacturer's instructions. 50 ng of RNA was then used to synthesize cDNA using iScript reverse transcription supermix for reverse transcription-quantitative polymerase chain reaction (RT-qPCR) (Bio-Rad), according manufacturer's instructions. 1.25 ng of cDNA template was used per qPCR reaction (in triplicate) using Taq DNA polymerase (NEB) with JumpStart Taq antibody (Sigma) and SYBR green. Results were compared to expression levels in undifferentiated cells, and normalized to the glyceraldehyde-3-phosphate dehydrogenase (GAPDH) gene. Log 2 normalized expression values of the averaged fold-change were used for ClustVis analysis (Metsalu and Vilo, 2015).

Immunohistochemistry (IHC) Analysis

Brains were incubated overnight at 4° C. with 4% PFA and then transferred to a 30% (w/v) sucrose solution at 4° C. for 4-5 days (until brains sunk). Dry ice-frozen tissue was sectioned into 40 µm thick coronal sections using a microtome. Primary antibodies were diluted in primary blocking buffer (5% DS, 2% BSA and 0.1 Triton X-100 in PBS), and brain sections were incubated for 72 hours at 4° C. with very gentle rocking. Sections were then washed once with 0.2% Triton X-100 in PBS, and washed three times with 0.1% Triton X-100 in PBS. Secondary antibodies were diluted in PBS with 2% BSA and incubated for 4 hr at room temperature (RT). DAPI was added 30 min before the end of incubation. Stained sections were washed three times with PBS and mounted on coverslips for imaging.

Cell Survival Analysis after Transplantation

The percentage of human nuclear antigen (HNA)-positive cells was calculated using the Abercrombie's technique (Abercrombie, 1946). All cells positive for HNA were counted from pictures originally acquired using the Zeiss AxioObserver epi-fluorescent microscope, of every 6th brain section spanning the regions with HNA-positive cells (~8 sections across ~50 total sections), without overlapping the areas containing the cells. The total number of HNA-positive cells was then extrapolated from CellProfiler-counted images.

Statistics

Data represented is the mean of three or more independent experiments, unless stated otherwise. Error was calculated as the standard deviation of the mean. Statistical significance was calculated using the Mann-Whitney test (GraphPad Prism).

Results

Generation of a NKX2.2-EGFP Reporter Cell Line by Genome Editing

Figure 3B:
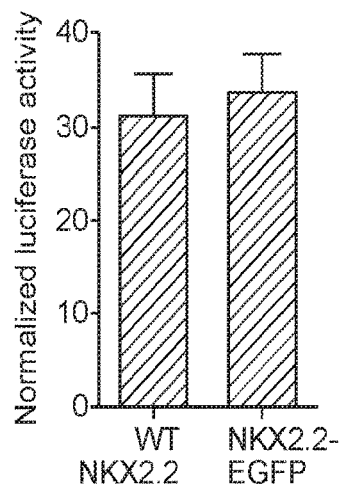

Due to its important role in promoting oligodendrocyte differentiation and maturation (Fu et al., *Development* 129, 681-693 (2002); Qi et al., *Development* 128, 2723-2733 (2001); Zhou et al., *Neuron* 31, 791-807 (2001)), as well as its higher specificity (Masahira et al., *Dev. Biol.* 293, 358-369 (2006)) and potentially importance (Qi et al., *Development* 128, 2723-2733 (2001)) for OPC differentiation relative to early markers such as OLIG2, it was hypothesized that monitoring NKX2.2 expression could be harnessed to optimize early OPC differentiation. Therefore a strategy was developed to generate an hESC line with EGFP knocked into the nkx2.2 locus and thereby generate a NKX2.2-EGFP fusion protein (FIG. 3A). It was first tested whether a NKX2.2-EGFP fusion could still function to stimulate transcription. HEK293T cells were co-transfected with an expression vector encoding either wild-type NKX2.2, or a NKX2.2-EGFP fusion, as well as a reporter plasmid harboring four direct repeats of the NKX2.2 binding site (Berger et al., *Cell* 133, 1266-1276 (2008)) upstream of a luciferase reporter gene. Importantly, no difference (p>0.5) in luciferase expression was observed between the two NKX2.2 variants (FIG. 3B).

Figure 3C:
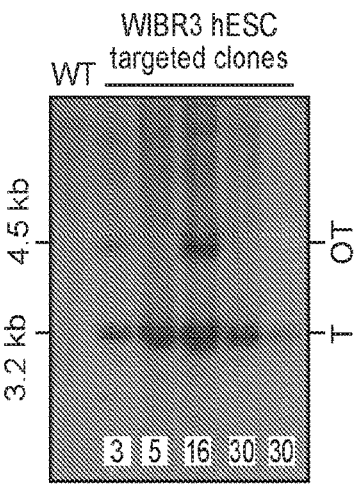
Figure 10A:
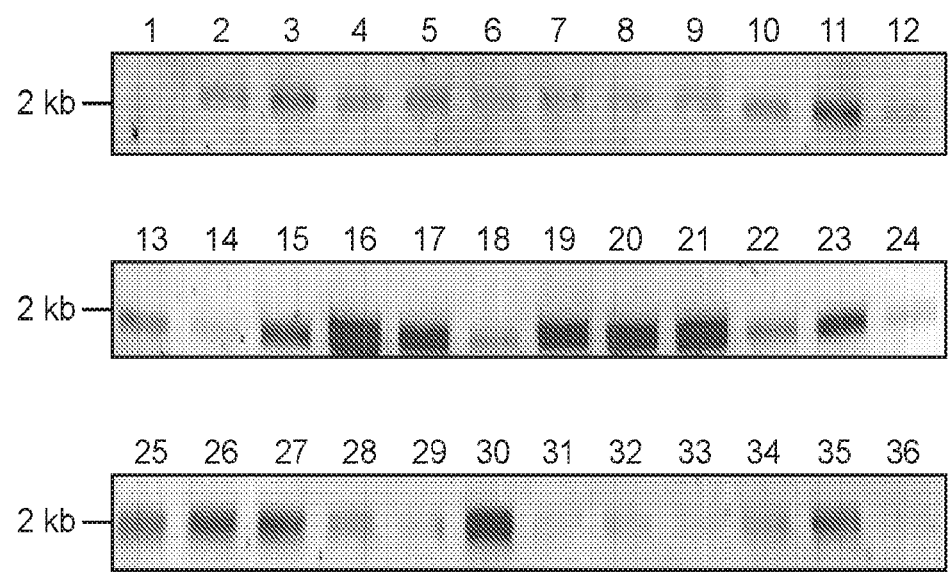
FIG. 10A-10B depict characterization of WIBR3 hESCs after gene targeting and puromycin selection.

The Cas9 nuclease was next used from *Streptococcus pyogenes* (SpCas9) targeted via a single guide RNA (sgRNA) to the human nkx2.2 locus—which has not previously undergone gene targeting in hPSCs—to stimulate homology-directed repair (HDR) mediated insertion of a donor construct encoding EGFP and a PGK-puromycin expression cassette flanked by homology arms to nkx2.2 (FIG. 3A). Following puromycin selection, 36 clones were obtained, 23 of which were positive for targeted integration as determined by PCR (FIG. 10A). Of 5 positive clones selected for Southern blot analysis, 3 showed no apparent signs of off-target integration (FIG. 3C). Following expansion within the 3D hydrogel system as described (Lei and Schaffer, *Proc. Natl. Acad. Sci. U.S.A* 110, E5039-48 (2013)), clone N30 was found to contain the correct mono-allelic modification (FIG. 10B) and expressed both OCT4 and NANOG, indicating it likely retained pluripotency (FIGS. 3D-3E), and it was thus chosen for all subsequent experiments. Immature N30 hESCs did not express NKX2.2 and thus had only background green fluorescence (FIG. 3F). Importantly, however, as anticipated both wild-type NKX2.2 and NKX2.2-EGFP were detected via western blot upon initial differentiation of N30 cells into OPCs (FIG. 3F).

Patterning OPC Differentiation in a 3D Biomaterial

During organismal development, following neural tube patterning and neural stem cell differentiation, OPCs emerge in both the developing spinal cord and the forebrain in three sequential waves (Goldman and Kuypers, *Development* 142, 3983-3995 (2015)). Following a differentiation route analogous to how OPCs are generated in the first wave within the spinal cord—where Sonic hedgehog (SHH) induces OPC emergence from the pMN domain (Lu et al., *Cell* 109, 75-86 (2002)) and retinoic acid (RA) promotes their caudalization (Stacpoole et al., *Stem Cell Reports* 1, 437-450 (2013))—can promote their rapid production from hPSCs ((Goldman and Kuypers, *Development* 142, 3983-3995 (2015); Stacpoole et al., Stem Cell Reports 1, 437-450 (2013)).

Previous studies have generated OPCs from hPSCs using protocols that rely on embryoid body (Keirstead et al., *Neurosci.* 25, 4694-4705, (2005); Wang et al., Cell *Stem Cell* 12, 252-264 (2013)) or neurosphere (Douvaras et al., *Stem Cell Reports* 3, 250-259 (2014); Stacpoole et al., *Stem Cell Reports* 1, 437-450 (2013)) formation during a brief period of the differentiation. Since a biochemically and mechanically defined environment may offer opportunities for even more precise control over cell lineage specification (Takebe et al., *Cell Stem Cell* 16, 556-565 (2015)) (Engler et al., *Cell* 126, 677-689 (2006)), the development of a 3D biomaterial system for scalable OPC derivation was initiated. Specifically, differentiation was conducted in a PNIPAAm-PEG thermoresponsive hydrogel, which was previously shown is a highly effective system for hPSC expansion (Lei and Schaffer, *Proc. Natl. Acad. Sci. U.S.A* 110, E5039-48 (2013)). Solutions of this polymer are liquid at 4° C. but form a gel upon warming to 37° C., such that cells can be mixed with liquid at 4° C., become encapsulated in the material upon warming, be expanded or potentially differentiated at 37° C., and be readily recovered when the gel liquefies upon cooling. Importantly, not only does the resulting matrix support a scalable 3D culture, but this tunable system protects cells from shear and uncontrolled aggregation.

Figure 11A:
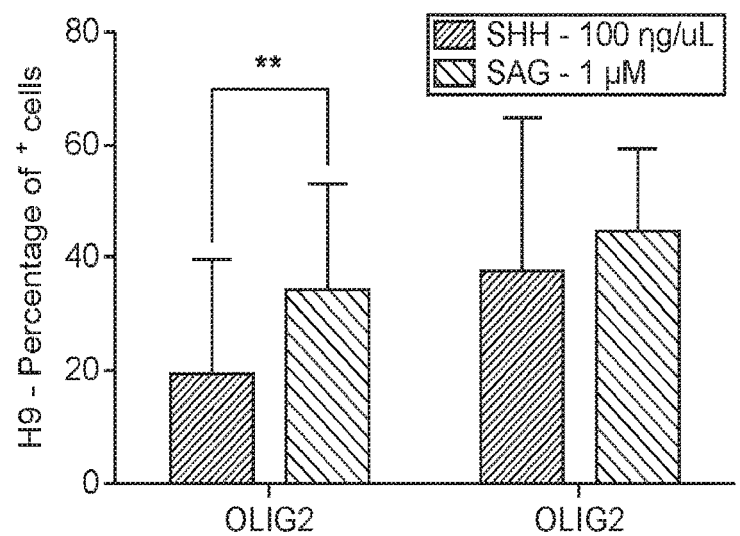
FIG. 11A-11B depict preliminary experiments comparing SHH to SAG for early OPC differentiation.
Figure 11B:
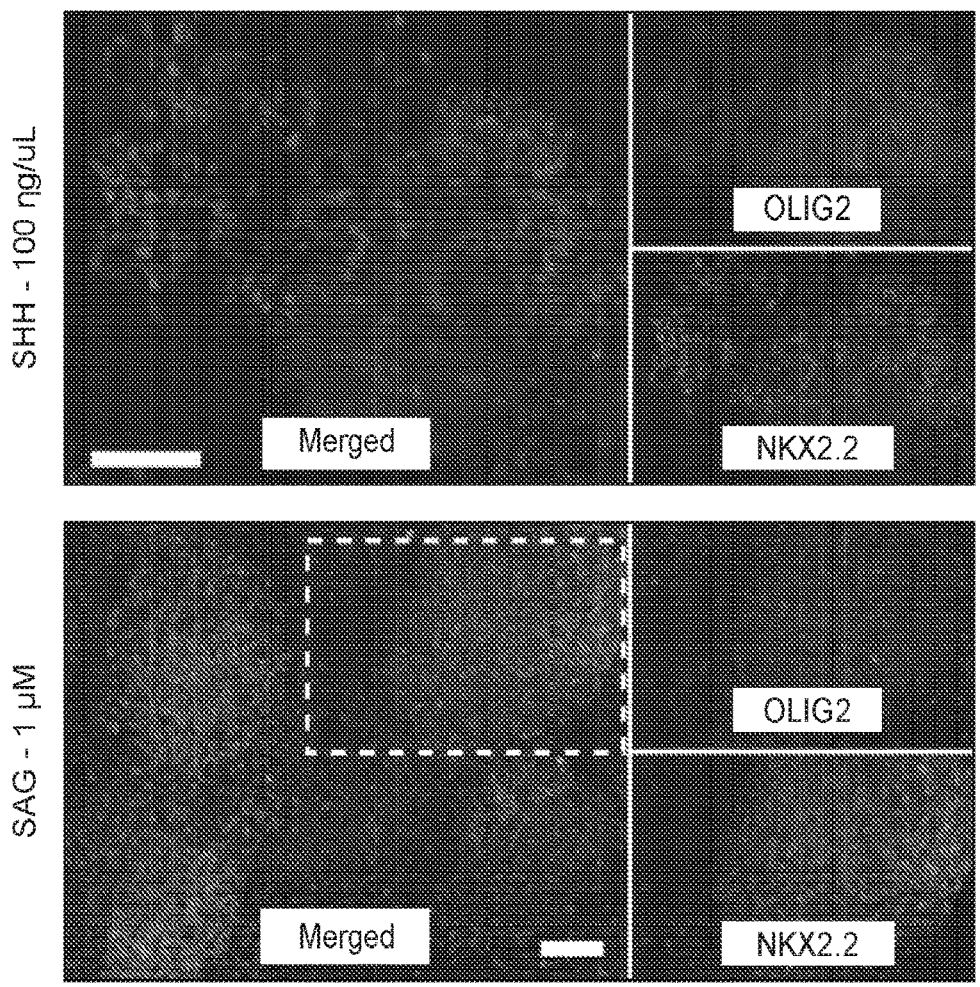

To differentiate OPCs from hPSCs in a scalable hydrogel-based system, seven culture conditions were designed based on: 1) the dual-SMAD inhibitors, SB431542 and LDN193189, which together facilitate neural patterning (Chambers et al., *Nat. Biotechnol.* 27, 275-280 (2009)); 2) SHH or Smoothened agonist (SAG), which promote neural tube ventralization (Briscoe and Ericson, *Cell Dev. Biol.* 10, 353-362 (1999); Chen et al., *Proc. Natl. Acad. Sci.* 99 14071-14076 (2002); Hu et al., *Nat. Protoc.* 4, 1614-1622 (2009a)); 3) RA, which enhances neural tube caudalization (Keirstead et al., *Neurosci.* 25, 4694-4705, (2005); Okada et al., *Dev. Biol.* 275, 124-142 (2004); Douvaras et al., *Stem Cell Reports* 3, 250-259 (2014); Stacpoole et al., *Stem Cell Reports* 1, 437-450 (2013)); and 4) CHIR99021, which promotes OLIG2 expression (Maury et al., *Nat. Biotechnol.* 33, 89-96 (2015)) (FIG. 4A). Following dual-SMAD induced neural specification, the impact of SHH vs. the small molecule SHH signaling agonist SAG was first assessed on hESC differentiation (FIGS. 11A-11B), and only minor differences in NKX2.2 and OLIG2 expression between these two conditions were seen (FIG. 11A-11B). SAG was thus utilized for all subsequent studies (specifically conditions 2-7), as it is more stable, and prior results indicate it may be more active than recombinant SHH in inducing OPC differentiation (Douvaras et al., *Stem Cell Reports* 3, 250-259 (2014)) (FIG. 4A). Furthermore, since both motor neuron and OPC development rely on OLIG2 expression (Park et al., *Dev. Biol.* 248, 356-368 (2002)), and since Wnt and RA signaling cooperate to specify human spinal motor neurons (Maury et al., *Nat. Biotechnol.* 33, 89-96 (2015)), the Wnt pathway activator CHIR99021 (a GSK inhibitor) and RA in was also included in the analysis (conditions 3, 4, and 5, and conditions 4, 5, 6 and 7, respectively). Finally, in addition to varying the SAG concentration (condition 5), the time of RA and SAG addition was varied (condition 6 and 7).

Initially, the NKX2.2-EGFP reporter enabled a very straightforward and marked distinction between conditions used for early OPC differentiation. Fluorescence analysis of the cell cultures in the biomaterial indicated a range of efficiencies for the differentiation (FIG. 4B), which was quantified longitudinally via using flow cytometry (FIG. 4C). Condition 6 had the highest levels of NKX2.2-EGFP, with a peak in expression at approximately day 14 (FIG. 4C). After 18 days of differentiation (FIG. 4D-4I), the conditions 5, 6, and 7 were found to be the most promising for early OPC differentiation, as NKX2.2-EGFP was expressed by 65%, 69%, and 50% of the cells differentiated in 3D using conditions 5, 6, and 7, respectively (FIG. 4G). Also, immunostaining analysis of the wild type and engineered NKX2.2 proteins together revealed a similar trend, with 79%, 81%, and 73% of the cells in conditions 5, 6, and 7, respectively, stained (FIG. 4H). Another other key early OPC marker, OLIG2, was expressed by 69%, 57%, and 61% of the cells in conditions 5, 6, and 7, respectively (FIG. 4B-4I). qPCR was then conducted to further characterize the expression of seven genes that regulate OPC patterning and analyzed the results with ClustVis, an in silico tool that enabled clustering of differentiation conditions with similar gene expression patterns at different time points using tree diagrams (Metsalu and Vilo, *Nucleic Acids Res.* 43, W566-70 (2015)). Consistent with the efforts to rapidly generate early OPCs characteristic of the first wave of OPC differentiation in the spinal cord, the results highlighted a strong patterning effect characteristic of RA-associated caudalization, as indicated by the bimodal clustering of the RA-containing conditions ($p<0.005$) (FIG. 4J), and by the expression levels of the early spinal cord marker HOXB4 in these conditions. This effect was also seen in ICC analysis of OLIG2 expression, where conditions with RA (conditions 4, 5, 6 and 7) had the highest percentage of OLIG2-expressing cells (FIGS. 4E-4F and FIG. 4I). Overall, the immunostaining (FIGS. 4B-4I) and qPCR (FIG. 4J) suggest cooperation between SAG and RA for early OPC patterning. Notably, among conditions 5, 6, and 7, only condition 7 had previously been used to differentiate OPCs, though exclusively on two dimensional (2D) systems (Douvaras and Fossati, *Nat. Protoc.* 10, 1143-1154 (2015); Douvaras et al., *Stem Cell Reports* 3, 250-259 (2014)), highlighting the promise of pairing new soluble media conditions with the 3D biomaterial. Finally, based on NKX2.2-GFP fluorescence and OLIG2 and NKX2.2 qPCR analysis, the addition of both SAG and RA on day 2 (condition 6) was more effective than starting SAG after the RA treatment (condition 7).

Figure 5A:
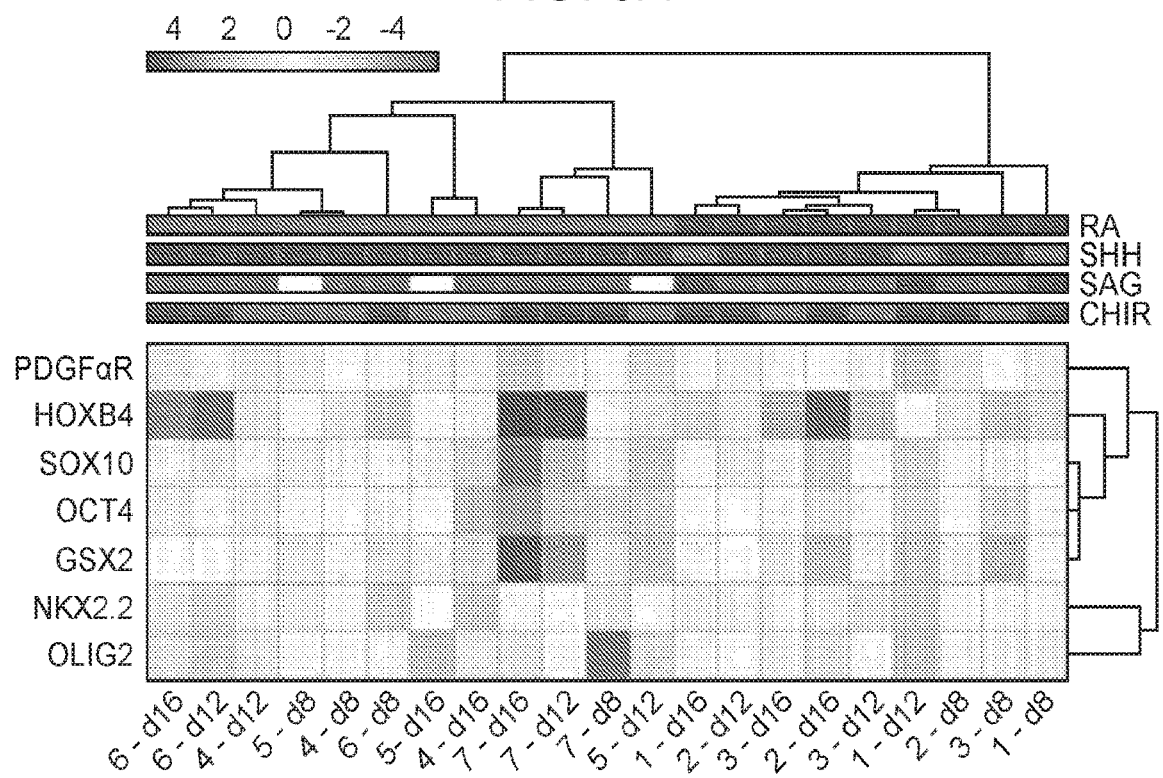
FIG. 5A-5I depict early OPC differentiation of hPSC lines.
Figure 5B:
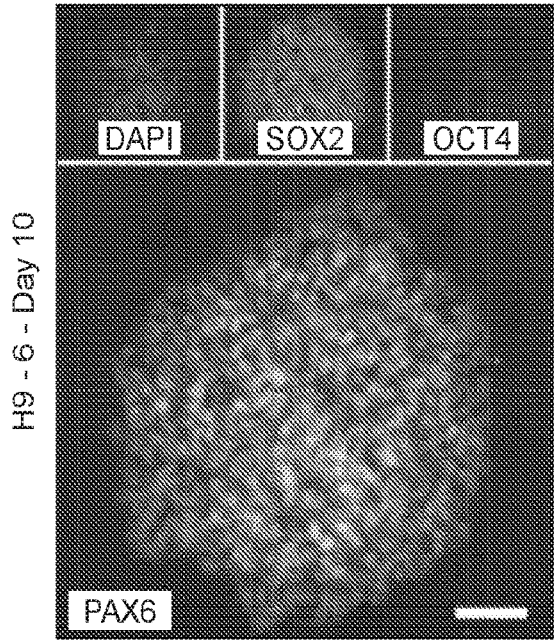
Figure 5C:
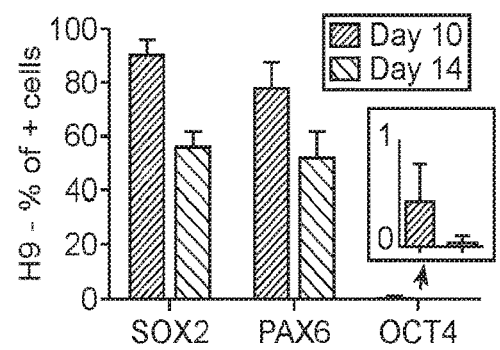

The 7 conditions were also tested for 3D differentiation of a different cell line, H9 hESCs. After qPCR-ClustVis analysis, a RA-based bimodal data clustering of the conditions was again seen, and a clear segregation of conditions that promoted NKX2.2 and OLIG2 gene expression was observed (FIG. 5A). Encouragingly, ICC analysis of H9 cells differentiated with condition 6, on days 14 and 18, revealed that the majority of cells (~80%) were expressing the NKX2.2 and OLIG2 OPC markers by day 18, while the number of cells expressing the KI-67 proliferation marker decreased over time indicating increased differentiation (FIG. 5B-5C). Because condition 6 resulted in the highest NKX2.2 and OLIG2 expression levels using both N30 and H9 hESCs, this medium composition was also tested for differentiation of TCTF hiPSCs. On days 14 and 18 of differentiation with condition 6, using both ICC and qPCR, high expression levels of NKX2.2 and OLIG2 (FIG. 5D-5F) was observed again. Therefore, the results with two additional hPSC lines again supported the potential of the 3D biomaterial culture system, in particular with soluble media condition 6, to promote OPC differentiation.

In sum, using the best condition with the 3D system, on day 18 57%, 84%, and 92% OLIG2+ cells was seen using N30, H9 and TCTF cells, respectively. By comparison, prior studies have observed approximately 70% OLIG2+ cells after differentiating hPSCs for 24 days (Stacpoole et al., Stem Cell Reports 1, 437-450 (2013)) or for 8 days (Douvaras et al., Stem Cell Reports 3, 250-259 (2014)), using a Matrigel-coated 2D surface. The best 3D culture media conditions was also assessed tusing a standard, Matrigel-coated 2D surface. After 20 days, 3D culture yielded ~3.5 times more cells overall than a 2D surface (p<0.0005) (FIG. 6C). Moreover, ICC analysis showed ~45% vs ~75% NKX2.2+ cells, and 29% vs 57% OLIG2+ cells, when comparing N30 cells differentiated in 2D vs 3D, respectively (FIG. 6A-6B). qPCR analysis further indicated increased levels of expression of these genes in 3D versus 2D at equivalent time points (FIG. 6D). These experiments indicated that combining the 3D PNIPAAm-PEG biomaterial with the novel differentiation condition offers the potential to improve early OPC differentiation compared to previously explored 2D systems.

Taken together, these results illustrate how modulating the factors that govern early patterning can enhance early OPC differentiation. In particular, the advantages of adding SAG and RA early and simultaneously in the 3D differentiation were also shown in a manner not previously tested. Finally, after comparing cells differentiated in the defined and scalable 3D system, and cells differentiated in traditional 2D Matrigel-coated plates, it was demonstrated that 3D culture can enhance early OPC differentiation.

Figure 7A:
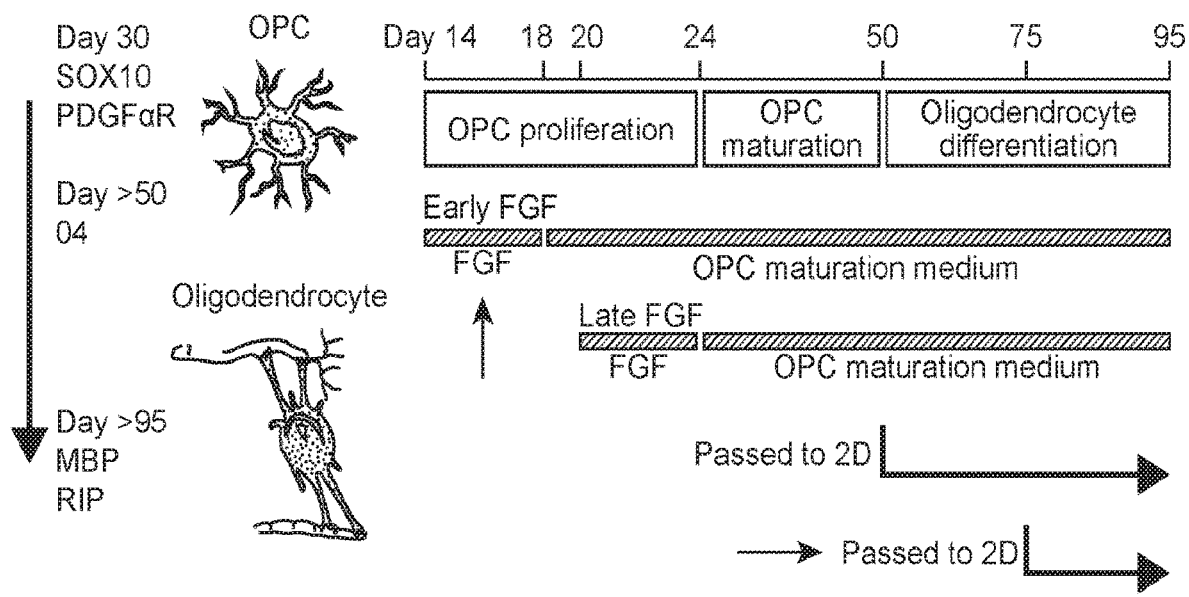
FIG. 7A-7I depict results showing that 3D differentiation enables oligodendrocyte maturation.
Figure 7B:
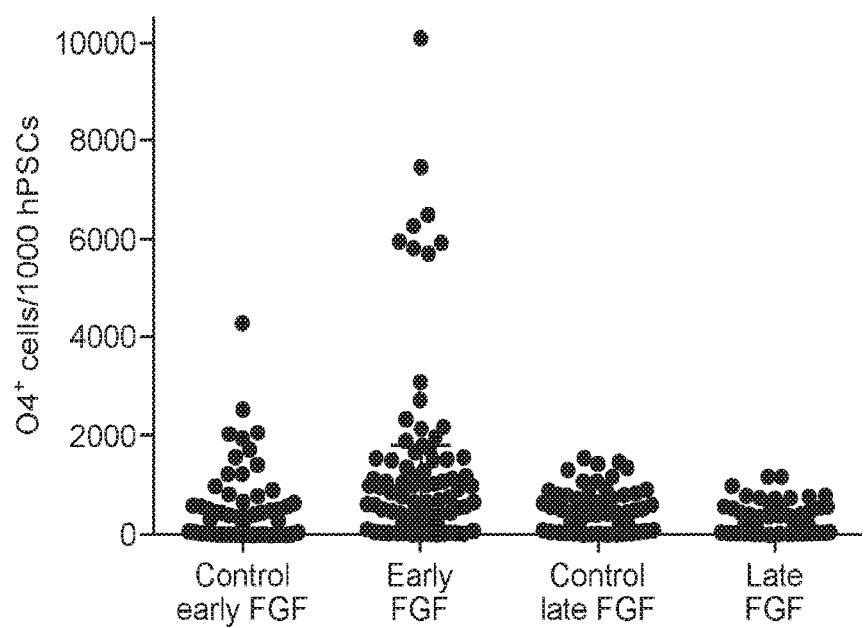

3D Culture Supports Oligodendrocyte Maturation into Electrophysiologically Active Cells After optimization of the initial 18 days needed for early OPC differentiation, the potential of 3D culture was assessed for subsequent specification of OPCs to the stage of maturation needed for biomedical applications. Based on prior work (Douvaras et al., Stem Cell Reports 3, 250-259 (2014)), a base maturation medium was used for this process (containing T3, PDGF-AA and NT-3, and other OPC specifying factors). In addition, basic fibroblast growth factor-2 (FGF-2) has been reported to enhance OPC expansion and maturation (Kang et al., Stem Cells 25, 419-424 (2007); Kerr et al., Int. J. Neurosci. 120, 305-313 (2010); Stacpoole et al., Stem Cell Reports 1, 437-450 (2013); Wang et al., Cell Stem Cell 12, 252-264 (2013)), though its role in human OPC differentiation has been unclear (Hu et al., Development 136, 1443-1452 (2009b); Stacpoole et al., Stem Cell Reports 1, 437-450 (2013); Wang et al., Cell Stem Cell 12, 252-264 (2013)). Furthermore, because it has been previously observed that early OPC markers expression can decrease within the first two weeks of cell differentiation (Douvaras et al., Stem Cell Reports 3, 250-259 (2014)), which was also noted (FIG. 4C and FIG. 12), it was hypothesized that adding FGF-2 or OPC maturation medium during this window had the potential to alleviate this issue. FGF-2 was added at day 14 or day 20, followed by the maturation medium (FIG. 7A). After adding FGF-2 daily from day 14 to day 18 and maturation medium thereafter (henceforward referred to as early FGF treatment), on day 24 OPC differentiation was similar to the analogous condition without FGF (FIG. 13A-13B); however, the number of cells expressing the OPC marker O4+ by day 95 interestingly increased (FIG. 7B). In contrast, adding FGF-2 from days 20-24 and OPC maturation medium thereafter resulted in ~4-fold fewer O4+ OPCs than with early FGF treatment (FIG. 7B). Hence, condition 6 was combined with early FGF treatment for all subsequent experiments.

Figure 7C:
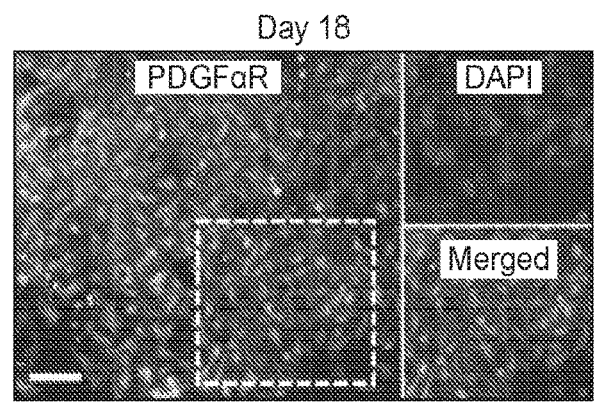
Figure 7D:
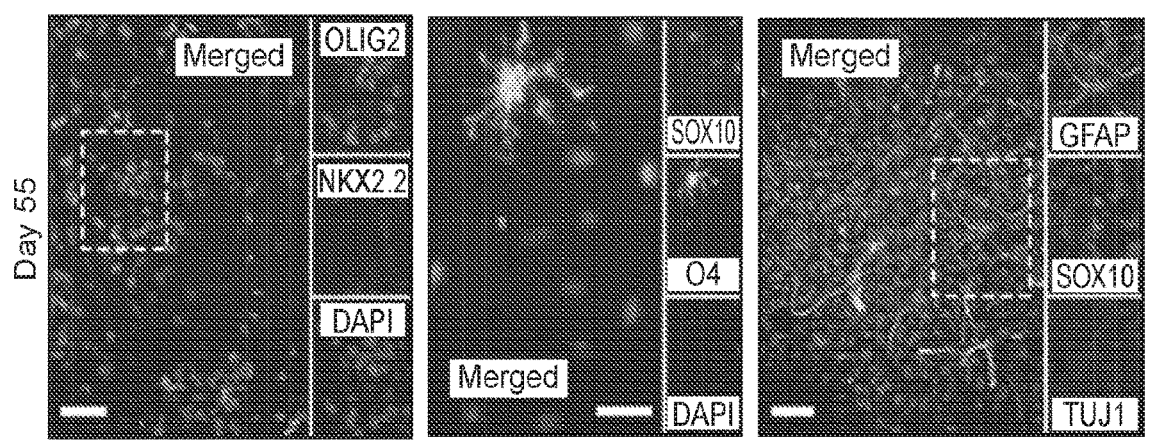
Figure 7E:
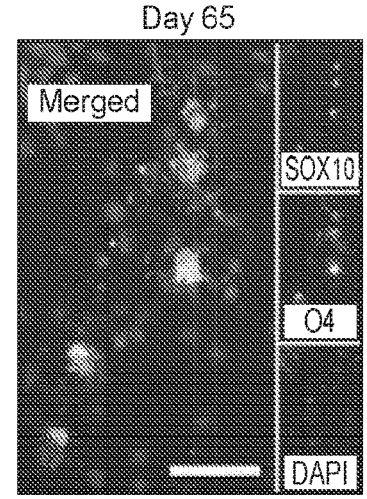
Figure 7F:
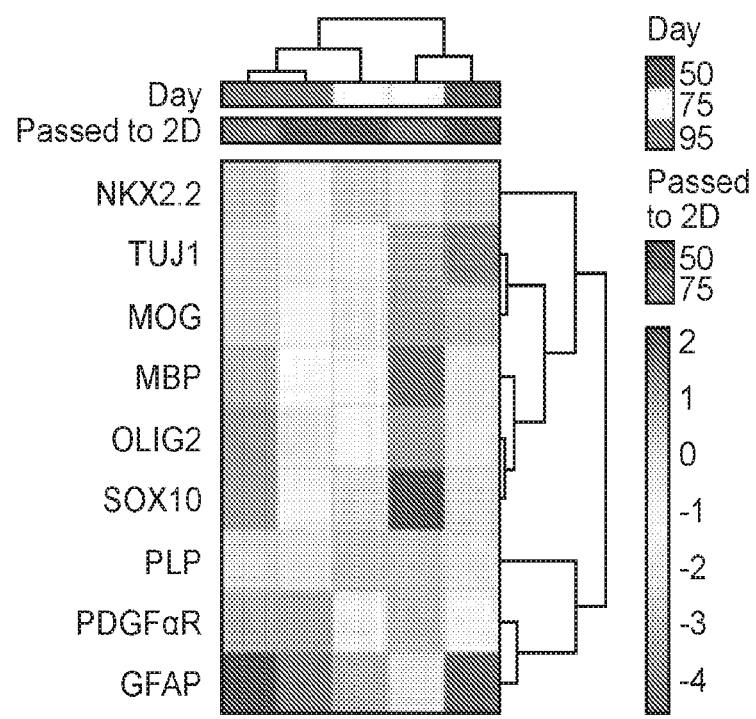

Having defining an advantageous set of conditions for late stage OPC maturation, OPC maturation markers was longitudinally analyzed in greater detail on days 18, 55, and 65 (FIG. 7C-7E). First, expression of the OPC marker PDGFαR was detected by day 18 (FIG. 7C). In addition, following 55 days of the differentiation, NKX2.2 and OLIG2 were still expressed by most cells (~70%), and the key OPC marker SOX10 was expressed by ~60% of cells (FIG. 7D). Moreover, O4 expression was first observed on day 55 (FIG. 7D), and the number of O4+ cells progressively increased thereafter (FIG. 7E). Importantly, because proliferative and migrating OPCs are better suited for transplantation, in general cells that express SOX10 but not yet the more mature OPC marker O4 are at an appropriate developmental stage for implantation (Goldman and Kuypers, Development 142, 3983-3995 (2015)), which for the current 3D differentiation system apparently corresponded to day 50 cells (FIG. 7D and FIG. 7F).

Figure 7G:
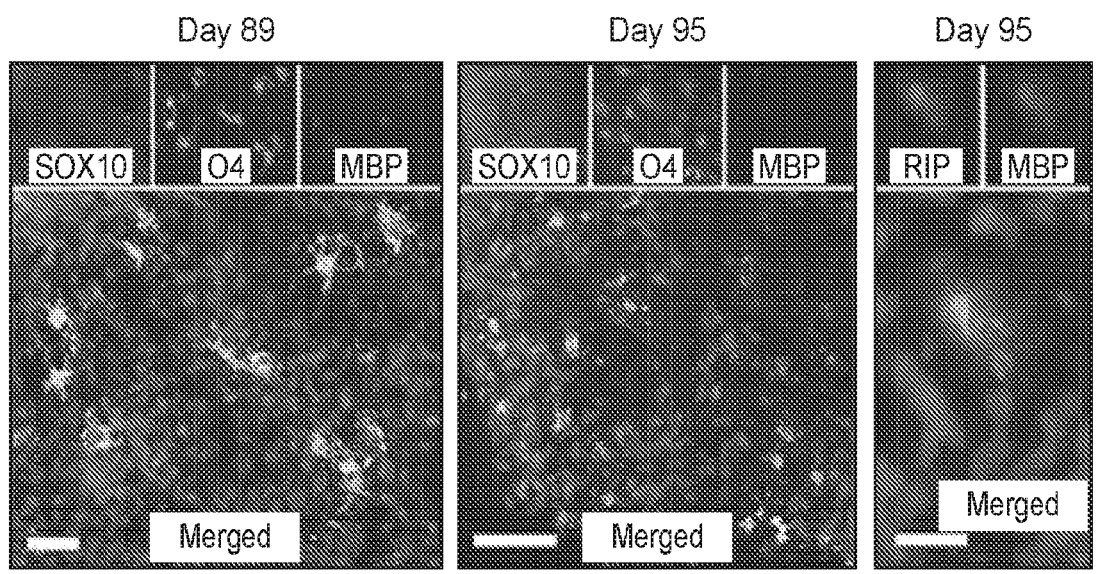
Figure 7H:
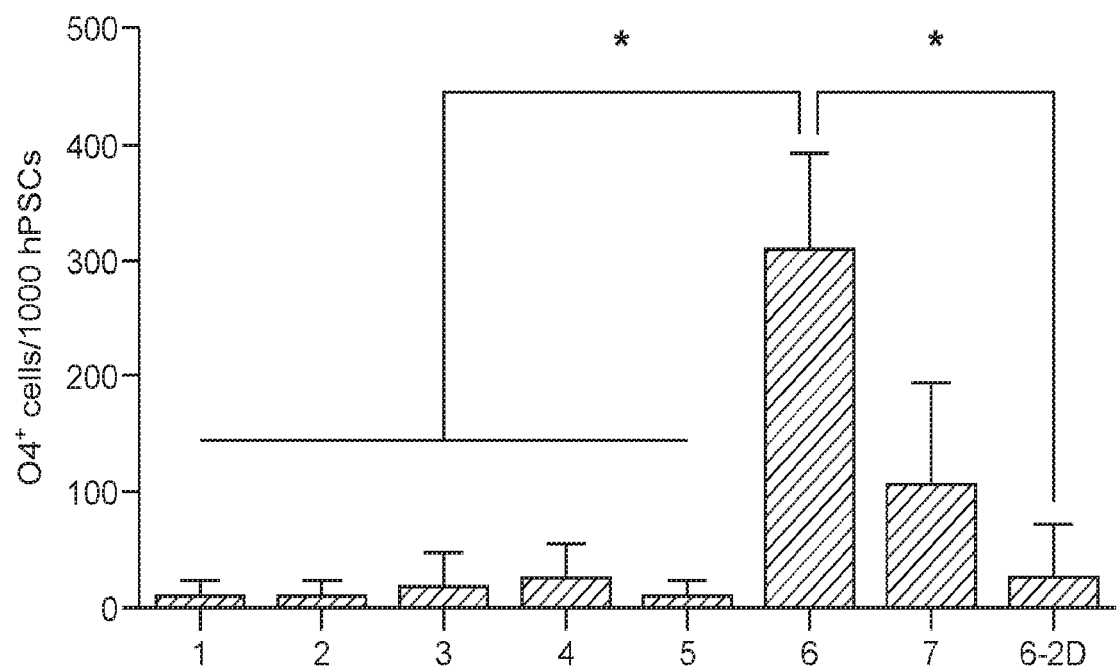

In addition to generating OPCs with the appropriate developmental maturity for transplantation studies, it was investigated whether these cells had the potential to develop into even more mature OPCs and oligodendrocytes, which would have implications for the scalable 3D production of OPCs and oligodendrocytes for drug discovery, disease modeling, or other studies that depend on mature cultures. (Najm et al., Nature 522, 216-220 (2015)). A 95-day protocol was used that incorporated condition 6 for early OPC differentiation, the early FGF treatment for OPC maturation, and transfer onto 2D on day 75 for late stage OPC differentiation. qPCR analysis on days 50, 75 and 95 showed a progressive increase in the expression of OPC and oligodendrocyte markers over time (FIG. 7F). Notably, ICC analysis revealed a longitudinal increase in the number of cells expressing O4 and confirmed the presence of mature oligodendrocytes, as evident in myelin basic protein (MBP) and RIP expression after completion of the differentiation timeline (FIG. 7G). Moreover, supporting the initial premise that early stages of the differentiation may impact the long term maturation of OPCs, at day 95 it was observed at least 2-fold more O4+ cells differentiated with condition 6 than with the other conditions tested (FIG. 7H). In addition, using condition 6 and the early FGF treatment for cells differentiated solely in 2D resulted in ~10 fewer O4+ cells by day 95, when compared to the optimized conditions for 3D differentiation (p<0.05) (FIG. 7H). At day 95, there were also comparatively low TUJ1+ neurons and GFAP+ astrocytes in the culture (FIG. 5I), which often are present in oligodendrocyte differentiating populations (Douvaras et al., Stem Cell Reports 3, 250-259 (2014); Wang et al., Cell Stem Cell 12, 252-264 (2013)).

Together, these results demonstrate the ability of the 3D system to generate mature OPCs and differentiated oligodendrocytes.

Figure 8A:
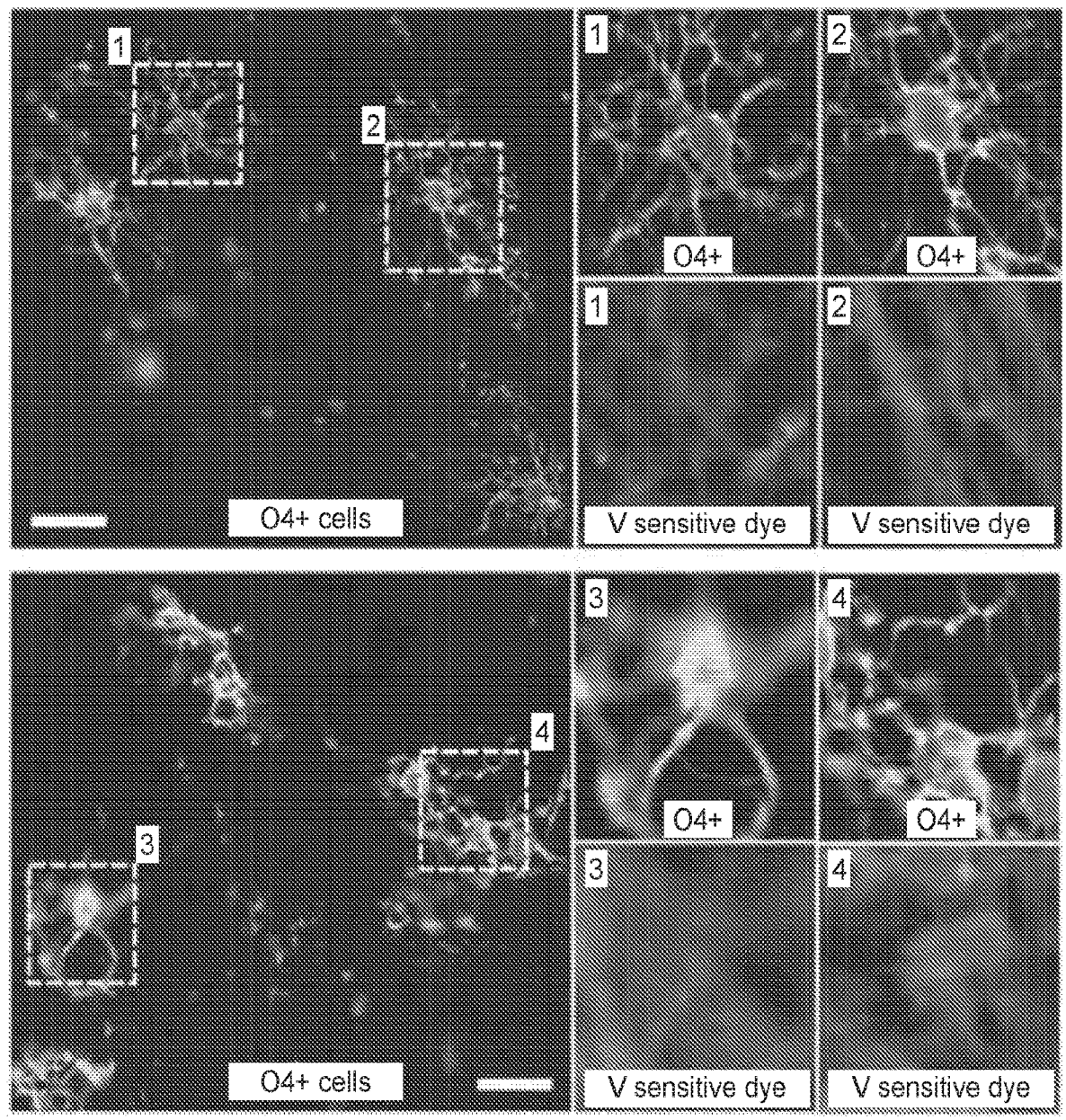
FIG. 8A-8B depict data showing that 3D differentiation generates firing and non-firing OPCs.
Figure 8B:
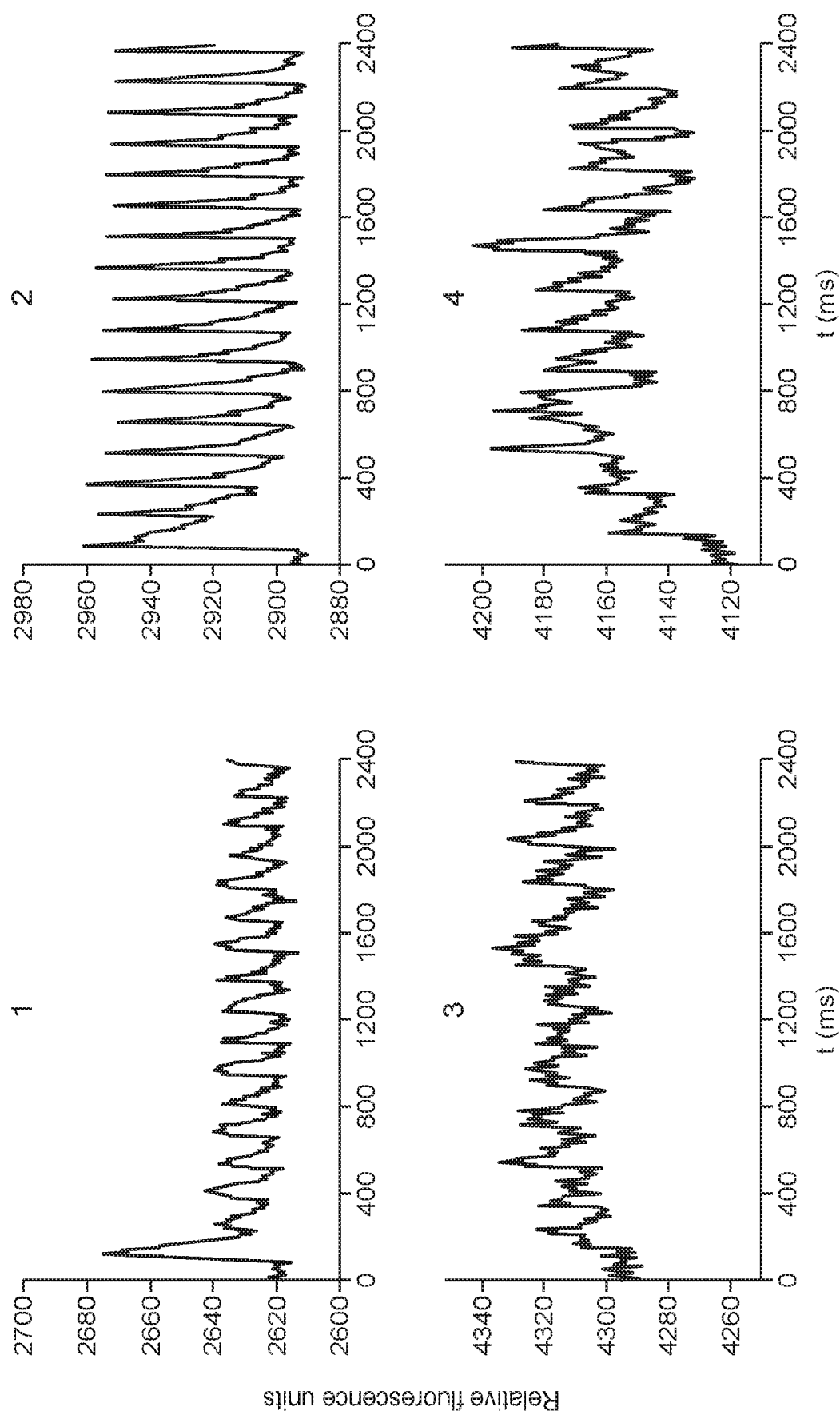

Electrophysiology Analysis of O4+ Cells Differentiated in 3D Reveals Spiking and Nonspiking OPCs An important developmental trait of maturing OPCs is their ability to fire action potentials upon stimulation, and both rodent (Káradóttir et al., Nat. Neurosci. 11, 450-456 (2008)) and human OPCs (Livesey et al., Stem Cells 34, 1040-1053 (2016); Stacpoole et al., Stem Cell Reports 1, 437-450 (2013)) have been reported to exhibit electrophysiological activity. Furthermore, due to changes in channel expression upon OPC maturation (Sontheimer et al., Neuron 2, 1135-1145 (1989)), and the progressive decrease in voltage-gated spiking activity of maturing OPCs in hPSC-derived OPCs (Livesey et al., Stem Cells 34, 1040-1053 (2016)), electrophysiology analysis offers a means for evaluating OPC maturation, i.e. it is effectively an early functional OPC marker. The electrical firing properties were investigated of cells generated in 3D (and then plated in 2D to enable the analysis), as a measure of OPC physiological maturity. Using a recently described voltage sensitive dye (Huang et al., J. Am. Chem. Soc. 137, 10767-10776 (2015)), the ability of 89-day-old cells to fire after excitation with a 1 ms pulse of a 60 V potential field was optically measured. Of the fifteen O4+ cells that were analyzed, twelve fired action potentials upon this excitation (presumably O4+/MBP-OPCs) (FIG. 8A-8B). This demonstrates that the hPSC-derived O4+ OPCs generated in 3D possessed electrophysiological properties similar to those previously reported for OPCs derived on 2D surfaces (Livesey et al., Stem Cells 34, 1040-1053 (2016); Stacpoole et al., Stem Cell Reports 1, 437-450 (2013)), indicating their potential to subsequently mature into functional oligodendrocytes.

Figure 9A:
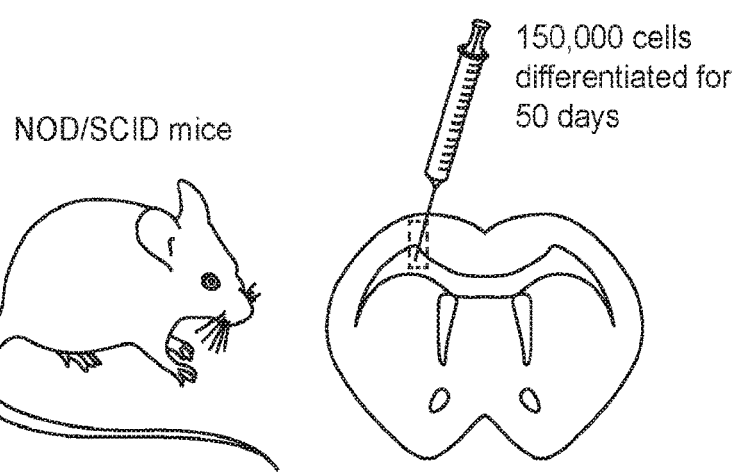
FIG. 9A-9I depict OPCs generated in 3D engraft, migrate and mature in vivo.
Figure 9B:
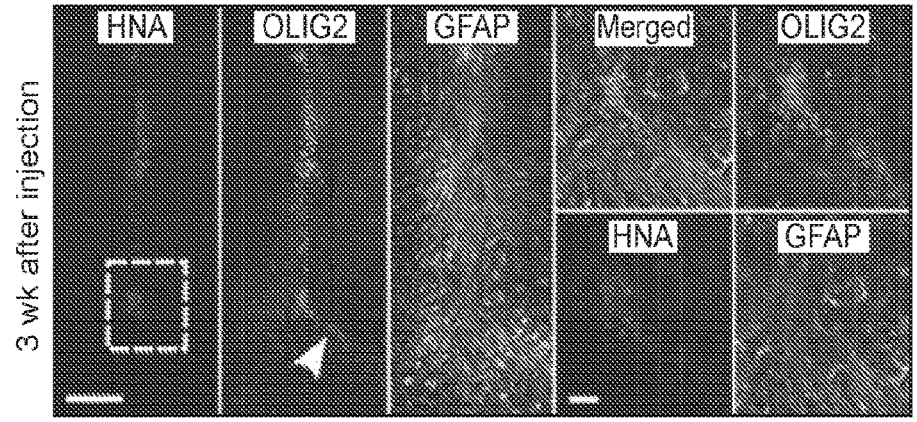
Figure 9C:
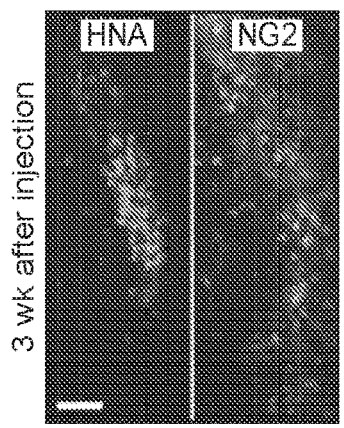
Figure 9D:
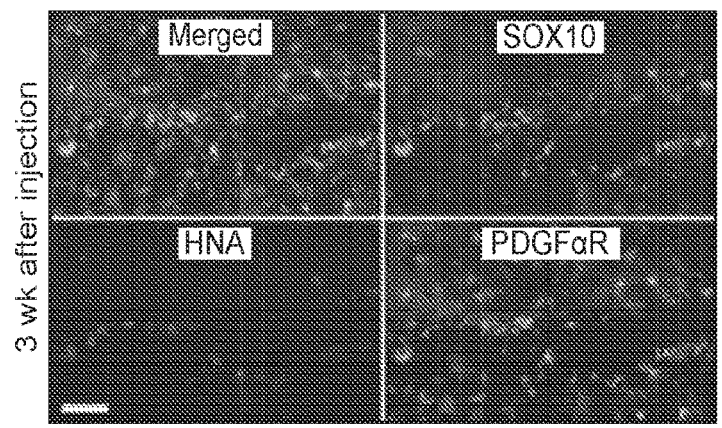
Figure 9E:
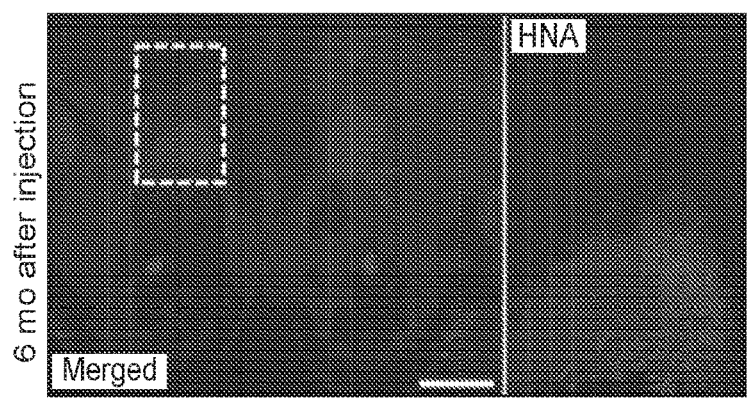
Figure 9F:
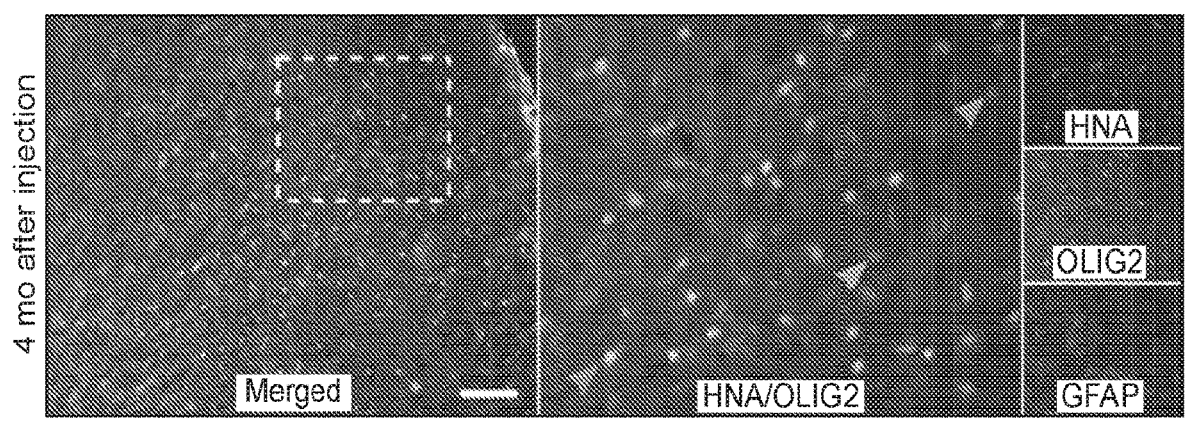
Figure 18:
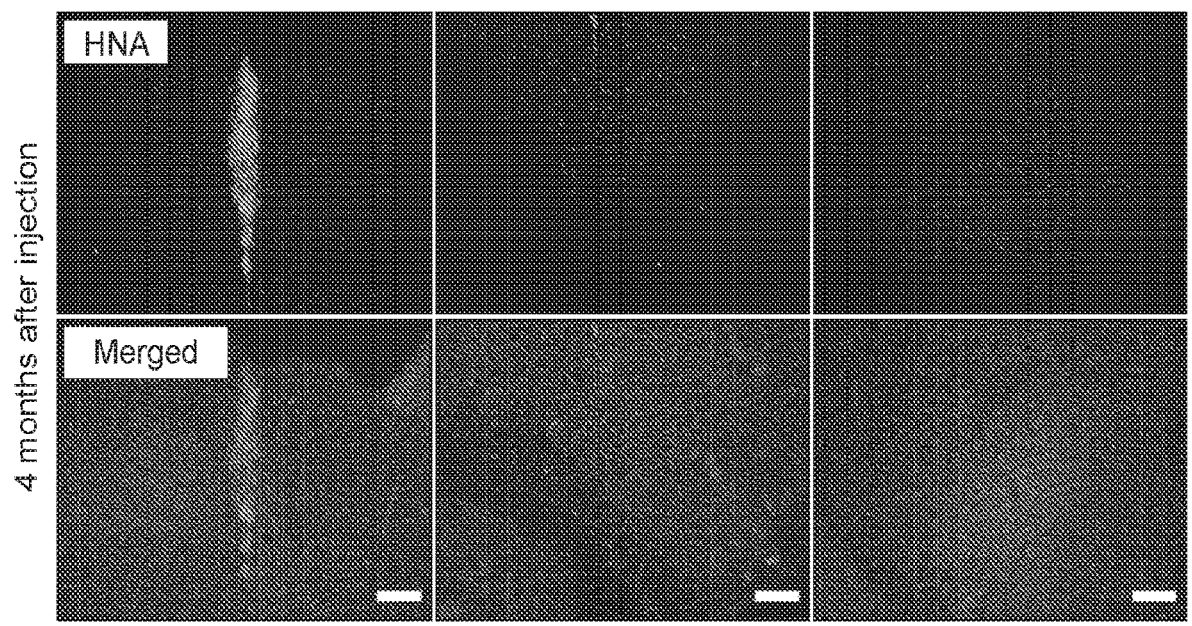
FIG. 18 depicts immunohistochemistry (IHC) analysis of brain tissue sections from NOD/SCID mice at 4 months after transplantation.

OPCs Differentiated in 3D for 50 Days Engraft, Migrate and Mature in the CNS after Transplantation into NOD/SCID Mice The next evaluation was to see whether OPCs generated in 3D were functional in vivo. Individual cell-spheres were harvested from the thermoresponsive 3D hydrogel for transplantation after 50 days of differentiation. In several prior studies, OPCs were isolated prior to implantation using an O4 antibody (Douvaras et al., Stem Cell Reports 3, 250-259 (2014); Wang et al., Cell Stem Cell 12, 252-264 (2013)); however, the high efficiency of OPC differentiation that was observed (~80% SOX10+ OPCs, FIG. 7D) led investigation of transplantation of cells in the absence of isolation. ~150,000 cells were implanted, into the corpus callosum of 30-day old NOD/SCID mice via a unilateral stereotaxic injection (FIG. 9A). Three weeks after injection, immunohistochemistry (IHC) analysis of forebrain sections from treated mice revealed the presence of HNA+ human cells that expressed OPC markers PDGFαR, NG2, OLIG2, and SOX10 at the injection track and the corpus callosum (FIG. 9B-9D). After four months, cells within the injection track were found as well as implanted cells that had migrated extensively throughout the corpus callosum and cortex (FIG. 18). Importantly, ~75% of the examined HNA+ cells throughout the brain expressed the OPC- and oligodendrocyte-specific marker OLIG2 (FIG. 9D), and relatively few expressed the astrocyte marker GFAP (FIG. 9B and FIG. 9F). Six months after injection, it was found that >90% of HNA+ cells had moved away from the injection site and dispersed fully into the corpus callosum and cortex, which is a migratory signature of OPCs (Goldman and Kuypers, 2015) (FIG. 9E).

Figure 9G:
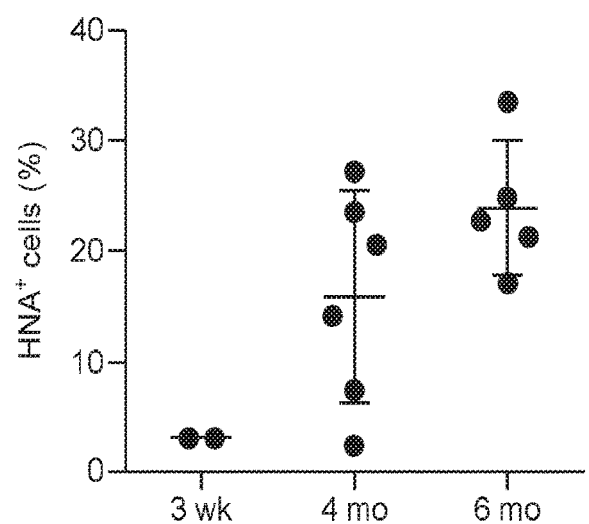

While previous studies did not examine the extent of graft survival in a longitudinal manner, the prevalence of the transplanted cells was measured over time. Specifically, the number of HNA+ cells present was counted in the brain 3 weeks, 4 months, and 6 months after injection. The numbers of HNA+ cells at both four and six months were ~6× higher than at three weeks, indicating that OPCs have the capacity to proliferate in vivo (FIG. 9G). Importantly, there were no signs of tissue overgrowth, since even after 6 months the number of human cells was still smaller than the number initially implanted, and there was no cell migration into the contralateral hemisphere. A small percentage of HNA+ cells were identified in the cortex that expressed both SOX10 and MBP (~15%) (FIG. 9H and FIG. 9I), a result that has not been previously reported and that suggests that the 50-day OPCs have the potential to mature into myelin producing cells in vivo. Collectively, these results demonstrate that OPCs differentiated in the 3D biomaterial system can engraft, migrate within the brain and mature into MBP+ cells.

In conclusion, a rapid, simple, and efficient approach was developed for generating OPCs by combining the benefits afforded by scalable 3D culture with hESC reporter line guided optimization.

FIG. 1 depicts a schematic of the differentiation protocol for pre-oligodendrocyte precursor cell patterning from pluripotent stem cells in a PINIPAAm-PEG based culture system.

FIG. 2A-2B depict a time-course analysis of Olig2 and NKX2.2 expression using different conditions for pre-oligodendrocyte precursor cell differentiation. FIG. 2A shows micrographs of Olig2 and NKX2.2 expression in cells that experienced different differentiation conditions. FIG. 2B shows the expression level of Olig2 and NKX2.2 in cells that experienced different differentiation conditions.

Figure 3D:
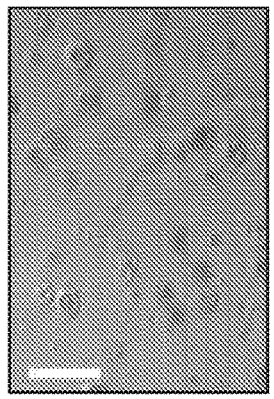
Figure 3E:
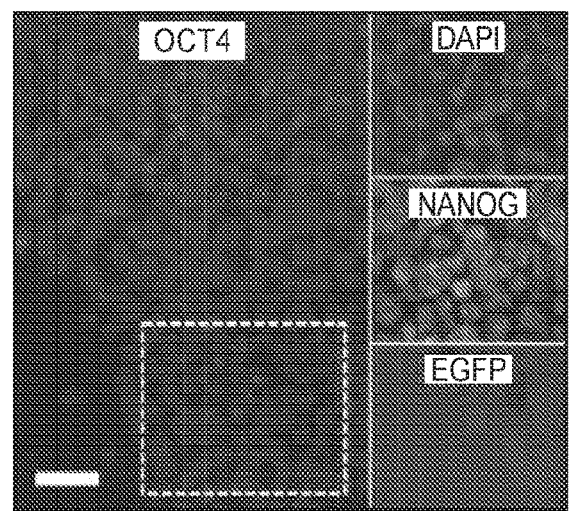
Figure 3F:
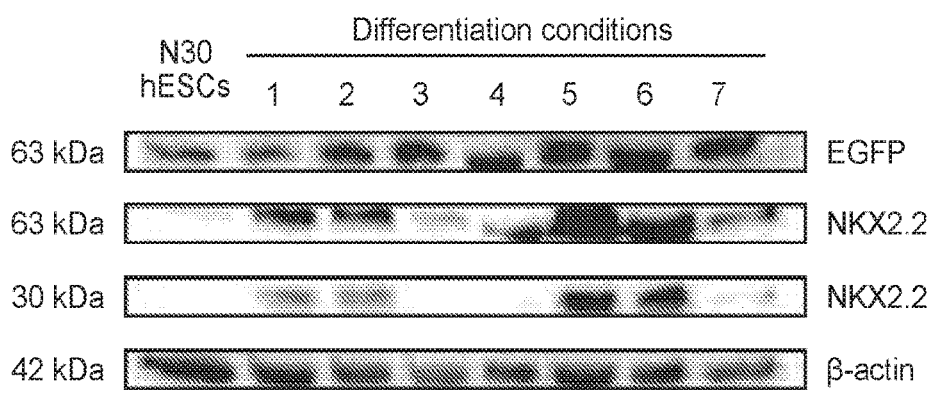

FIG. 3A-3F depict generation of an NKX2.2-EGFP hESC reporter line. FIG. 3A shows a schematic of the gene targeting strategy used to generate reporter cells. The top cartoon depicts the strategy to optimize early OPC differentiation using CRISPR-Cas9 genome engineering, and the bottom cartoon indicates the structures of the donor plasmid and the NKX2.2 locus before and after gene targeting. Genetic elements are not displayed to scale. FIG. 3B shows normalized luciferase activity in HEK293T cells co-transfected with a reporter plasmid containing four repeats of the NKX2.2 binding site sequence upstream a luciferase reporter gene along with an expression vector encoding either wild-type NKX2.2 or NKX2.2-EGFP. FIG. 3C shows southern blot of puromycin-resistant WIBR3 hESCs after electroporation with the SpCas9-sgRNA expression vector and the NKX2.2-EGFP donor plasmid. Genomic DNA was digested with SacI and hybridized with a 32P-labeled EGFP probe (see FIG. 3A, bottom scheme) that detects a 3.2 kb fragment present only in gene-targeted clones. FIG. 3D shows phase contrast image of N30 cells grown in Mebiol gel for 5 days under expansion conditions. FIG. 3E shows immunocytochemistry analysis of NKX2.2-EGFP and the pluripotency markers OCT4 and NANOG in N30 cells after expansion in Mebiol. FIG. 3F shows western blot of cell lysate from N30 cells after differentiation for 20 days using multiple different conditions. Scale bars: 200 µm in FIG. 3D and 50 µm in FIG. 3E.

Figure 4B:
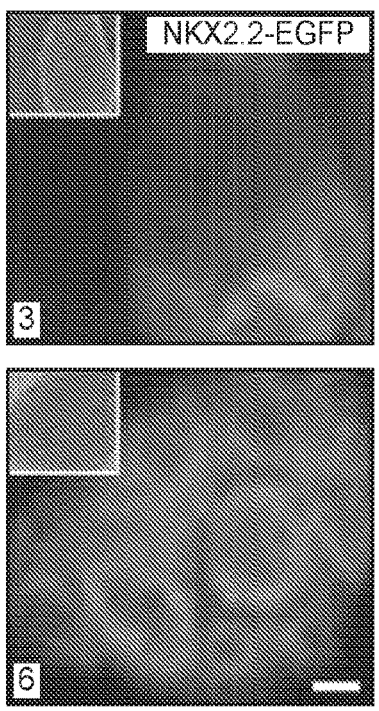
Figure 4C:
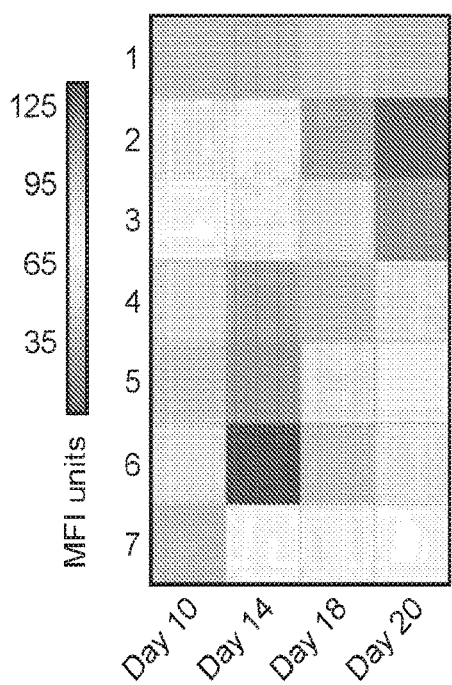
Figure 4I:
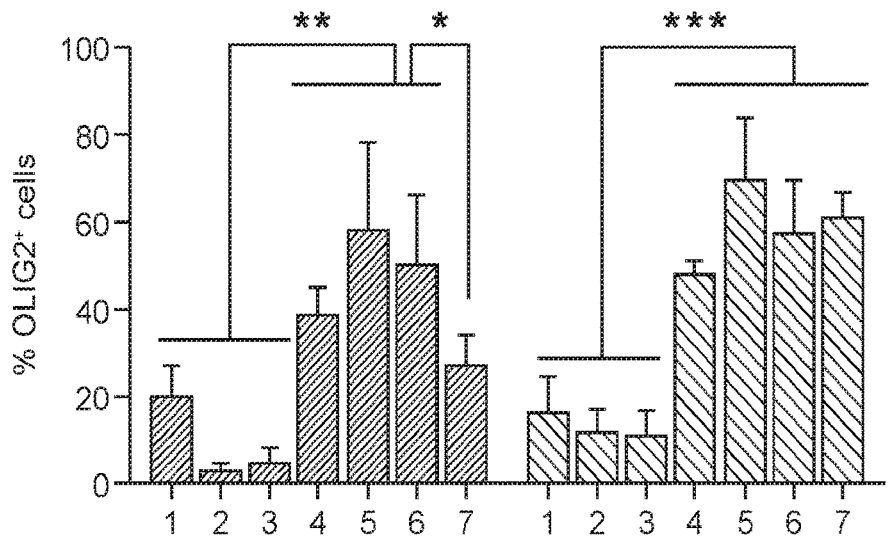
Figure 4J:
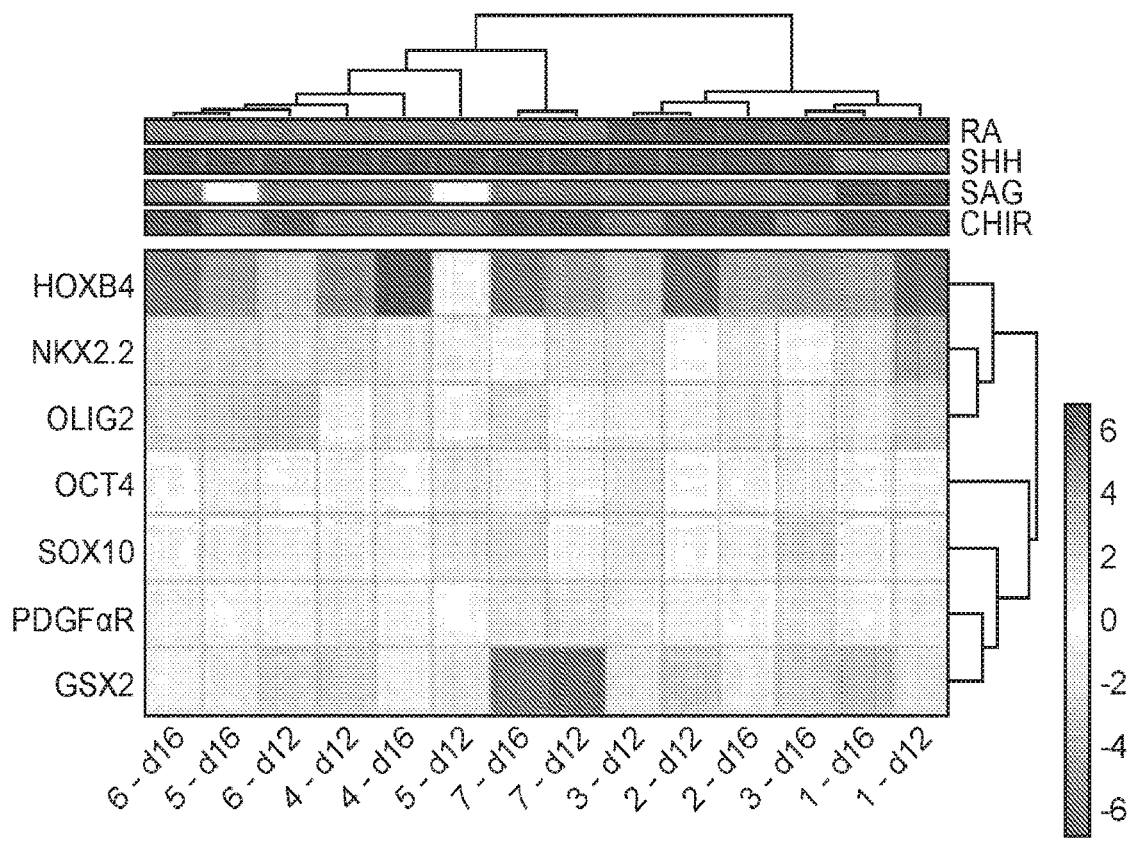

FIG. 4A-4J depict optimization of early OPC differentiation in 3D. FIG. 4A shows conditions used for early OPC differentiation. The left diagram indicates the different stages of development of early OPCs and the markers expressed during those stages. The right scheme depicts the different combinations of factors used for the differentiation. The best performing, condition 6, is highlighted with a black arrow. FIG. 4B shows analysis of NKX2.2-EGFP fluorescence after N30 cells were differentiated for 18 days in 3D using conditions 3 and 6. FIG. 4C shows a heat map illustrating NKX2.2-EGFP mean fluorescence intensity (MFI) after N30 cells were differentiated for 10, 14, 18 or 20 days using conditions 1-7. FIG. 4D-4F shows ICC analysis after N30 cells were differentiated for 18 days in 3D using condition 6 (FIG. 4D and FIG. 4F) and condition 3 (FIG. 4E). FIG. 4G-4I shows quantitative analysis of ICC using CellProfiler after N30 cells were differentiated for 14 and 18 days. The percentage of positive cells was normalized to DAPI-stained nuclei. FIG. 4J shows temporal ClustVis analysis of qPCR gene expression after N30 cells were differentiated in 3D. The concentrations of factors shown in the heat map caption are: RA (red=0 nM, blue=100 nM), SHH (red=0 ng/mL, blue=100 ng/mL), SAG (red=0 µM, white=0.5 µM, blue=1 µM) and CHIR (red=0 µM, blue=3 µM). Scale bars: 50 µm in B, D and F, and 100 µm in E. *P<0.05; P<0.01; *P<0.001 by Mann-Whitney test.

Figure 5D:
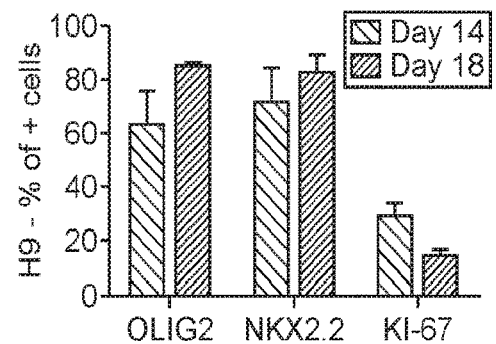
Figure 5E:
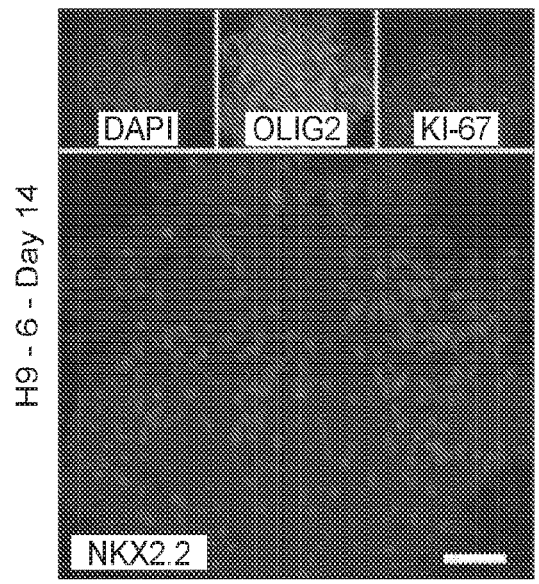
Figure 5F:
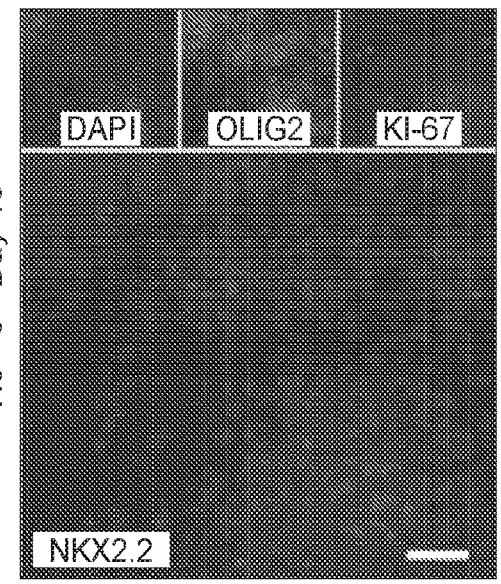
Figure 5G:
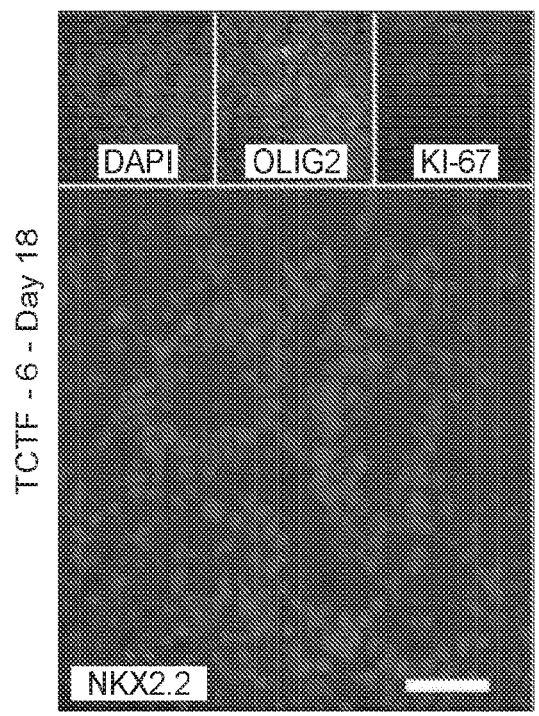
Figure 5H:
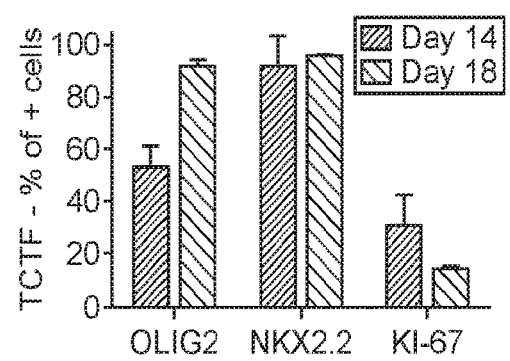
Figure 5I:
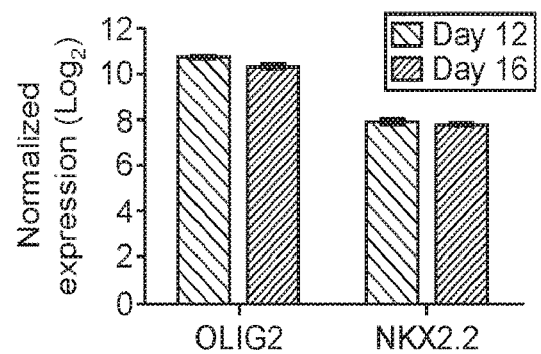

FIG. 5A-5I depict early OPC differentiation in hPSCs. FIG. 5A shows temporal ClustVis analysis of qPCR gene expression after H9 hESCs were differentiated in 3D. FIG. 5B shows ICC analysis of neural markers and the pluripotency marker OCT4 after H9 cells were differentiated in 3D for 10 days. FIG. 5C-5D shows Quantitative analysis of ICC using CellProfiler after H9 cells were differentiated for 10, 14 and 18 days. FIG. 5E-5F ICC analysis of early OPC markers and the proliferation marker KI-67 after H9 cells were differentiated in 3D for 14 and 18 days. FIG. 5G shows ICC analysis of early OPC markers and KI-67 after TCTFs were differentiated in 3D for 18 days. FIG. 5H shows Quantitative analysis of the ICC using CellProfiler after TCTFs were differentiated for 10, 14 and 18 days. FIG. 5I shows Temporal qPCR analysis of early OPC gene expression after TCTFs were differentiated for 12 and 16 days in 3D. Scale bars: 50 µm in FIG. 5B, FIGS. 5E-5F and FIG. 5G.

Figure 6A:
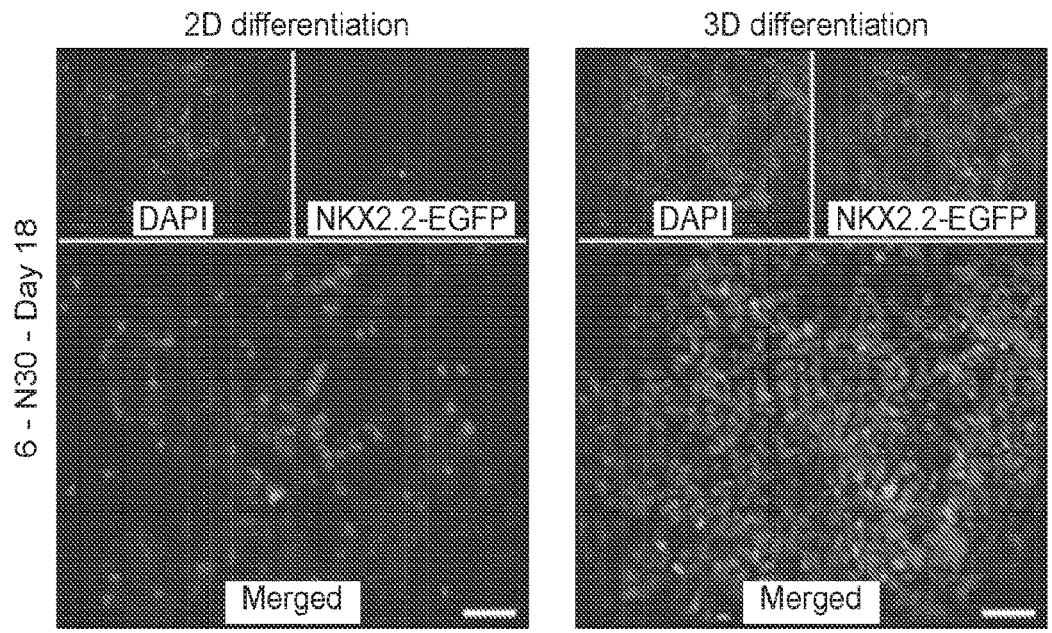
FIG. 6A-6D compare early OPC differentiation in 3D versus 2D.
Figure 6B:
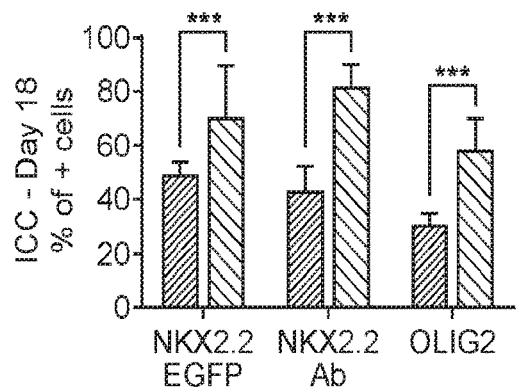
Figure 6C:
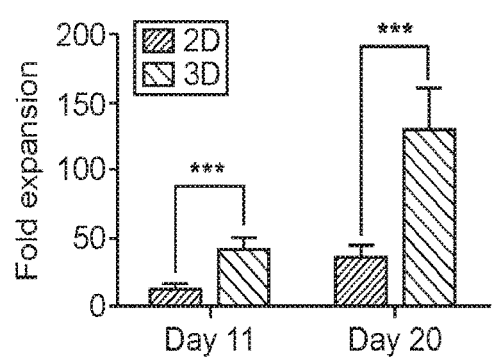
Figure 6D:
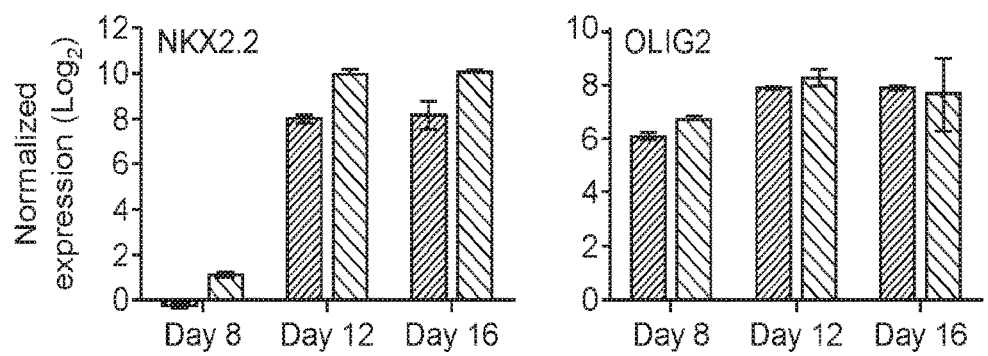

FIG. 6A-6D compare early OPC differentiation in 3D versus 2D. FIG. 6A shows ICC analysis after N30 cells were differentiated for 18 days using condition 6 on either Matrigel-coated 2D plates or 3D Mebiol hydrogel. FIG. 6B shows quantitative analysis of the ICC using CellProfiler after N30 cells were differentiated for 18 days in 2D or 3D. FIG. 6C shows temporal fold-expansion analysis of N30 cells differentiated in 2D or 3D for 11 and 20 days. Expansion was normalized to the number of cells seeded for differentiation. FIG. 6D shows temporal qPCR analysis of early OPC gene expression after N30 cells were differentiated for 8, 12 and 16 days in 2D or 3D. Scale bars: 50 µm in A. ***P<0.001 by Mann-Whitney test.

Figure 7I:
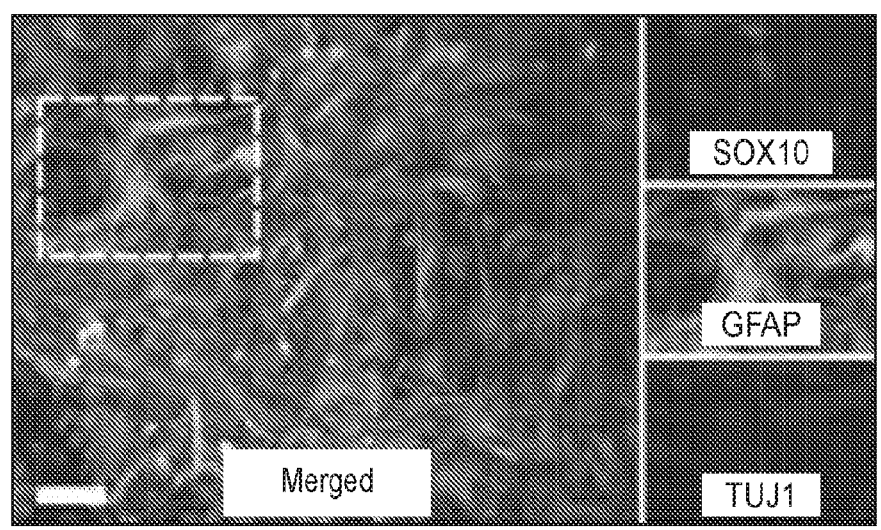

FIG. 7A-7I depict 3D differentiation enables oligodendrocyte maturation. (A) Conditions tested for OPC maturation. The left diagram illustrates different developmental stages for OPCs and oligodendrocytes, and lists their specific markers. The right scheme depicts the strategies used for oligodendrocyte maturation after the differentiation of early OPCs with condition 6. Early FGF, the best performing strategy, is highlighted with a black arrow. FIG. 7B shows quantification of O4 expression by ICC using CellProfiler after H9 cells were differentiated for 95 days using different strategies and passed onto 2D on day 75. FIG. 7C shows ICC analysis of H9 cells differentiated for 18 days using early FGF. FIG. 7D-7E shows ICC analysis of H9 cells differentiated for 55 and 65 days using early FGF. FIG. 7F shows qPCR analysis of OPC and oligodendrocyte gene expression in H9 cells differentiated for 50, 75 and 95 days. FIG. 7G and FIG. 7I show ICC analysis of H9 cells differentiated for 89 and 95 days using early FGF and passed onto 2D after 75 days of differentiation in 3D. FIG. 7H shows quantification of O4 expression analysis by ICC using CellProfiler after N30 cells were differentiated for 95 days using different early differentiation conditions in 3D or condition 6 in 2D. Cells were passed onto 2D on day 75. Scale bars: 50 µm in FIG. 7C-7D (left and right), FIG. 7E, FIG. 7G (left) and FIG. 7H; 20 µm in FIG. 7D (middle) and FIG. 7G (right); and 100 µm in FIG. 7G (middle). *P<0.05 by Mann-Whitney test.

FIG. 8A-8B depicts that 3D differentiation generates firing and non-firing OPCs. FIG. 8A shows multi-color epifluorescence imaging and voltage-sensitive dye fluorescence localized to the cell membrane of live-stained O4+ OPCs. Cells were differentiated for 89 days using condition 6 with early FGF and passed onto 2D on day 75. FIG. 8B shows action potential visualization of firing (1 and 2) and non-firing OPCs (3 and 4) after field stimulation using a 1 ms and 60 V pulse. Scale bars are 20 µm.

Figure 9H:
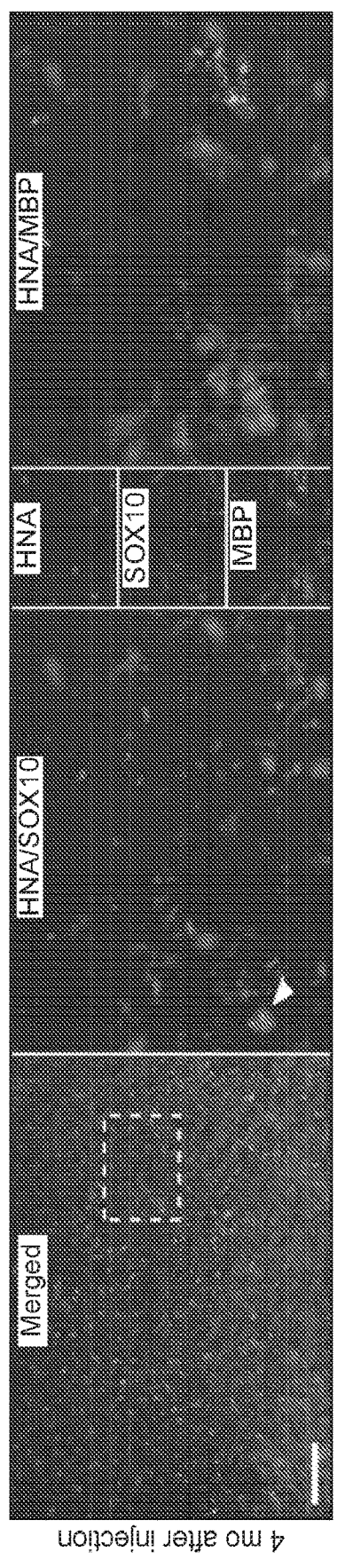
Figure 9I:
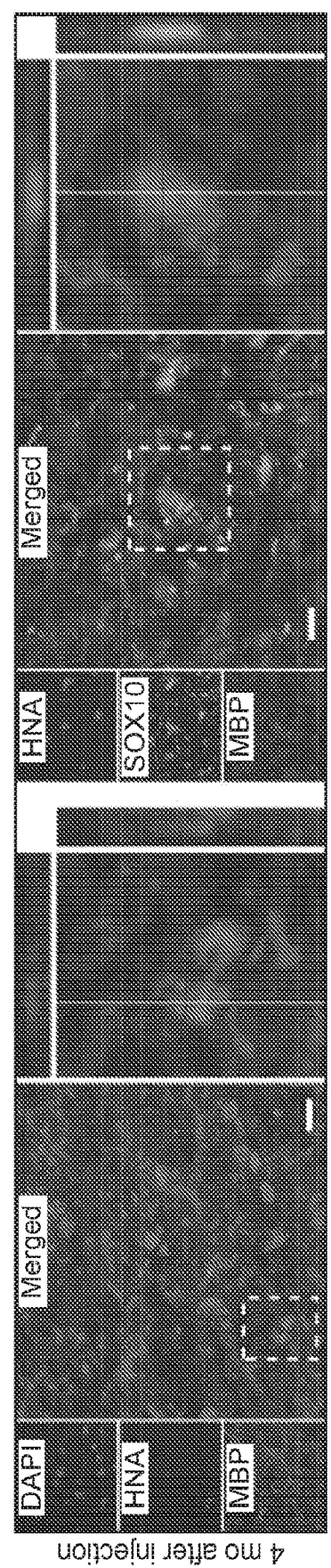

FIG. 9A-9I depicts OPCs generated in 3D engraft, migrate and mature in vivo. FIG. 9A shows a schematic illustration of the injection site in the corpus callosum of NOD/SCID mice. H9 cells were differentiated for 50 days in 3D using condition 6 with early FGF and transplanted as cell-spheres into 30 day old mice. FIG. 9B-D show immunohistochemistry analysis for the expression of human nuclear antigen (HNA) with FIG. 9B OLIG2, FIG. 9C NG2, FIG. 9D SOX10 and PDGFR in brain tissue sections from NOD/SCID at 3 weeks after transplantation. FIG. 9E-9I show IHC analysis of brain tissue sections from NOD/SCID at 4 and 6 months after transplantation. FIG. 9E shows HNA staining illustrating cell migration into the corpus callosum and across the cortex, away from the injection site. FIG. 9G shows quantification of the HNA+ cells that survived implantation at 3 weeks, 4 months and 6 months after transplantation, normalized to the number of cells injected (150 000 cells). FIG. 9F and FIG. 9H show IHC of HNA+ cells that co-express OLIG2, SOX10 and MBP. FIG. 9I Confocal z-stacks of HNA+ cells that co-express MBP and SOX10. Scale bars: 1 mm in FIG. 9G, 200 µm in FIG. 9B left, 100 µm in FIG. 9F and FIG. 9H, 50 µm in FIG. 9B right, FIG. 9C and FIG. 9D, and 10 µm in FIG. 9H.

Figure 10B:
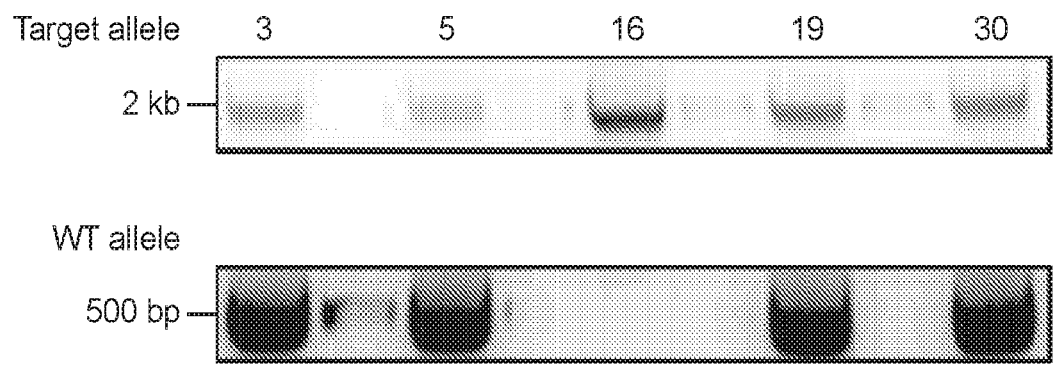

FIG. 10A-10B depict characterization of WIBR3 hESCs after gene targeting and puromycin selection. FIG. 10A shows the genomic PCR across the NKX2.2 locus. 36 puromycin-resistant WIBR3 hESCs clones were selected for analysis. FIG. 10B shows the genomic PCR assay to determine biallelic integration. WIBR3 clones were screened for specific integration by Southern blot analysis and then tested for integration copy number. Of the clones analyzed, only clone 16 appeared to have a biallelic modification.

FIG. 11A-11B. depict preliminary experiments comparing SHH to SAG for early OPC differentiation. FIG. 11A shows quantitative ICC analysis using CellProfiler after H9 hESCs were differentiated for 13 days. The percentage of positive cells was normalized to DAPI stained nuclei. FIG. 11B shows ICC analysis after H9 hESCs were differentiated for 13 days in 3D using preliminary medium conditions. Scale bars: 100 am in FIG. 11B.

Figure 12:
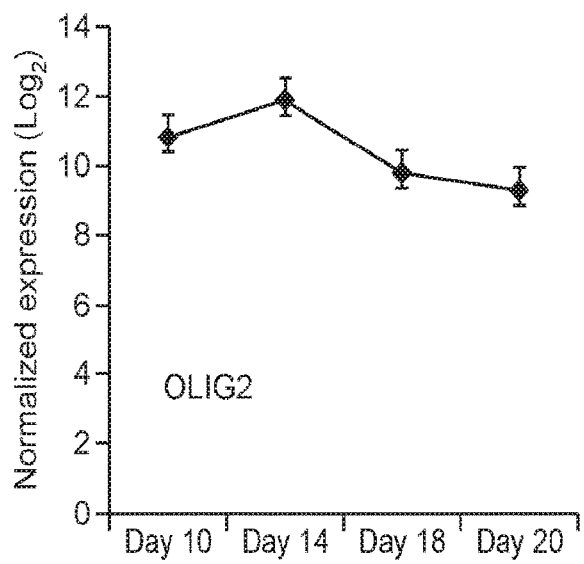
FIG. 12 depicts temporal qPCR analysis of early OPC gene expression in N30 hESCs differentiated using condition 6.
Figure 12:
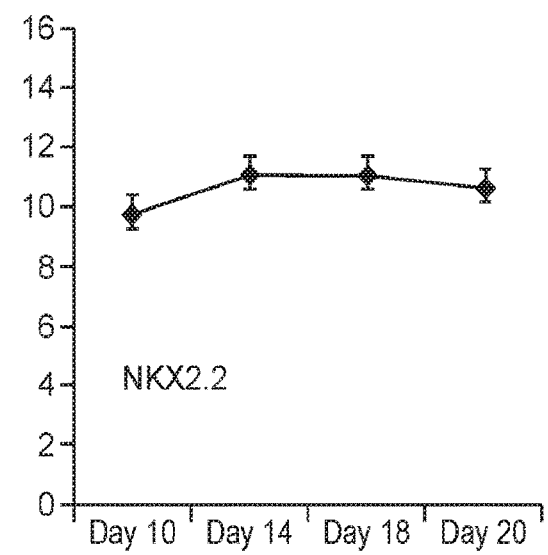
Figure 12:
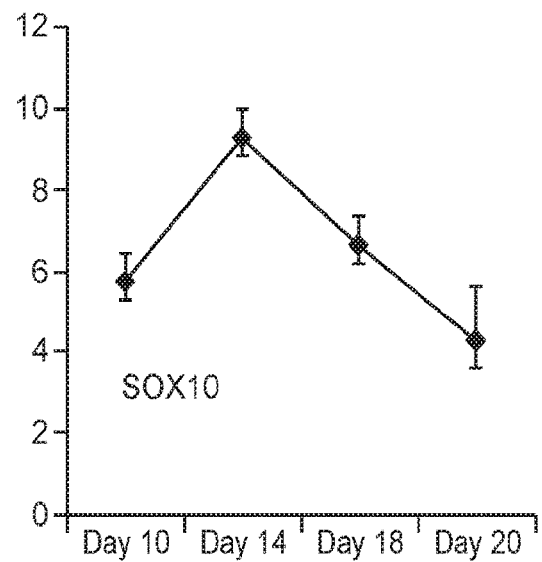
Figure 12:
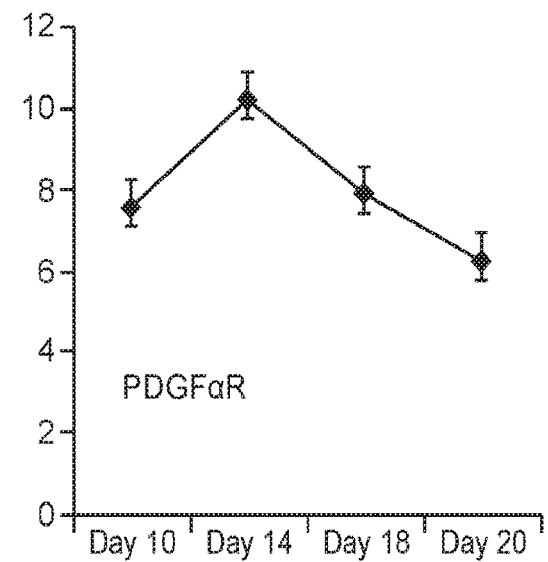

FIG. 12 depicts temporal qPCR analysis of early OPC gene expression in N30 hESCs differentiated using condition 6.

Figure 13A:
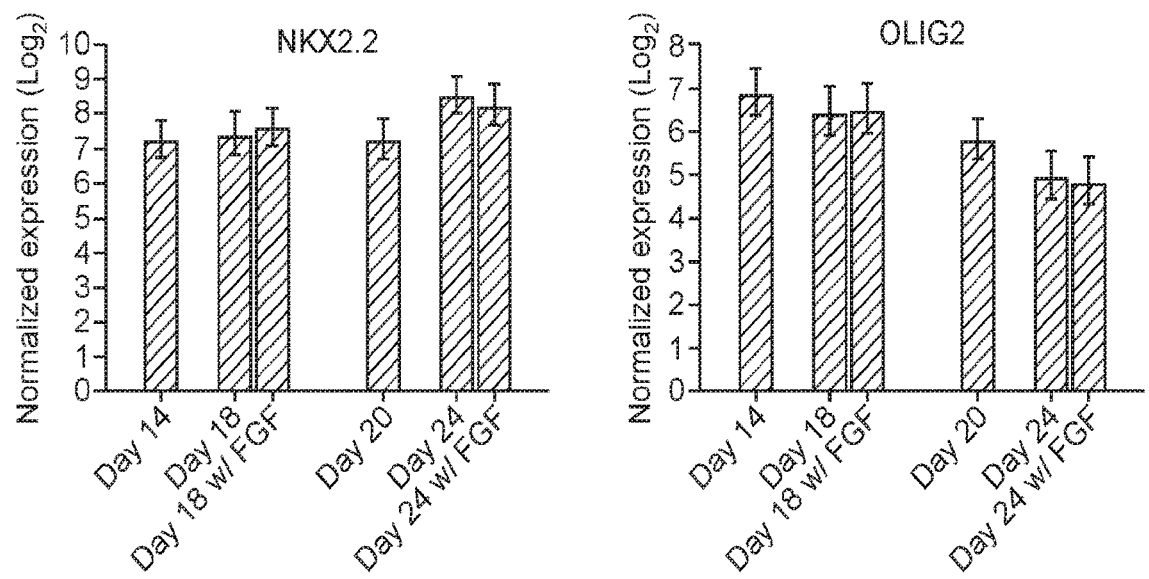
FIG. 13A-13B show the analysis of early OPC gene expression in N30 hESCs differentiated with condition 6 and different regimens of FGF supplementation.
Figure 13B:
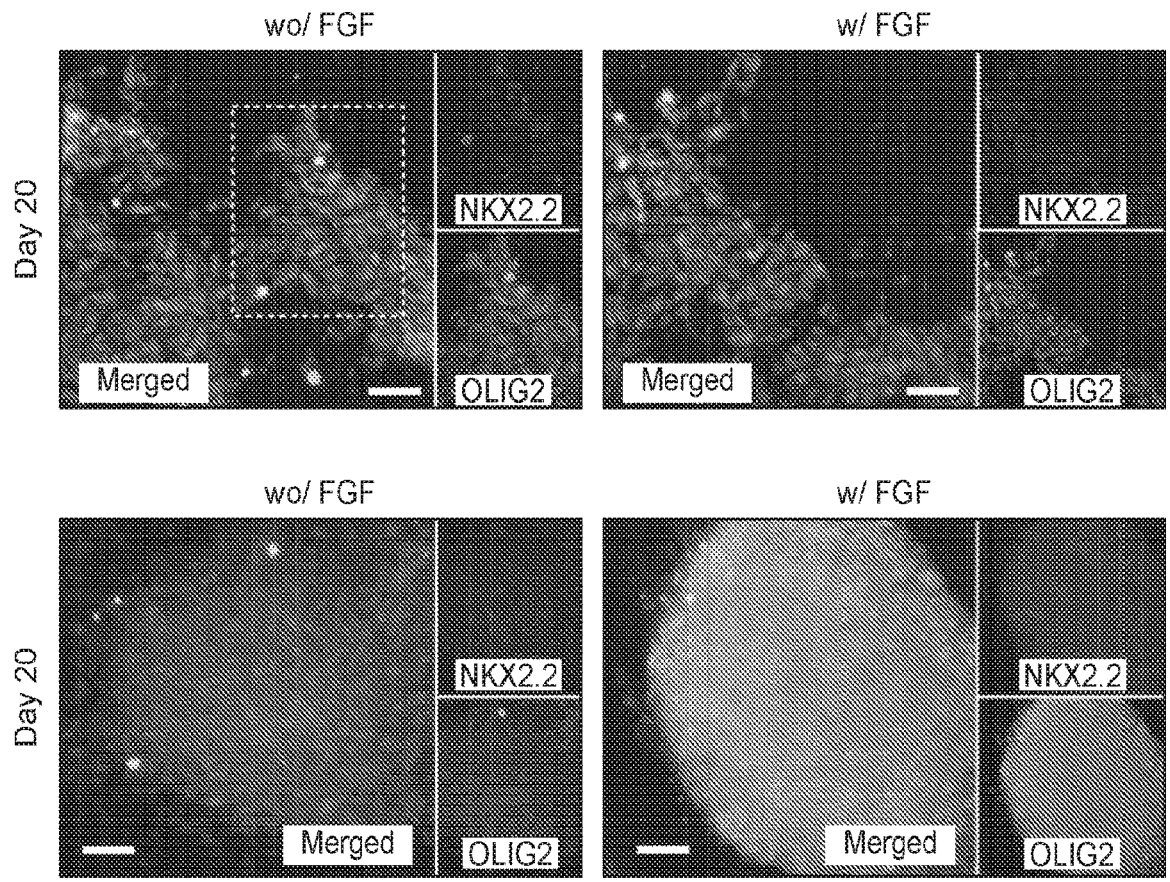

FIG. 13A-13B show the analysis of early OPC gene expression in N30 hESCs differentiated with condition 6 and different regimens of FGF supplementation. FIG. 13A shows temporal qPCR analysis of early OPC gene expression in H9 hESCs. FIG. 13B shows ICC analysis of H9 hESCs. Cells were differentiated in 3D using the medium regimen shown in FIG. 4A (condition 6) and FIG. 7A (early FGF vs late FGF). Scale bars in FIG. 13B: 50 µm in the top; 100 µm in the bottom images.

Figure 14A:
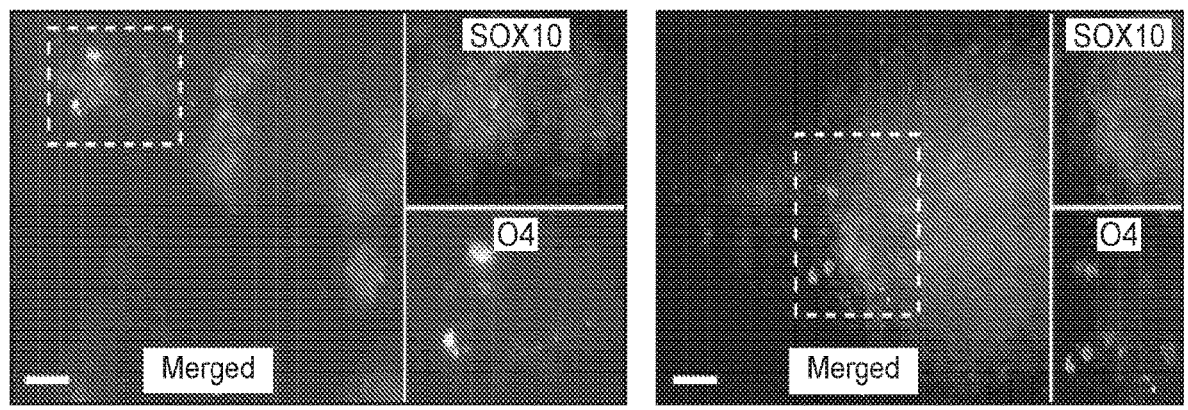
FIG. 14A-14B depict immunocytochemistry (ICC) analysis of cells differentiated for 15 additional days after freeze-thaw on day 50.
Figure 14B:
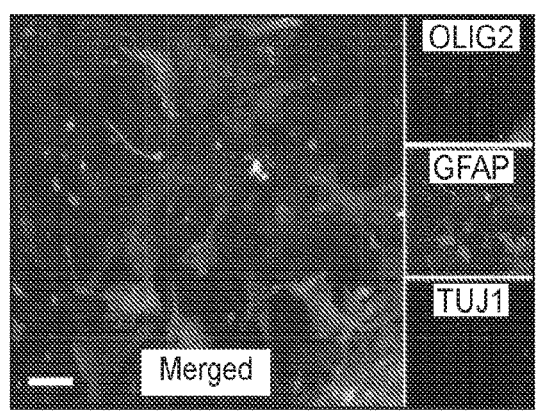

FIG. 14A-14B depict ICC analysis of cells differentiated for 15 additional days after freeze-thaw on day 50. Cells differentiated in 3D for ~50 days seemed to express the OPC markers that are characteristic of transplantation-quality OPCs (FIG. 7D and FIG. 7F) (Goldman and Kuypers, 2015). For this reason and because cell-product transport is critical for the success of cell therapies, before testing these cells in vivo, it was evaluated whether OPCs generated in 3D could withstand preservation. FIG. 14A) Cells were stained with the OPC markers SOX10 and O4. FIG. 14B) Cells were stained with the glial marker OLIG2, the astrocyte marker GFAP and the neuronal marker TUJ1. Scale bars: 100 µm in FIG. 14A; 50 µm in FIG. 14B.

Figure 15A:
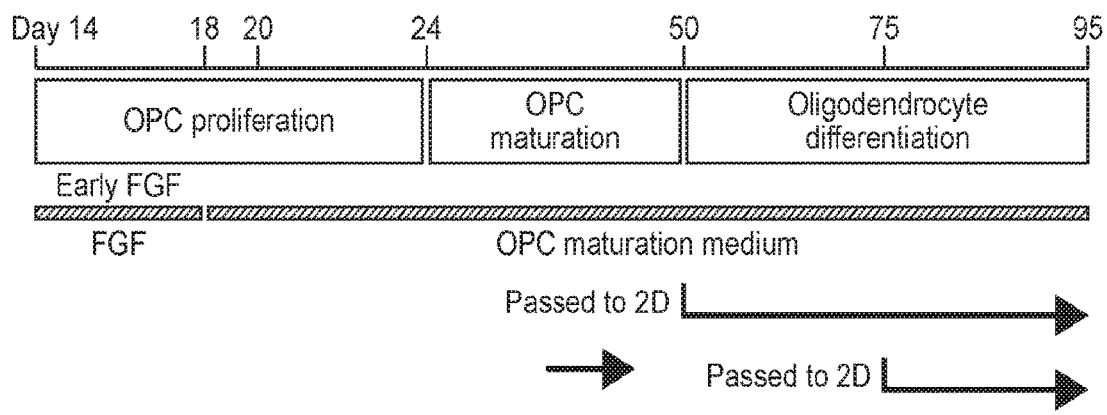
FIG. 15A-15B depict OPC maturation optimization—evaluation of the best time point for transferring cell spheres onto 2D
Figure 15B:
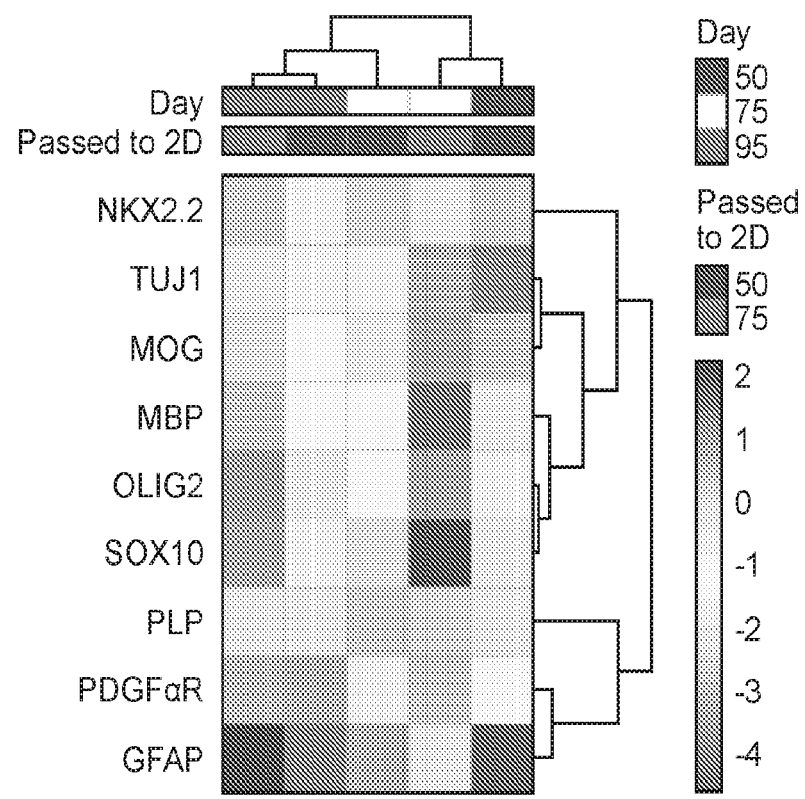

FIG. 15A-15B depict OPC maturation optimization—evaluation of the best time point for transferring cell spheres onto 2D FIG. 15A shows a schematic illustration of the 2 maturation strategies tested. Because OPC maturation is usually performed on 2D surfaces with low cell densities (Douvaras et al., 2014; Wang et al., 2013), whether transferring cells from 3D onto 2D laminin-coated surfaces was assessed on day 50 or on day 75 of the differentiation impacted OPC and oligodendrocyte maturation. The best performing strategy, passing cells onto 2D on day 75, is highlighted with a black arrow. FIG. 15B shows qPCR analysis of genes that regulate OPC and oligodendrocyte patterning combined with ClustVis processing, of H9 cells differentiated for 50, 75 and 95 days and passed onto 2D on either day 50 or 75, revealed that cells plated onto 2D after being cultured in 3D for 75 days had higher expression levels of OPC and oligodendrocyte genes.

Figure 16A:
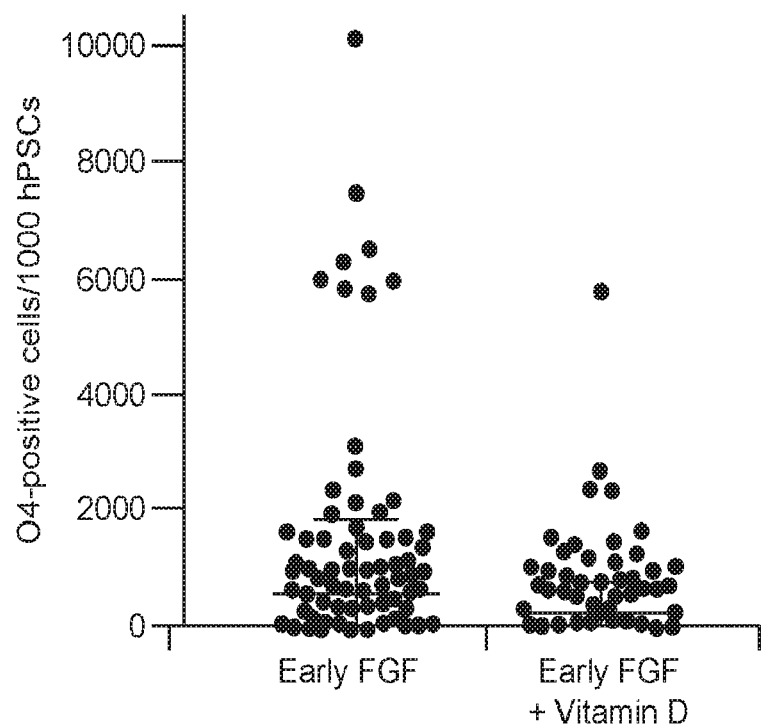
FIG. 16A-16C depict Vitamin D treated cells do not mature more efficiently.
Figure 16B:
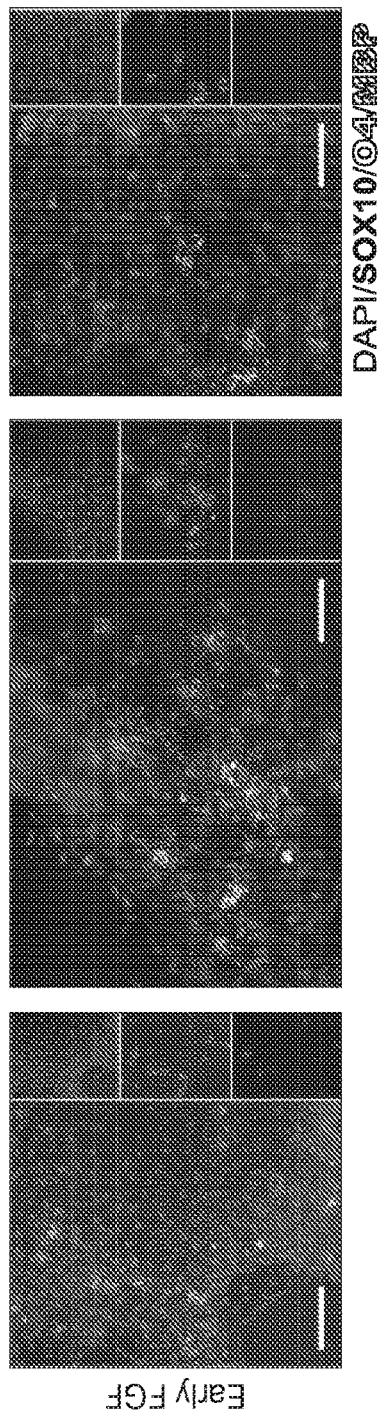
Figure 16C:
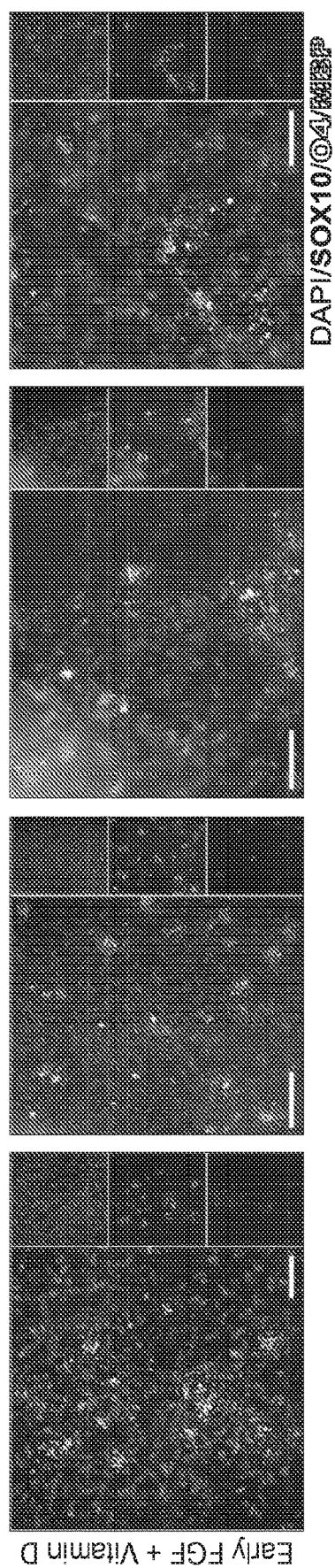

FIG. 16A-16C depict Vitamin D treated cells do not mature more efficiently. ICC analysis after differentiating H9 hESCs with condition 6 and early FGF for 75 days, and then passed onto 2D after an additional 20 days. Encouraged by a study where vitamin D enhanced OPC differentiation (de la Fuente et al., 2015), it was also evaluated whether it could improve late-stage OPC maturation; however, no increase in O4 expression was observed among treated cells. FIG. 16A) O4 expression as determined by ICC using CellProfiler in cells treated with 0.1 µM Vitamin D from day 66 to day 95. (FIG. 16B and FIG. 16C) Expression of OPC (SOX10 and O4) and oligodendrocyte (MBP) markers as determined by ICC using CellProfiler in cells cultured in the presence of absence of Vitamin D. Scale bars are: 50 µm on FIG. 16B (middle and right); FIG. 16C (left; middle right and right), and 100 µm on FIG. 16B (left) and FIG. 16C (middle left).

Figure 17:
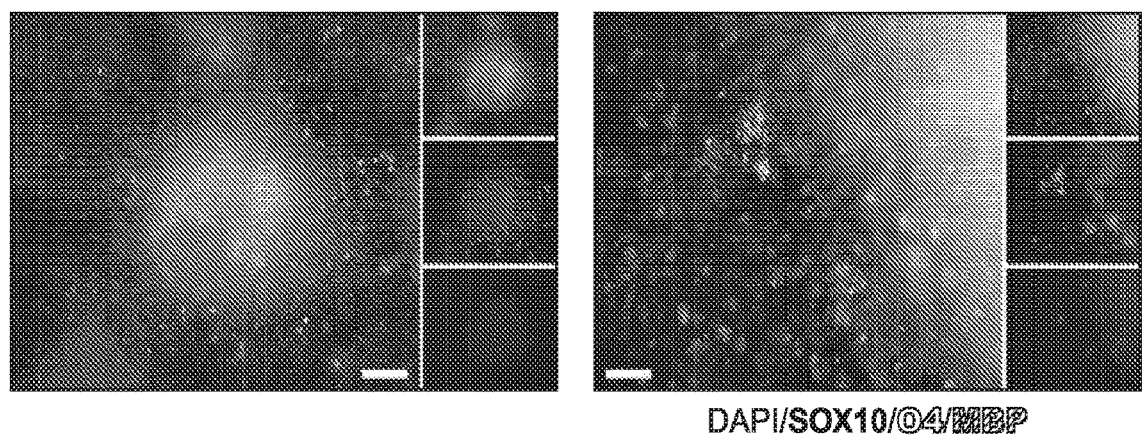
FIG. 17 depicts ICC analysis of cells after 72 days of differentiation.

FIG. 17 depicts ICC analysis of cells after 72 days of differentiation. Cells shown here are expected to be the in vitro equivalent of those imaged from mice 30 days after transplantation (FIG. 9B-9D). Both images show early expression of the oligodendrocyte marker MBP, which supports the potential of 3D culture for generating mature oligodendrocytes in an accelerated manner.

FIG. 18 depicts IHC analysis of brain tissue sections from NOD/SCID mice at 4 months after transplantation. HNA-positive cells were able to migrate and engraft within the corpus callosum and the cortex. Comparing to the last time point analyzed (6 months after transplantation), these show a higher concentration of transplanted cells near the injection site, whereas after 6 months most human cells had migrated more extensively.

FIG. 19 provides a table of primers used the present invention.

FIG. 20 provides a table with the composition of the media used for OPCs and oligodendrocyte differentiations. LF—Life Technologies; SK—Sellekchem; 1—used in condition 2; 2—used in conditions 2-7, at 0.5 µM in 5, and from day 8-17 in 7; 3—used in conditions 3-5; 4—used in conditions 4-7, and from day 0-17 in 7; 5—early FGF is day 11-17, late FGF is day 11-23 where FGF is added from day 20-23, and SAG and RA are maintained until days 23; 6—early FGF is from day 18-95 and late FGF is from day 24-95.

FIG. 21 provides a table of primary antibodies used for ICC and IHC.

FIG. 22 provides a table of primers used for qPCR.

REFERENCES

Abercrombie, M. (1946). Estimation of nuclear population from microtome sections. Anat. Rec. 94, 239-247.

Berger, M. F., Badis, G., Gehrke, A. R., Talukder, S., Philippakis, A. a, Peña-Castillo, L., Alleyne, T. M., Mnaimneh, S., Botvinnik, O. B., Chan, E. T., et al. (2008). Variation in homeodomain DNA binding revealed by high-resolution analysis of sequence preferences. Cell 133, 1266-1276.

Blair, J. D., Bateup, H. S., and Hockemeyer, D. F. (2016). Establishment of Genome-edited Human Pluripotent Stem Cell Lines: From Targeting to Isolation. J. Vis. Exp. 1-9.

Briscoe, J., and Ericson, J. (1999). The specification of neuronal identity by graded Sonic Hedgehog signalling. Semin. Cell Dev. Biol. 10, 353-362.

Bugaj, L. J., Spelke, D. P., Mesuda, C. K., Varedi, M., Kane, R. S., and Schaffer, D. V (2015). Regulation of endogenous transmembrane receptors through optogenetic Cry2 clustering. Nat. Commun. 6, 6898.

Chambers, S. M., Fasano, C. a, Papapetrou, E. P., Tomishima, M., Sadelain, M., and Studer, L. (2009). Highly efficient neural conversion of human ES and iPS cells by dual inhibition of SMAD signaling. Nat. Biotechnol. 27, 275-280.

Chen, J. K., Taipale, J., Young, K. E., Maiti, T., and Beachy, P. A. (2002). Small molecule modulation of Smoothened activity. Proc. Natl. Acad. Sci. 99, 14071-14076.

Chiba, K., Johnson, J. Z., Vogan, J. M., Wagner, T., Boyle, J. M., and Hockemeyer, D. (2015). Cancer-associated TERT promoter mutations abrogate telomerase silencing. Elife 4, 1-20.

Cong, L., Ran, F. A., Cox, D., Lin, S., Barretto, R., Habib, N., Hsu, P. D., Wu, X., Jiang, W., Marraffini, L. A., et al. (2013). Multiplex genome engineering using CRISPR/Cas systems. Science 339, 819-823.

Conway, A., Spelke, D. P., and Schaffer, D. V (2013). Conjugation of Proteins to Polymer Chains to Create Multivalent Molecules. Methods Mol. Biol. 1202, 95-102.

De la Fuente, A. G., Errea, O., van Wijngaarden, P., Gonzalez, G. a, Kerninon, C., Jarjour, A. a, Lewis, H. J., Jones, C. a, Nait-Oumesmar, B., Zhao, C., et al. (2015). Vitamin D receptor-retinoid X receptor heterodimer signaling regulates oligodendrocyte progenitor cell differentiation. J. Cell Biol. 211, 975-985.

Douvaras, P., and Fossati, V. (2015). Generation and isolation of oligodendrocyte progenitor cells from human pluripotent stem cells. Nat. Protoc. 10, 1143-1154.

Douvaras, P., Wang, J., Zimmer, M., Hanchuk, S., O'Bara, M. A., Sadiq, S., Sim, F. J., Goldman, J., and Fossati, V. (2014). Efficient Generation of Myelinating Oligodendrocytes from Primary Progressive Multiple Sclerosis Patients by Induced Pluripotent Stem Cells. Stem Cell Reports 3, 250-259.

Engler, A. J., Sen, S., Sweeney, H. L., and Discher, D. E. (2006). Matrix elasticity directs stem cell lineage specification. Cell 126, 677-689.

Fu, H., Qi, Y., Tan, M., Cai, J., Takebayashi, H., and Nakafuku, M. (2002). Dual origin of spinal oligodendrocyte progenitors and evidence for the cooperative role of Olig2 and Nkx2.2 in the control of oligodendrocyte differentiation. Development 129, 681-693.

Goldman, S. a, and Kuypers, N. J. (2015). How to make an oligodendrocyte. Development 142, 3983-3995.

Hockemeyer, D., Soldner, F., Beard, C., Gao, Q., Mitalipova, M., DeKelver, R. C., Katibah, G. E., Amora, R., Boydston, E. a, Zeitler, B., et al. (2009). Efficient targeting of expressed and silent genes in human ESCs and iPSCs using zinc-finger nucleases. Nat. Biotechnol. 27, 851-857.

Hu, B.-Y., Du, Z.-W., and Zhang, S.-C. (2009a). Differentiation of human oligodendrocytes from pluripotent stem cells. Nat. Protoc. 4, 1614-1622.

Hu, B.-Y., Du, Z.-W., Li, X.-J., Ayala, M., and Zhang, S.-C. (2009b). Human oligodendrocytes from embryonic stem cells: conserved SHH signaling networks and divergent FGF effects. Development 136, 1443-1452.

Huang, Y.-L., Walker, A. S., and Miller, E. W. (2015). A Photostable Silicon Rhodamine Platform for Optical Voltage Sensing. J. Am. Chem. Soc. 137, 10767-10776.

Kang, S.-M., Cho, M. S., Seo, H., Yoon, C. J., Oh, S. K., Choi, Y. M., and Kim, D.-W. (2007). Efficient induction of oligodendrocytes from human embryonic stem cells. Stem Cells 25, 419-424.

Káradóttir, R., Hamilton, N. B., Bakiri, Y., and Attwell, D. (2008). Spiking and nonspiking classes of oligodendrocyte precursor glia in CNS white matter. Nat. Neurosci. 11, 450-456.

Keirstead, H. S., Nistor, G., Bernal, G., Totoiu, M., Cloutier, F., Sharp, K., and Steward, O. (2005). Human embryonic stem cell-derived oligodendrocyte progenitor cell transplants remyelinate and restore locomotion after spinal cord injury. J. Neurosci. 25, 4694-4705.

Kerr, C. L., Letzen, B. S., Hill, C. M., Agrawal, G., Thakor, N. V, Sterneckert, J. L., Gearhart, J. D., and All, A. H. (2010). Efficient differentiation of human embryonic stem cells into oligodendrocyte progenitors for application in a rat contusion model of spinal cord injury. Int. J. Neurosci. 120, 305-313.

Kotterman, M. a, Vazin, T., and Schaffer, D. V (2015). Enhanced selective gene delivery to neural stem cells in vivo by an adeno-associated viral variant. Development 142, 1885-1892.

Lei, Y., and Schaffer, D. V (2013). A fully defined and scalable 3D culture system for human pluripotent stem cell expansion and differentiation. Proc. Natl. Acad. Sci. U.S.A 110, E5039-48.

Lengner, C. J., Gimelbrant, A. A., Erwin, J. A., Cheng, A. W., Guenther, M. G., Welstead, G. G., Alagappan, R., Frampton, G. M., Xu, P., Muffat, J., et al. (2010). Derivation of pre-X inactivation human embryonic stem cells under physiological oxygen concentrations. Cell 141, 872-883.

Livesey, M. R., Magnani, D., Clearly, E. M., Vasisthe, N. A., James, O. T., Selvaraj, B. T., Burr, K., Story, D., Shaw, C. E., Kind, P. C., et al. (2016). Maturation and Electrophysiological Properties of Human Pluripotent Stem Cell-Derived Oligodendrocytes. Stem Cells 34, 1040-1053.

Lu, Q. R., Sun, T., Zhu, Z., Ma, N., Garcia, M., Stiles, C. D., and Rowitch, D. H. (2002). Common Developmental Requirement for Olig Function Indicates a Motor Neuron/Oligodendrocyte Connection. Cell 109, 75-86.

Masahira, N., Takebayashi, H., Ono, K., Watanabe, K., Ding, L., Furusho, M., Ogawa, Y., Nabeshima, Y., Alvarez-Buylla, A., Shimizu, K., et al. (2006). Olig2-positive progenitors in the embryonic spinal cord give rise not only to motoneurons and oligodendrocytes, but also to a subset of astrocytes and ependymal cells. Dev. Biol. 293, 358-369.

Maury, Y., Côme, J., Piskorowski, R. a, Salah-Mohellibi, N., Chevaleyre, V., Peschanski, M., Martinat, C., and Nedelec, S. (2015). Combinatorial analysis of developmental cues efficiently converts human pluripotent stem cells into multiple neuronal subtypes. Nat. Biotechnol. 33, 89-96.

Metsalu, T., and Vilo, J. (2015). ClustVis: a web tool for visualizing clustering of multivariate data using Principal Component Analysis and heatmap. Nucleic Acids Res. 43, W566-70.

Najm, F. J., Madhavan, M., Zaremba, A., Shick, E., Karl, R. T., Factor, D. C., Miller, T. E., Nevin, Z. S., Kantor, C., Sargent, A., et al. (2015). Drug-based modulation of endogenous stem cells promotes functional remyelination in vivo. Nature 522, 216-220.

Okada, Y., Shimazaki, T., Sobue, G., and Okano, H. (2004). Retinoic-acid-concentration-dependent acquisition of neural cell identity during in vitro differentiation of mouse embryonic stem cells. Dev. Biol. 275, 124-142.

Park, H.-C., Mehta, A., Richardson, J. S., and Appel, B. (2002). olig2 Is Required for Zebrafish Primary Motor Neuron and Oligodendrocyte Development. Dev. Biol. 248, 356-368.

Qi, Y., Cai, J., Wu, Y., Wu, R., Lee, J., Fu, H., Rao, M., and Sussel, L. (2001). Control of oligodendrocyte differentiation by the Nkx2.2 homeodomain transcription factor. Development 128, 2723-2733.

Sontheimer, H., Trotter, J., Schachner, M., and Kettenmann, H. (1989). Channel Expression Correlates with Differentiation Stage during the Development of Oligodendrocytes from Their Precursor Ceils in Culture. Neuron 2, 1135-1145.

Stacpoole, S. R. L., Spitzer, S., Bilican, B., Compston, A., Karadottir, R., Chandran, S., and Franklin, R. J. M. (2013). High yields of oligodendrocyte lineage cells from human embryonic stem cells at physiological oxygen tensions for evaluation of translational biology. Stem Cell Reports 1, 437-450.

Takebe, T., Enomura, M., Yoshizawa, E., Kimura, M., Koike, H., Ueno, Y., Matsuzaki, T., Yamazaki, T., Toyohara, T., Osafune, K., et al. (2015). Vascularized and Complex Organ Buds from Diverse Tissues via Mesenchymal Cell-Driven Condensation. Cell Stem Cell 16, 556-565.

Wang, S., Bates, J., Li, X., Schanz, S., Chandler-Militello, D., Levine, C., Maherali, N., Studer, L., Hochedlinger, K., Windrem, M., et al. (2013). Human iPSC-derived oligodendrocyte progenitor cells can myelinate and rescue a mouse model of congenital hypomyelination. Cell Stem Cell 12, 252-264.

Zhou, Q., Choi, G., and Anderson, D. J. (2001). The bHLH Transcription Factor Olig2 Promotes Oligodendrocyte Differentiation in Collaboration with Nkx2.2. Neuron 31, 791-807.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A three-dimensional culture system comprising:

a) biocompatible thermoresponsive polymer that forms a hydrogel at 37° C.; and b) a combination of factors that promote differentiation of oligodendrocyte precursors from pluripotent stem cells in 20 days or less, wherein the combination of factors consists of a Sonic hedgehog (Shh) signaling pathway agonist and retinoic acid (RA); and wherein the thermoresponsive polymer comprises:

an N-isopropylacrylamide co-monomer;

an alkyl [meth]acryl[ate/amide] co-monomer, wherein the alkyl is a lower alkyl group;

a PEG acrylamide co-monomer; and a modifying acryl[ate/amide] co-monomer comprising a linked functional group or a linked modifying agent, wherein the thermoresponsive polymer is described by formula (II):

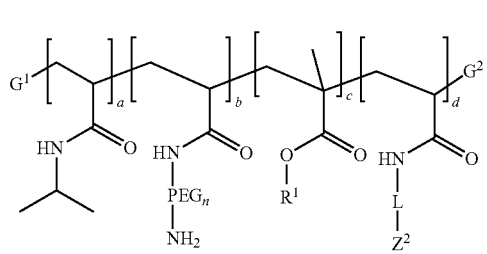

(II)

wherein:
- a, b, c and d are molar fractions of the co-monomers, wherein a >0.8, 0.1>b>0, and 0.2>c>0;
- $PEG_n$ is a polyethylglycol polymer;
- $Z^2$ is a functional group or a linked modifying agent;
- L is a linker;
- $R^1$ is a lower alkyl;
- $G^1$ and $G^2$ are each independently selected from a polymer segment, a terminal group, a linker and a linked modifying agent.

2. The culture system of claim 1, wherein:
the Shh signaling pathway agonist is 3,4-dichloro-N-(cis-4-(methylamino)cyclohexyl)-N-(3-pyridin-4-ylbenzyl)benzo[b]thiophene-2-carboxamide, an Shh polypeptide, an Shh protein-polymer conjugate, or a compound of the formula:

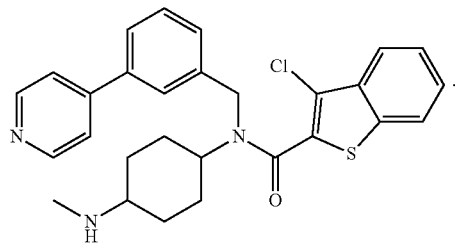 [SMILES: CNC1CCC(N(Cc2cccc(-c3ccncc3)c2)C(=O)c2sc3ccccc3c2Cl)CC1]

3. The culture system of claim 1, comprising a pluripotent stem cell.

4. The three-dimensional culture system of claim 1, wherein the Shh signaling pathway agonist is a small molecule.

5. The three-dimensional culture system of claim 1, wherein the alkyl [meth]acryl[ate/amide] co-monomer is an isobutyl methacrylate co-monomer.

6. The three-dimensional culture system of claim 1, wherein $R^1$ is selected from the group consisting of methyl, ethyl, propyl, butyl, pentyl, isopropyl, isobutyl, isopentyl, tert-butyl, cyclopropyl, and cyclobutyl.

7. The three-dimensional culture system of claim 1, wherein $Z^2$ is a chemoselective functional group.

8. The three-dimensional culture system of claim 1, wherein the thermoresponsive polymer is described by the formula (IV):

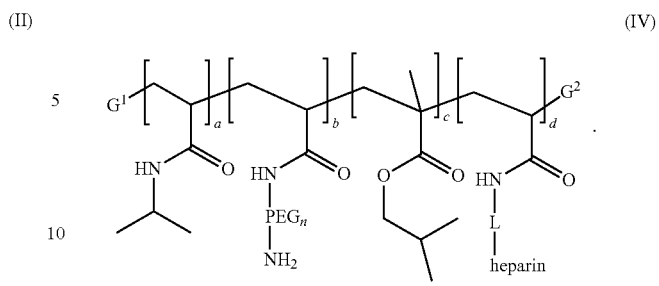

(IV)

9. The three-dimensional culture system of claim 1, wherein $G^1$ and $G^2$ are each independently selected from a terminal group, a linker and a linked modifying agent.

10. The three-dimensional culture system of claim 1, wherein $G^1$, $G^2$ or $Z^2$ comprise a linked hyaluronic acid that is linked via conjugation to the carboxylic acid group of a hyaluronic acid monomer.

11. The three-dimensional culture system of claim 1, wherein $G^1$, $G^2$ or $Z^2$ comprise the following structure:

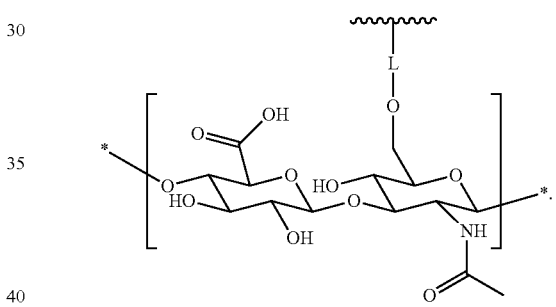

12. The three-dimensional culture system of claim 11, wherein $Z^2$ comprises the following structure:

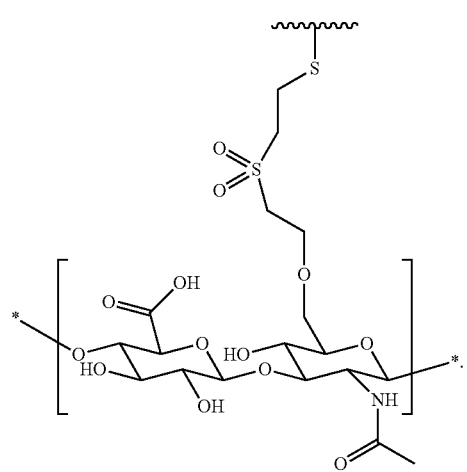

13. The three-dimensional culture system of claim 1, wherein $G^1$ and/or $G^2$ comprises the following structure:

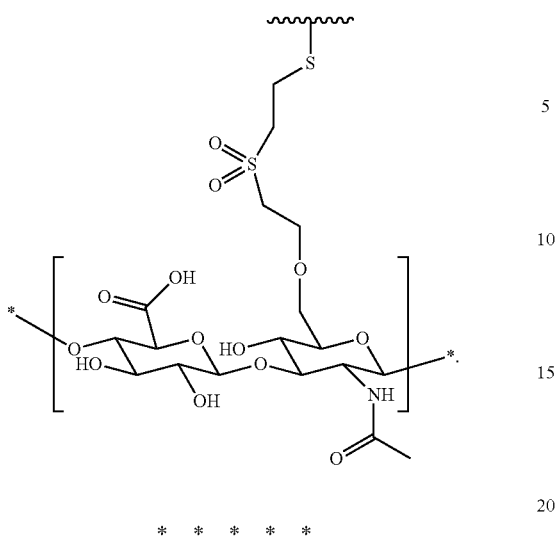

UNITED STATES PATENT AND TRADEMARK OFFICE
CERTIFICATE OF CORRECTION

PATENT NO. : 11,111,375 B2
APPLICATION NO. : 15/758231
DATED : September 7, 2021
INVENTOR(S) : Gonçalo Rodrigues et al.

Page 1 of 1

It is certified that error appears in the above-identified patent and that said Letters Patent is hereby corrected as shown below:

In the Specification

In Column 27, Line 11, please replace "9.7 M" with --- 9.7 µM ---;

In Column 31, Line 9, please replace "p" with --- β ---;

In Column 31, Line 25, please replace "a" with --- α ---;

In Column 31, Line 25, please replace "3" with --- β ---;

In Column 31, Line 27, please replace "a" with --- α ---;

In Column 31, Line 27, please replace "3" with --- β ---;

In Column 39, Line 46, please replace "O1 ng/mL" with --- 10ng/mL ---; and

In Column 50, Line 55, please replace "100 am" with --- 100 µm ---.

Signed and Sealed this
Twenty-second Day of March, 2022

Drew Hirshfeld
*Performing the Functions and Duties of the
Under Secretary of Commerce for Intellectual Property and
Director of the United States Patent and Trademark Office*